US007001748B2

(12) United States Patent
Gokhale et al.

(10) Patent No.: US 7,001,748 B2
(45) Date of Patent: *Feb. 21, 2006

(54) METHODS OF MAKING POLYKETIDES USING HYBRID POLYKETIDE SYNTHASES

(75) Inventors: Rajesh S. Gokhale, New Delhi (IN); Stuart Tsuji, Stanford, CA (US); Chaitan Khosla, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 243 days.

This patent is subject to a terminal disclaimer.

(21) Appl. No.: 10/091,244

(22) Filed: Mar. 4, 2002

(65) Prior Publication Data

US 2003/0068676 A1 Apr. 10, 2003

Related U.S. Application Data

(63) Continuation-in-part of application No. 09/500,747, filed on Feb. 9, 2000, now Pat. No. 6,753,173.
(60) Provisional application No. 60/119,363, filed on Feb. 9, 1999, provisional application No. 60/272,985, filed on Mar. 2, 2001, and provisional application No. 60/272,987, filed on Mar. 2, 2001.

(51) Int. Cl.
   *C12P 19/62* (2006.01)

(52) U.S. Cl. .................................................... 435/76
(58) Field of Classification Search ................ 435/76; 436/76
   See application file for complete search history.

(56) References Cited

U.S. PATENT DOCUMENTS

| | | | |
|---|---|---|---|
| 4,551,433 A | 11/1985 | DeBoer | 435/253 |
| 4,874,748 A | 10/1989 | Katz et al. | 514/29 |
| 4,935,340 A | 6/1990 | Baltz et al. | |
| 5,063,155 A | 11/1991 | Cox et al. | 435/76 |
| 5,098,837 A | 3/1992 | Beckmann et al. | 435/172.3 |
| 5,149,639 A | 9/1992 | Katz et al. | 435/76 |
| 5,168,052 A | 12/1992 | Cox et al. | 435/72 |
| 5,252,474 A | 10/1993 | Gewain et al. | 435/172.3 |
| 5,475,099 A | 12/1995 | Knauf et al. | |
| 5,514,544 A | 5/1996 | Rao et al. | 435/6 |
| 5,672,491 A | 9/1997 | Khosla et al. | 435/148 |
| 5,712,146 A | 1/1998 | Khosla et al. | 435/252.35 |
| 5,824,513 A | 10/1998 | Katz | 435/76 |
| 5,830,750 A | 11/1998 | Khosla et al. | 435/252.35 |
| 5,843,718 A | 12/1998 | Khosla et al. | 435/69.1 |
| 6,004,787 A | 12/1999 | Katz et al. | 435/183 |
| 6,060,234 A | 5/2000 | Katz et al. | 435/4 |
| 6,063,561 A | 5/2000 | Katz et al. | 435/4 |
| 6,066,721 A | 5/2000 | Khosla et al. | |
| 6,080,555 A | 6/2000 | Khosla et al. | |
| 6,200,813 B1 | 3/2001 | Katz et al. | 435/477 |
| 6,271,255 B1 | 8/2001 | Leadlay et al. | 514/450 |

FOREIGN PATENT DOCUMENTS

| | | |
|---|---|---|
| WO | WO 93 13663 | 7/1993 |
| WO | WO 95 08548 | 3/1995 |
| WO | WO 96 40968 | 12/1996 |
| WO | WO 97 02358 | 1/1997 |
| WO | WO 97 14789 | 4/1997 |
| WO | WO 98 01546 | 1/1998 |
| WO | WO 98 01571 | 1/1998 |
| WO | WO 98/27203 | 6/1998 |
| WO | WO 98/49315 | 11/1998 |
| WO | WO 98/54308 | 12/1998 |
| WO | WO 00/01838 | 1/2000 |

OTHER PUBLICATIONS

August et al., Chem. Biol. (1998) 4:69.
Belshaw, P. J.; Walsh, C. T.; Stachelhaus, T.*Science*(1999) 284, 486–489.
Bycroft, M.; Weissmas, K. J.; Staunton, J.; Leadlay, P. F. *Eur. J. Biochem.* (2000) 267, 520–526.
Cane et al., Science (1998) 282:63.
Chen, Y. H., Yang, J.T., and Chau, K. H. (1974) *Biochemistry 13,* 3350–3359.
Chuck, J., McPherson, M., Huang, H.; Jacobsen, J. R., Khosla, C., and Cane, D. E. (1997) *Chem. Biol. 4,* 757–766.
Cortes, J.; Weismann, K. E.; Roberts, G. A.; Brown, M. J.; Staunton, J.; Leadlay, P. F. *Science* (1995) 268, 1487–1489.
Donadio et al., Science (1991) 252:675.
Dreier, J., Shah, A. N., and Khosla, C. (1999) *J. Biol. Chem.* 274, 25108–25112.
Geck, M. K.; Kirsch, J. F. *Biochemistry*(1999) 38, 8032–8037.
Gokhale, R. S., and Khosla, C. (2000) *Curr. Opin. Chem. Biol. 4,* 22–27.
Gokhale, R. S., Hunziker, D., Cane, D. E., and Khosla, C. (1999) *Chem. Biol. 6,* 117–125.
Harris, R. C.; Cutter, A. L.; Weissman, K. J.; Hanefeld, U.; Timoney, M.; Staunton, J. *J. Chem. Res. (S)*(1998) 6, 283.
Holzbaur, I. E.; Harris, R. C.; Bycroft, M.; Cortes, J.; Bisang, C.; Staunton, J.; Rudd, B. A. M.; Leadlay, P. F. *Chem. Biol.* (1999) 6, 189–195.
Hopwood, Chem. Rev. (1997) 97:2465.
Hunziker, D.; Wu, N.; Kenoshita, K.; Cane, D. E.; Khosla, C. *Tetrahedron Lett.* (1999) 40, 635–638.

(Continued)

*Primary Examiner*—Kathleen Kerr
(74) *Attorney, Agent, or Firm*—Morrison & Foerster LLP

(57) ABSTRACT

Linking sequences which modulate cross-talk between modules of Type I polyketide synthases have been identified. Thus, arbitrarily chosen modules can be mixed and matched by supplying the appropriate linkers to obtain desired polyketide synthases and new polyketides. The modules are provided suitable linkers so that the polyketide chain is passed from one module to the other in the correct sequence. Synthetic peptides which mimic linkers can be used to inhibit the synthesis of polyketides. Kinetic channeling, both intrapolypeptide and interpolypeptide, of diketide intermediates in a Type I polyketide synthase can occur.

12 Claims, 22 Drawing Sheets

OTHER PUBLICATIONS

Jacobsen, J. R., Hutchinson, C. R., Cane, D. E., and Khosla, C. (1997) *Science 277*, 367–369.

Jacobsen, J. R.; KeatingeClay, A. C.; Cane, D. E., Khosla, C. *Bioorgan. Med. Chem.* (1998) 6, 1171–1177.

Kao et al., J. Am. Chem. Soc. (1996) 35:12363.

Kao, C. M.; McPHerson, M.; McDaniel, R. N.; Fu, H.; Cane, D. E.; Khosla, C. J. *J. Am. Chem. Soc.* (1998) 120, 2478–2479.

Katz, Chem. Rev. (1997) 97:255.

Khosla, C.; Gokhale, R. S.; Jacobsen, J. R.; Cane, D. E. *Annu. ReV. Biochem*(1999) 68, 219–253.

Lambalot et al., Chem. Biol. (1996) 3:92.

Lau, J.; Cane, D. E.; Khosla, C. *Biochemistry*(2000) 39, 10514–10520.

Liu, L.; Thamchaipenet, A.; Fu, H.; Betlach, M.; Ashley, G. *J. Am. Chem. Soc.*(1997) 119, 10553–10554.

Lupas, A. (1996) *Methods Enzymol. 266*, 513–525.

Lupas, A., Van Dyke, M., and Stock, J. (1991) *Science 252*, 1162–1164.

McDaniel, R.; Kao, C.; Fu, H.; Hevezi, P.; Gustafson, C.; Betlach, M.; Ashley, G.; Cane, D. E.; Khosla, C. *J. Am. Chem. Soc.* (1997) 119, 4309–4310.

McDaniel, R.; Thamchaipenet, A.; Gustafsson, C.; Fu, H.; Betlach, M.; Ashley, G. *Proc. Natl. Acad. Sci. U.S.A.*(1990), 96, 1846–1851.

McPherson, M.; Khosla, C.; Cane, D. E. *J. Am. Chem. Soc.*(1998) 120, 3267–3268.

Nakano et al., Mol. Gen. Genet. (1992) 232:31.

Pieper, R., Luo, G., Cane, D. E., and Khosla, C. (1995) *J. Am. Chem. Soc. 117*, 11373–11374.

Pieper, R., Luo, G., Cane, D. E., and Khosla, C. (1995) *Nature 378*, 263–266.

Pieper, R.; Ebert–Khosla, S.; Cane, D.; Khosla, C. *Biochemistry*(1996) 35, 2054–2060.

Pohl et al., J. Am. Chem. Soc. (1998) 120:1120.

Quadri, L. E. N.; Weinreb, P. H.; Mei, M.; Nakano, M. M.; Zuber, P.; Walsh, C. T. *Biochemistry* (1998) 37, 1585–1595.

Robertson, S. A.; Ellman, J. A.; Schultz, P. G. *J. Am. Chem. Soc*(1991) 113, 2722–2729.

Schupp et al., FEMS Microbiol. Lett. (1998) 159:20.

Tsuji, S. Y.; Cane, D. E.; Khosla, C. *Biochemistry* 40: 2326 (2001).

Weinreb, P. H.; Quadri,, L. E. N.; Walsh, C. T.; Zuber, P. *Biochemistry* (1998 37, 1575–1584.

Wu, N.; Kudo, F., Cane, D. E., and Khosla, C. (2000) *J. Am. Chem. Soc. 122*, 4847–4852.

Aparicio et al., J. of Biol. Chem. (1994) 269(11):8524–8528.

Aparicio, Gene (1996) 169:9–16.

Bao, W. et al. (1998). Biochemistry 37(22):8132–8138.

Bartel et al., J. Bacteriol. (1990) 172(9):4816–4826.

Beck et al., Eur. J. Biochem. (1990) 192:487–498.

Bedford, D. et al. (1996), Chem & Biol 3(10):827–831.

Bevitt et al. Eur. J. Biochem. (1992) 204:39–49.

Bibb et al., EMBO J. (1989) 8(9):2727–2736.

Bohm et al., Chem. & Biol. (1998) 5:407.

Brown et al., J. Chem. Soc. Chem. Commun. (1995) 15:1517–1518.

Caballero et al., Mol. Gen. Genet. (1991) 230:401–412.

Caffrey et al., Eur. J. Biochem. (1991 195:823–830.

Caffrey et al., FEBS Lett. (1992) 304:225–228.

Cane et al., J. Am. Chem. Soc. (1993) 115:522–526.

Cane et al., J. Antibiotics (1995) 48:647–651.

Corcoran et al., in 5th International Congress of Chemotherapy, Vienna, Abstracts of Communications (1967) pp. 35–40.

Corcoran, ed., in Antibiotics vol. IV Biosynthesis, Springer–Verlag, New York (1982) pp. 145–150.

Cortes et al., Nature (1990) 348:176–178.

Dalbie–McFarland et al., Proc. Natl. Acad. Sci. USA (1982) 79:6409.

Davis et al., Abst. of the Genetics of Industrial Microorganisms Mtg. (1994) P288:192.

Dimroth et al., Eur. J. Biochem. (1970) 13:98–110.

Donadio et al., Gene (1992) 111:51–60.

Donadio et al., Gene (1992) 115: 97–103.

Donadio et al., Industrial Microorganism Basic and Applied Molecular Genetics, R. H . Baltz, G.D. Hegeman and PIL. Skatrud (eds) (Amer. Soc. Microbial.), Washington, D.C. (1993) pp. 251–265.

Donadio et al. Proc. Natl. Acad. Sci. USA (1993) 90:7119–7123.

Donadio et al., Science (1991) 252:675–679.

Evans et al,, J. Am. Chem. Soc. (1992) 114:9434–9453.

Fernandez–Moreno et al., Cell (1991) 66:769–780.

Fernandez–Moreno et al., J. Biol. Chem. (1992) 267:19278–19290.

Floss, Tetrahydron (1991) 47(31):6045–6058.

Fu et al., "Engineered Biosynthesis of Novel Polyketides: Stereochemical Course of Two Reactions Catalyzed by a Polyketide Synthase," *Biochemistry* (1994) 33:9321–9326.

Geisselsoder et al., BioTechniques (1987) 5:786.

Gokhale et al., *Biochemistry* (1998) 37:2524–2528.

Gokhale et al., *Science* (1999) 284:482–485.

Gordon et al., Acc. Chem. Res. (1996) 29(3):144–154.

Hallam, Gene (1988) 74:305–320.

Hamilton et al., J. Bacteriol. (1989) 171:4617.

Hershberger et al. (1989) "Genetics and Molecular Biology of Industrial Microorganisms," Am. Soc. for Microbiol. (Washington, DC) pp. 68–84.

Hopwood et al., Nature (1985) 314(6012):642–644.

Hopwood et al., Phil. Trans. R. Soc. Lond. B (1989) 324:549–562.

Hopwood et al., Secondary Metabolites: Their Function and Evolution (1992) Wiley Chichester (Ciba Foundation Symposium 171) pp. 88–112.

Hunaitit et al., Antimicrobial Agents and Chemotherapy (1984) 25(2):173–178.

Hutchinson, Bio Technology (1994) 12:375–380.

Ireland et al., J. Org. Chem. (1980) 45:1868–1880.

Jay et al., J. Biol. Chem. (1984) 259:6311–6317.

Kakavas, S. et al. (1997) *J. of Bacteriology* 179(23):7515–7522.

Kao et al., J. Am. Chem. Soc. (1994) 16:11612–11613.

Kao et al., J. Am. Chem. Soc. (1995) 117(35):9105–9106.

Kao et al., J. Am. Chem. Soc. (1996) 118(38):9184–9185.

Kao et al., J. Am. Chem. Soc. (1997) 119(46):11339–11340.

Kao et al., "Engineered Biosynthesis of a Complete Macrolactone in a Heterologous Host," *Science* (1994) 265:509–512.

Kao et al., Biochemistry (1996) 35:12363–12368.

Katz et al., Ann. Review Microbiol. (1993) 47:875–912.

Khosla et al., J. Bacteriol. (1993) 175:2197–2204.

Khosla et al., Molec. Microbiol. (1992) 6(12):3237–3249.

Khosla et al., "Harnessing the Biosynthetic Potential of Modular Polyketide Synthases," *Clin. Rev* (1997) 97:2577–2590.

Khosla et al., "Generation of Polyketide Libraries Via Combinatorial Biosynthesis," *Trends Biotechnol* (1996) 14(9):335–341.
Kramer et al., J. Am. Chem. Soc. (1997) 119(4):635–639.
Kuhstoss et al., Gene (1996) 183:231–236.
Kunkel, Proc. Natl. Acad. Sci. USA (1985) 82:448.
Lambalot et al., J. Antibiotics (1992) 45:1981–1982.
Lanz et al., J. of Biol. Chem. (1991) 266(15):9971–9976.
Lau et al., Biochemistry (1999) 38:1643–1651.
Leadlay et al., Biochem. Soc. Transactions (1993) 21:218–222.
Lehrer et al., J. Immun. Meth. (1991) 137:167–173.
MacNeil, J. Bacteriol. (1988) 170:5607.
MacNeil et al., Gene (1992) 115:119–125.
Malpartida et al., Nature (1984) 309:462–464.
Malpartida et al., Mol. Gen. Genet. (1986) 205:66–73.
Malpartida et al., Nature (1987) 325(6107):818–821.
Marsden et al., Science (1994) 263:378–380.
Marsden et al., Science (1998) 279:199–202.
Martin et al., J. Am. Chem. Soc. (1997) 119:3193.
Masamune et al., J. Am. Chem. Soc. (1975) 97:3512–3513.
Masumoto et al., Tetrahedron Lett. (1988) 29:3575.
McAlpine et al., The Journal of Antibiotics (1987) 40(8):1115–1122.
McDaniel, R. et al. (1997), *Chem. & Biol* 4(9):667–674.
McDaniel et al., "Engineered Biosynthesis of Novel Polyketides," *Science* (1993) 262: 1546–1550.
Oliynyk et al., Chem. and Biol. (1996) 3:833–839.
Omura et al., J. Biochem. (1974) 75:193–195.
Perun, Drug Action and Drug Resistance in Bacteria, vol. 1, S. Mitsuhashi (ed.) Univ. Park Press, Baltimore, 1977.
Pieper et al., Biochemistry (1997) 36:1846–1851.
Ranganathan et al., "Knowledge–based Design of Bimodular and Trimodular Polyketide Synthases Based on Domain and Module Swaps: A Route to Simple Statin Analogues," *Chem. & Biol* (1999) 6:731–741.
Roberts et al., FEBS Lett. (1983) 159(1,2):13–16.
Roberts et al., Biochem. Soc. Transactions (1984) 12 642–643.
Roberts et al., Biochem. Soc. Transactions (1992) 21 325.
Roberts et al., Eur. J. Biochem. (1993) 214:305–311.
Robinson, Phil. Trans. R. Soc. Lond B (1991) 332:107–114.
Rohr, "Combinatorial Biosynthesis—An Approach in the Near Future?," *Angew Chem Int Ed Engl* (1995) 34(8):881–888.
Ruan et al., J. of Bacteriology (1997) 79(20):6416–6425.
Rudd et al., J. Gen. Microbiol. (1979) 114:35–43.
Sanz et al., Eur. J. Biochem. (1996) 235:601–605.
Shen et al., Science (1993) 262:1535–1540.
Sherman et al., J. Bacteriol. (1992) 174:6184–6190.
Sherman et al., EMBO J. (1989) 8:2717–2725.
Spencer et al., Biochem. J. (1992) 288:839–846.
Staunton et al., Nat. Struct. Biol. (1996) 3:188–192.
Staunton et al., "Biosynthesis of Erythromycin and Rapamycin," *Chem Rev* (1997) 97:2611–2629.
Strohl et al., Molecular Microbiology (1992) 6(2):147–152.
Strohl et al., Society of Industrial Microbiology (1991) 7:163–174.
Tang et al., Chem. Biol. (2000) 7:77–84.
Toshima et al., J. Am. Chem. Soc. (1995) 117:3717.
Tsoi et al., Chemistry & Biology (1985) 2:355–362.
Tuan et al., Gene (1990) 90:21.
Vedejs et al., J. Am. Chem. Soc. (1987) 109:5437–5446.
Vedejs et al., J. Am. Chem. Soc. (1989) 111:8430–8438.
Wawszkiewicz et al., Biochemische Zeitschrift (1964) 340:213–227.
Wiseman et al., Chemistry & Biology (1995) 2(9):583–589.

(a) INTRA-POLYPEPTIDE LINKER

```
M2ery:  GGATGAEQAAPATT..APVD
M4ery:  VGDAD..QAA.VRVVGAA.DES
M6ery:  VGAAEAEQA.PALVREVPKDAD
M2rif:  FGSA.A.NR.PAEIGTAAAE
M3rif:  LG..ER.PAAPAPVTRDVSD
M5rif:  GETVAGAPATPVTTVADAG
M3rap:  .ELFTGENPAPVRGPVSAVGQD
M4rap:  .ELFTGENPAPVRGPVSVVGQD
M7rap:  .ELFTGENPAPVRGPVSA.GQD
```

(b) N-TERMINAL INTER-POLYPETIDE LINKER

```
M3ery:   ......VTD SE KVAEYLRR .ATLDLRAAR QRIRE..LES
M5ery:   MSGDNGM.TE E.KLRRYLKR TVT.ELDSVT ARLRE..VEH RAG
M4rif:   ......MSAPNE QIVDAL.R ASLKE....N VRLQQENSAL AAAAA
M7rif:   ......VSASYE KVVEAL.R KSLEE....V GTLKKRNRQL ADAAG
M8rif:   ......V.AD EGQLRDYLKR .AIADARDAR TRLRE..VEE QAR
M9rif:   ......MATD E.KLLKYLKR .VTAELHS.. ..LRKQGARH .AD
M5rap:   ......MR.. EDQLLDAL.R KSVKE....N ARLRKANTSL RAAMD
M11rap:  ......M.PEQD KVVEYL.R WATAELHTTR AKL.....EA LAAANT
```

Figure 3

A. M2 and M3+TE
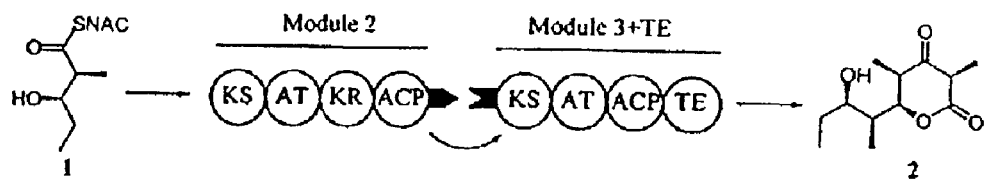
B. M2 and (5)M3+TE
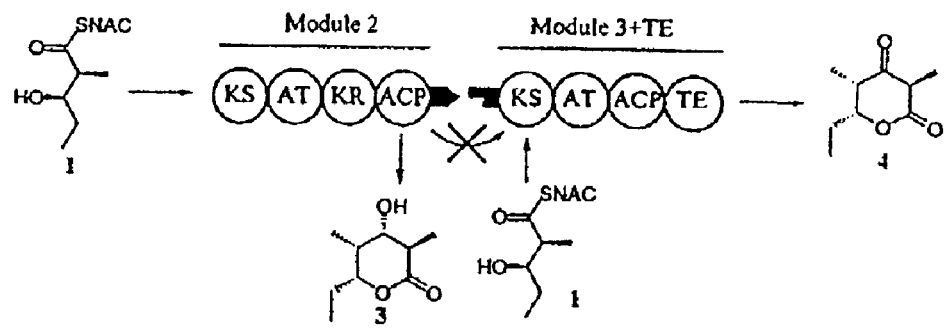
C. M2(4) and M3+TE
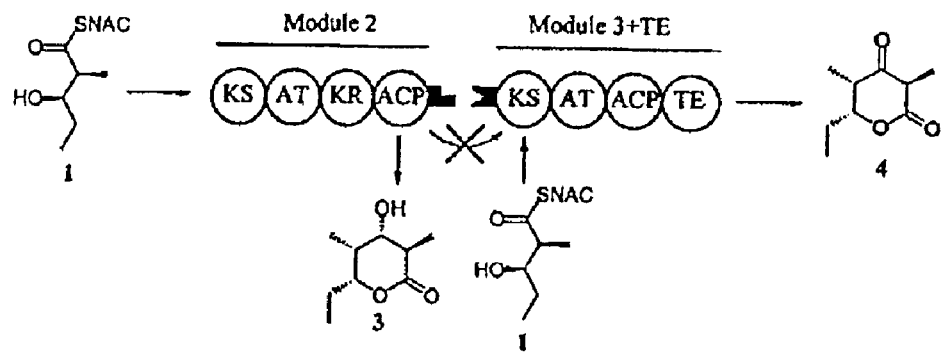
D. M2(4) and (5)M3+TE
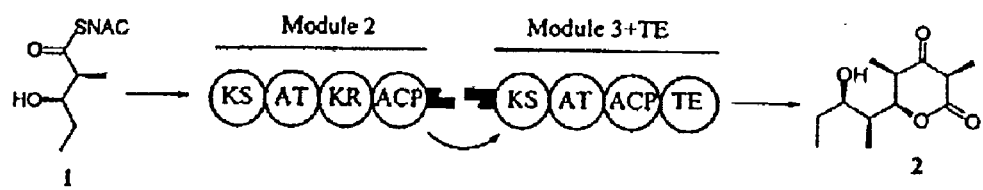
Figure 6

| Substrate | (5)Module 2 + TE | (5)Module 5 + TE | (5)Module 6 + TE |
|---|---|---|---|
| 4a | 2900 ± 500 | 290 ± 50 | 340 ± 60 |
| 4b | 18 ± 1 | 3.9 ± 0.7 | 85 ± 15 |
| 2a | 0.75 ± 0.01 | 0.016 ± 0.002 | 1.1 ± 0.1 |
| 2b | 0.0076 ± 0.0006 | 0.0011 ± 0.0001 | 0.058 ± 0.006 |

Figure 13

| Substrate | (S)Module 2 + TE<br>KS AT KR ACP TE | (S)Module 5 + TE<br>KS AT KR ACP TE | (S)Module 6 + TE<br>KS AT KR ACP TE |
|---|---|---|---|
| 4a | 6.7 ± 0.2 | > 9.3 ± 1.4 | > 10 ± 1 |
| 4b | > 0.97 ± 0.02 | > 0.48 ± 0.02 | > 3.4 ± 0.4 |
| 4c | > 1.0 ± 0.1 | > 1.4 ± 0.1 | > 2.1 ± 0.2 |
| 4d | > 0.29 ± 0.03 | > 0.20 ± 0.01 | > 1.9 ± 0.1 |
| 2a | > 4.6 ± 0.6 | 0.24 ± 0.01 | 17 ± 2.9 |
| 2b | 0.25 ± 0.02 | 0.017 ± 0.001 | 2.4 ± 0.2 |
| 2c | N.D. | N.D. | N.D. |
| 2d | N.D. | N.D. | N.D. |

Figure 14

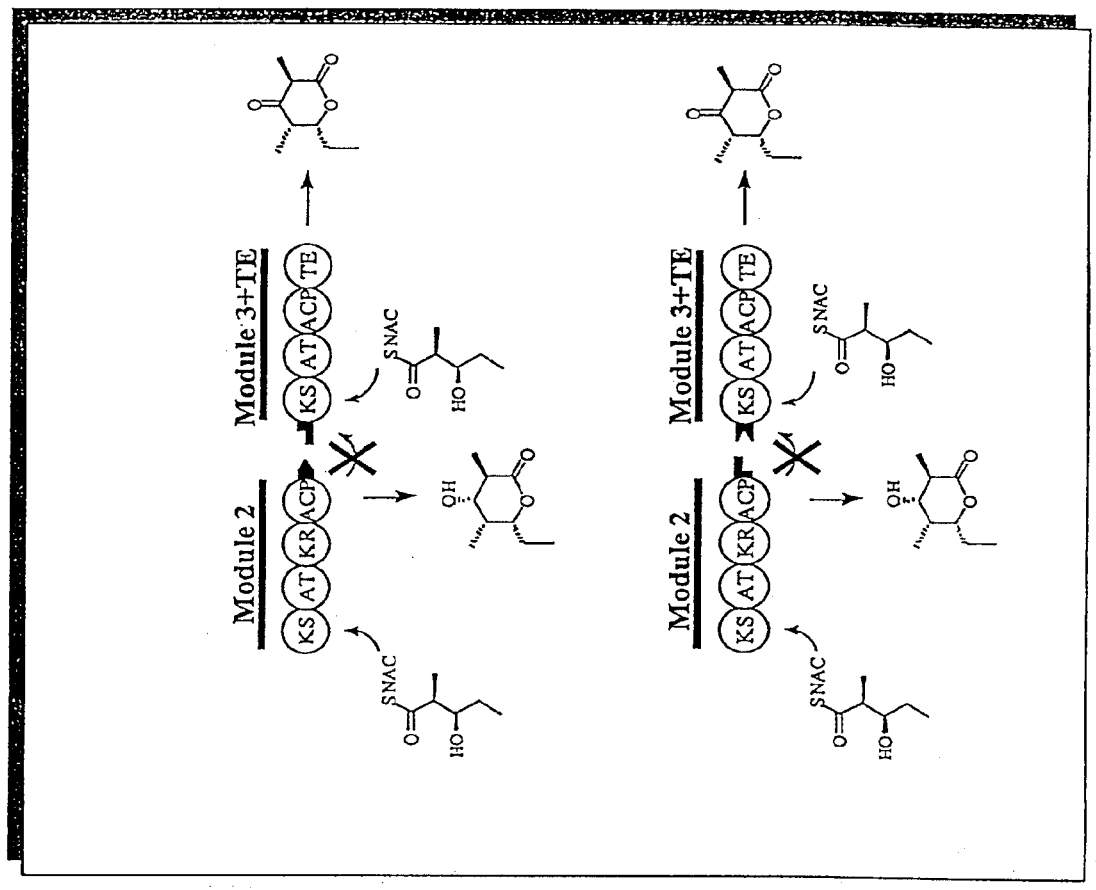
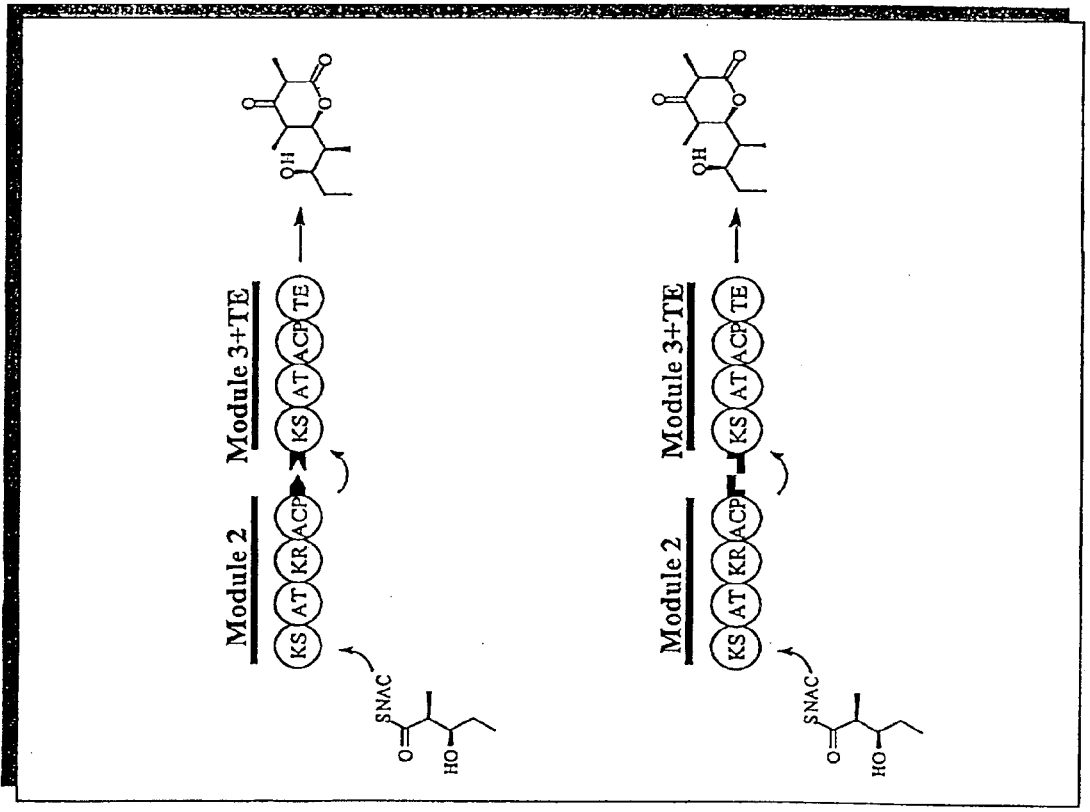
Figure 17

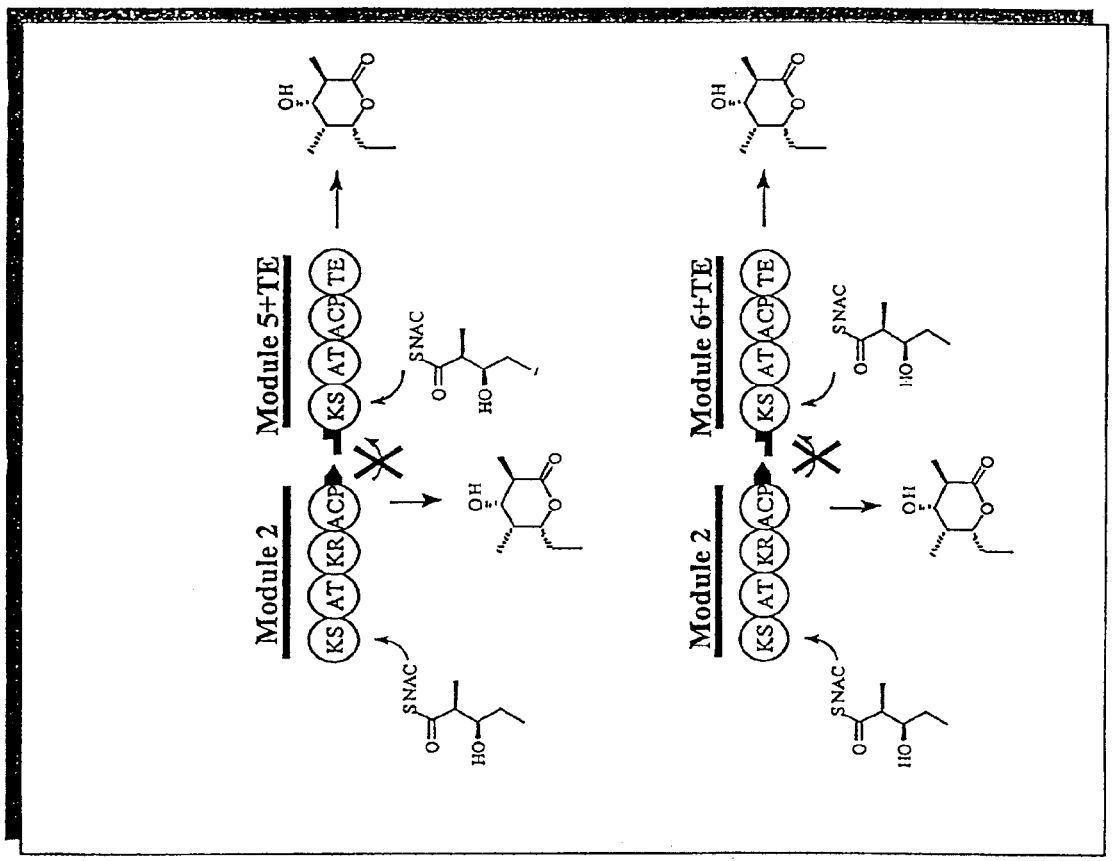
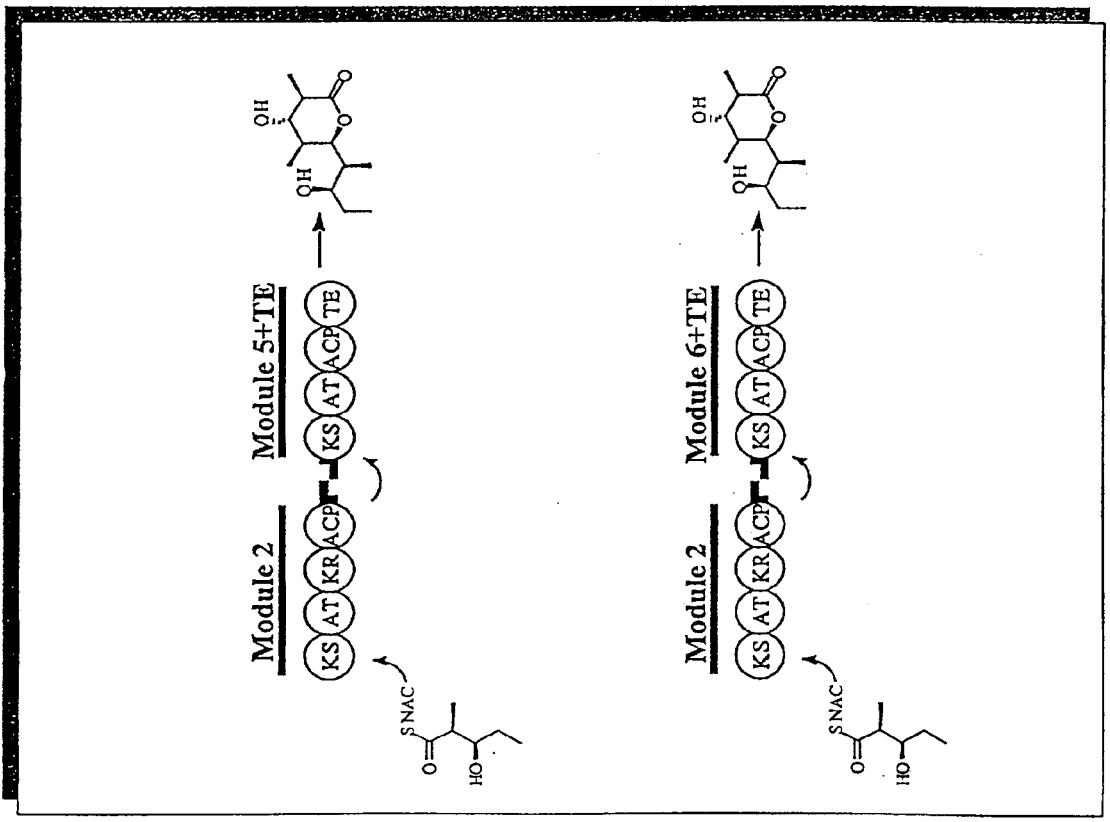
Figure 18

Figure 20

SEQUENCE LISTING

<160> NUMBER OF SEQ ID NOS: 24

<210> SEQ ID NO 1
<211> LENGTH: 15
<212> TYPE: DNA
<213> ORGANISM: Artificial Sequence
<220> FEATURE:
<223> OTHER INFORMATION: Nhe site upstream of the KS at position 7570

<400> SEQUENCE: 1
gctagcgagc cgatc                                                    15

<210> SEQ ID NO 2
<211> LENGTH: 15
<212> TYPE: DNA
<213> ORGANISM: Artificial Sequence
<220> FEATURE:
<223> OTHER INFORMATION: Nhe site upstream of the KS at position 28710

<400> SEQUENCE: 2
gctagcgacc cgatc                                                    15

<210> SEQ ID NO 3
<211> LENGTH: 18
<212> TYPE: PRT
<213> ORGANISM: Artificial Sequence
<220> FEATURE:
<223> OTHER INFORMATION: Intra-polypeptide linker

<400> SEQUENCE: 3

Gly Gly Ala Thr Gly Ala Glu Gln Ala Ala Pro Ala Thr Thr Ala Pro
  1               5                  10                  15

Val Asp

<210> SEQ ID NO 4
<211> LENGTH: 18
<212> TYPE: PRT
<213> ORGANISM: Artificial Sequence
<220> FEATURE:
<223> OTHER INFORMATION: Intra-polypeptide linker

<400> SEQUENCE: 4

Val Gly Asp Ala Asp Gln Ala Ala Val Arg Val Val Gly Ala Ala Asp
  1               5                  10                  15

Glu Ser

<210> SEQ ID NO 5
<211> LENGTH: 21
<212> TYPE: PRT
<213> ORGANISM: Artificial Sequence
<220> FEATURE:
<223> OTHER INFORMATION: Intra-polypeptide linker

<400> SEQUENCE: 5

Val Gly Ala Ala Glu Ala Glu Gln Ala Pro Ala Leu Val Arg Glu Val
  1               5                  10                  15

Pro Lys Asp Ala Asp
             20

<210> SEQ ID NO 6
<211> LENGTH: 17
<212> TYPE: PRT
<213> ORGANISM: Artificial Sequence

```
<220> FEATURE:
<223> OTHER INFORMATION: Intra-polypeptide linker

<400> SEQUENCE: 6

Phe Gly Ser Ala Ala Asn Arg Pro Ala Glu Ile Gly Thr Ala Ala Ala
 1               5                  10                  15

Glu

<210> SEQ ID NO 7
<211> LENGTH: 17
<212> TYPE: PRT
<213> ORGANISM: Artificial Sequence
<220> FEATURE:
<223> OTHER INFORMATION: Intra-polypeptide linker

<400> SEQUENCE: 7

Leu Gly Glu Arg Pro Ala Ala Pro Ala Pro Val Thr Arg Asp Val Ser
 1               5                  10                  15

Asp

<210> SEQ ID NO 8
<211> LENGTH: 19
<212> TYPE: PRT
<213> ORGANISM: Artificial Sequence
<220> FEATURE:
<223> OTHER INFORMATION: Intra-polypeptide linker

<400> SEQUENCE: 8

Gly Glu Thr Val Ala Gly Ala Pro Ala Thr Pro Val Thr Thr Val Ala
 1               5                  10                  15

Asp Ala Gly

<210> SEQ ID NO 9
<211> LENGTH: 21
<212> TYPE: PRT
<213> ORGANISM: Artificial Sequence
<220> FEATURE:
<223> OTHER INFORMATION: Intra-polypeptide linker

<400> SEQUENCE: 9

Glu Leu Phe Thr Gly Glu Asn Pro Ala Pro Val Arg Gly Pro Val Ser
 1               5                  10                  15

Ala Val Gly Gln Asp
            20

<210> SEQ ID NO 10
<211> LENGTH: 21
<212> TYPE: PRT
<213> ORGANISM: Artificial Sequence
<220> FEATURE:
<223> OTHER INFORMATION: Intra-polypeptide linker

<400> SEQUENCE: 10

Glu Leu Phe Thr Gly Glu Asn Pro Ala Pro Val Arg Gly Pro Val Ser
 1               5                  10                  15

Val Val Gly Gln Asp
            20

<210> SEQ ID NO 11
<211> LENGTH: 20
<212> TYPE: PRT
<213> ORGANISM: Artificial Sequence
<220> FEATURE:
<223> OTHER INFORMATION: Intra-polypeptide linker
```

```
<400> SEQUENCE: 11

Glu Leu Phe Thr Gly Glu Asn Pro Ala Pro Val Arg Gly Pro Val Ser
1               5                   10                  15

Ala Gly Gln Asp
            20

<210> SEQ ID NO 12
<211> LENGTH: 30
<212> TYPE: PRT
<213> ORGANISM: Artificial Sequence
<220> FEATURE:
<223> OTHER INFORMATION: N-Terminal Inter-polypeptide linker

<400> SEQUENCE: 12

Val Thr Asp Ser Glu Lys Val Ala Glu Tyr Leu Arg Arg Ala Thr Leu
1               5                   10                  15

Asp Leu Arg Ala Ala Arg Gln Arg Ile Arg Glu Leu Glu Ser
            20                  25                  30

<210> SEQ ID NO 13
<211> LENGTH: 38
<212> TYPE: PRT
<213> ORGANISM: Artificial Sequence
<220> FEATURE:
<223> OTHER INFORMATION: N-Terminal Inter-polypeptide linker

<400> SEQUENCE: 13

Met Ser Gly Asp Asn Gly Met Thr Glu Glu Lys Leu Arg Arg Tyr Leu
1               5                   10                  15

Lys Arg Thr Val Thr Glu Leu Asp Ser Val Thr Ala Arg Leu Arg Glu
            20                  25                  30

Val Glu His Arg Ala Gly
        35

<210> SEQ ID NO 14
<211> LENGTH: 34
<212> TYPE: PRT
<213> ORGANISM: Artificial Sequence
<220> FEATURE:
<223> OTHER INFORMATION: N-Terminal Inter-polypeptide linker

<400> SEQUENCE: 14

Met Ser Ala Pro Asn Glu Gln Ile Val Asp Ala Leu Arg Ala Ser Leu
1               5                   10                  15

Lys Glu Asn Val Arg Leu Gln Gln Glu Asn Ser Ala Leu Ala Ala Ala
            20                  25                  30

Ala Ala

<210> SEQ ID NO 15
<211> LENGTH: 34
<212> TYPE: PRT
<213> ORGANISM: Artificial Sequence
<220> FEATURE:
<223> OTHER INFORMATION: N-Terminal Inter-polypeptide linker

<400> SEQUENCE: 15

Val Ser Ala Ser Tyr Glu Lys Val Val Glu Ala Leu Arg Lys Ser Leu
1               5                   10                  15

Glu Glu Val Gly Thr Leu Lys Lys Arg Asn Arg Gln Leu Ala Asp Ala
            20                  25                  30

Ala Gly
```

```
<210> SEQ ID NO 16
<211> LENGTH: 33
<212> TYPE: PRT
<213> ORGANISM: Artificial Sequence
<220> FEATURE:
<223> OTHER INFORMATION: N-Terminal Inter-polypeptide linker

<400> SEQUENCE: 16

Val Ala Asp Glu Gly Gln Leu Arg Asp Tyr Leu Lys Arg Ala Ile Ala
 1               5                  10                  15

Asp Ala Arg Asp Ala Arg Thr Arg Leu Arg Glu Val Glu Glu Gln Ala
            20                  25                  30

Arg

<210> SEQ ID NO 17
<211> LENGTH: 30
<212> TYPE: PRT
<213> ORGANISM: Artificial Sequence
<220> FEATURE:
<223> OTHER INFORMATION: N-Terminal Inter-polypeptide linker

<400> SEQUENCE: 17

Met Ala Thr Asp Glu Lys Leu Leu Lys Tyr Leu Lys Arg Val Thr Ala
 1               5                  10                  15

Glu Leu His Ser Leu Arg Lys Gln Gly Ala Arg His Ala Asp
            20                  25                  30

<210> SEQ ID NO 18
<211> LENGTH: 32
<212> TYPE: PRT
<213> ORGANISM: Artificial Sequence
<220> FEATURE:
<223> OTHER INFORMATION: N-Terminal Inter-polypeptide linker

<400> SEQUENCE: 18

Met Arg Glu Asp Gln Leu Leu Asp Ala Leu Arg Lys Ser Val Lys Glu
 1               5                  10                  15

Asn Ala Arg Leu Arg Lys Ala Asn Thr Ser Leu Arg Ala Ala Met Asp
            20                  25                  30

<210> SEQ ID NO 19
<211> LENGTH: 33
<212> TYPE: PRT
<213> ORGANISM: Artificial Sequence
<220> FEATURE:
<223> OTHER INFORMATION: N-Terminal Inter-polypeptide linker

<400> SEQUENCE: 19

Met Pro Glu Gln Asp Lys Val Val Glu Tyr Leu Arg Trp Ala Thr Ala
 1               5                  10                  15

Glu Leu His Thr Thr Arg Ala Lys Leu Glu Ala Leu Ala Ala Ala Asn
            20                  25                  30

Thr

<210> SEQ ID NO 20
<211> LENGTH: 31
<212> TYPE: PRT
<213> ORGANISM: Artificial Sequence
<220> FEATURE:
<223> OTHER INFORMATION: N-terminal linker of M3

<400> SEQUENCE: 20
```

-continued

```
Met Thr Asp Ser Glu Lys Val Ala Glu Tyr Leu Arg Arg Ala Thr Leu
 1               5                  10                  15

Asp Leu Arg Ala Ala Arg Gln Arg Ile Arg Glu Leu Glu Ser Asp
                20                  25                  30
```

<210> SEQ ID NO 21
<211> LENGTH: 25
<212> TYPE: DNA
<213> ORGANISM: Artificial Sequence
<220> FEATURE:
<223> OTHER INFORMATION: primer

<400> SEQUENCE: 21
actagtaggc tgttcgcggc ctcac        25

<210> SEQ ID NO 22
<211> LENGTH: 24
<212> TYPE: DNA
<213> ORGANISM: Artificial Sequence
<220> FEATURE:
<223> OTHER INFORMATION: primer

<400> SEQUENCE: 22
gggaattcag gtcctctccc ccgc         24

<210> SEQ ID NO 23
<211> LENGTH: 23
<212> TYPE: DNA
<213> ORGANISM: Artificial Sequence
<220> FEATURE:
<223> OTHER INFORMATION: primer

<400> SEQUENCE: 23
ccatatggtg gtcgaccggc tcg          23

<210> SEQ ID NO 24
<211> LENGTH: 24
<212> TYPE: DNA
<213> ORGANISM: Artificial Sequence
<220> FEATURE:
<223> OTHER INFORMATION: primer

<400> SEQUENCE: 24
gaattcctac aggtcctctc cccc         24

METHODS OF MAKING POLYKETIDES USING HYBRID POLYKETIDE SYNTHASES

CROSS-REFERENCE TO RELATED APPLICATIONS

This application is a continuation-in-part U.S. Ser. No. 09/500,747, filed 9 Feb. 2000 and now U.S. Pat. No. 6,753,173 which claims benefit of Provisional Application 60/119,363, filed 9 Feb. 1999. The present application further claims benefit of U.S. Provisional Applications 60/272,985 and 60/272,987, both filed 2 Mar. 2001. Each of these documents is incorporated herein by reference.

STATEMENT OF RIGHTS TO INVENTIONS MADE UNDER FEDERALLY SPONSORED RESEARCH

The invention herein was made, at least in part, based on support by grants CA-66736, GM-22172, and GM-22176 from the National Institutes of Health, and grant BES-9806774 from the National Science Foundation. The U.S. government may have certain rights in the invention.

TECHNICAL FIELD

The invention is directed to facilitating usage by polyketide synthase modules of nascent polyketide chains. Specifically, the invention concerns including intermodule and intramodule linkers in constructions for synthesis of desired polyketides. More specifically, the invention concerns the effects of protein-protein interactions and enzyme-substrate interactions in the channeling of intermediates between polyketide synthase modules.

BACKGROUND OF THE INVENTION

Polyketides are a class of compounds synthesized from 2-carbon units through a series of condensations and subsequent modifications. Polyketides occur in many types of organisms, including fungi and mycelial bacteria, in particular, the actinomycetes. Polyketides are biologically active molecules with a wide variety of structures, and the class encompasses numerous compounds with diverse activities. Tetracycline, erythromycin, epothilone, FK-506, FK-520, narbomycin, picromycin, rapamycin, spinocyn, and tylosin are examples of polyketides. Given the difficulty in producing polyketide compounds by traditional chemical methodology, and the typically low production of polyketides in wild-type cells, there has been considerable interest in finding improved or alternate means to produce polyketide compounds.

The biosynthetic diversity of polyketides is generated by repetitive condensations of simple monomers by polyketide synthase (PKS) enzymes that mimic fatty acid synthases. For instance, the deoxyerythronolide-B synthase catalyzes the chain extension of a primer with several methylmalonyl coenzyme A (MeMalCoA) extender units to produce the erythromycin core.

The cloning, analysis, and recombinant DNA technology of genes that encode PKS enzymes allows one to manipulate a known PKS gene cluster either to produce the polyketide synthesized by that PKS at higher levels than occur in nature or in hosts that otherwise do not produce the polyketide. The technology also allows one to produce molecules that are structurally related to, but distinct from, the polyketides produced from known PKS gene clusters. See, e.g., PCT publication Nos. WO 93/13663; 95/08548; 96/40968; 97/02358; 98/27203; and 98/49315; U.S. Pat. Nos. 4,874,748; 5,063,155; 5,098,837; 5,149,639; 5,672,491; 5,712,146; 5,830,750; and 5,843,718; and Fu, et al., 1994, *Biochemistry* 33: 9321–9326; McDaniel, et al., 1993, *Science* 262: 1546–1550; and Rohr, 1995, *Angew. Chem. Int. Ed. Engl.* 34(8): 881–888, each of which is incorporated herein by reference.

PKSs catalyze the biosynthesis of polyketides through repeated, decarboxylative Claisen condensations between acylthioester building blocks. The building blocks used to form complex polyketides are typically acylthioesters, such as acetyl, butyryl, propionyl, malonyl, hydroxymalonyl, methylmalonyl, and ethylmalonyl CoA. Two major types of PKS enzymes are known; these differ in their composition and mode of synthesis of the polyketide synthesized. These two major types of PKS enzymes are commonly referred to as Type I or "modular" and Type II "iterative" PKS enzymes.

The present invention concerns modular PKS. In the Type I or modular PKS enzyme group, a set of separate catalytic active sites (each active site is termed a "domain", and a set thereof is termed a "module") exists for each cycle of carbon chain elongation and modification in the polyketide synthesis pathway. The typical modular PKS is composed of several large polypeptides, which can be segregated from amino to carboxy terminii into a loading module, multiple extender modules, and a releasing (or thioesterase) domain. The PKS enzyme known as 6-deoxyerythronolide B synthase (DEBS) is a typical Type I PKS. In DEBS, there is a loading module, six extender modules, and a thioesterase (TE) domain. The loading module, six extender modules, and TE of DEBS are present on three separate proteins (designated DEBS-1, DEBS-2, and DEBS-3, with two extender modules per protein). Each of the DEBS polypeptides is encoded by a separate open reading frame (ORF) or gene; these genes are known as eryAI, eryAII, and eryAIII. See FIG. 1. There is considerable interest in the genetic and chemical reprogramming of modular PKSs (see, e.g., Khosla, 1997, *Chem. Rev.* 97:2577–2590, and Staunton, et al., 1997, *Chem. Rev.* 2611–2629, each of which is incorporated herein by reference).

Generally, the loading module is responsible for binding the first building block used to synthesize the polyketide and transferring it to the first extender module. The loading module of DEBS consists of an acyltransferase (AT) domain and an acyl carrier protein (ACP) domain. Another type of loading module utilizes an inactivated KS, an AT, and an ACP. This inactivated KS is in some instances called $KS^Q$, where the superscript letter is the abbreviation for the amino acid, glutamine, that is present instead of the active site cysteine required for ketosynthase activity. In other PKS enzymes, including the FK-520 PKS, the loading module incorporates an unusual starter unit and is composed of a CoA ligase activity domain. In any event, the loading module recognizes a particular acyl-CoA (usually acetyl or propionyl but sometimes butyryl) and transfers it as a thiol ester to the ACP of the loading module.

The AT on each of the extender modules recognizes a particular extender-CoA (malonyl or alpha-substituted malonyl, i.e., methylmalonyl, ethylmalonyl, and hydroxymalonyl) and transfers it to the ACP of that extender module to form a thioester. Each extender module is responsible for accepting a compound from a prior module, binding a building block, attaching the building block to the compound from the prior module, optionally performing one or more additional functions, and transferring the resulting compound to the next module. The transfer into a module is mediated by the KS domain which is upstream of the remaining catalytic domains. The additional functions are performed by enzymes which comprise a ketoreductase (KR) which reduces the carbonyl group generated from the condensation to an alcohol, a dehydratase (DH) which converts the alcohol to a double bond, and an enoyl reductase (ER) which reduces the double bond to a single bond. These catalytic domains appear to be immediately adjacent and not separated by any linking sequences. Collectively, they can be called "beta-carbonyl modifying" domains. Thus, a particular module may contain none of these activities, only KR, or KR+DH, or KR+DH+ER. Thus, the order of domains from the N-terminus of a particular module is KS, AT, beta-carbonyl modifying domains (if present), ACP. The order, N→C of the beta-carbonyl modifying enzymes is DH ER KR.

Thus, each extender module of a modular PKS contains zero, one, two, or three enzymes that modify the beta-carbon of the growing polyketide chain downstream of the AT catalytic domain. A typical (non-loading) minimal Type I PKS extender module is exemplified by extender module 3 of DEBS, which contains only a KS domain, an AT domain, and an ACP domain. The next extender module, module 4, contains all three beta-carbonyl modifying enzymes. (The beta-carbonyl modifying enzymes effect such modification on the extender unit that has been added by the previous module.)

Once the PKS is primed with acyl- and malonyl-ACPs, the acyl group of the loading module migrates to form a thiol ester (trans-esterification) at the KS of the first extender module; at this stage, extender module one possesses an acyl-KS adjacent to a malonyl (or substituted malonyl) ACP. The acyl group derived from the loading module is then covalently attached to the alpha-carbon of the malonyl group to form a carbon-carbon bond, driven by concomitant decarboxylation, and generating a new acyl-ACP that has a backbone two carbons longer than the loading building block (elongation or extension).

After traversing the final extender module, the polyketide encounters a releasing domain that cleaves the polyketide from the PKS and typically cyclizes the polyketide. For example, final synthesis of 6-dEB is regulated by a TE domain located at the end of extender module six. In the synthesis of 6-dEB, the TE domain catalyzes cyclization of the macrolide ring by formation of an ester linkage. In FK-506, FK-520, rapamycin, and similar polyketides, the ester linkage formed by the TE activity is replaced by a linkage formed by incorporation of a pipecolate acid residue. The enzymatic activity that catalyzes this incorporation for the rapamycin enzyme is known as RapP, encoded by the rapP gene. The polyketide can be modified further by tailoring enzymes; these enzymes add carbohydrate groups or methyl groups, or make other modifications, i.e., oxidation or reduction, on the polyketide core molecule. For example, 6-dEB is hydroxylated at C6 and C12 and glycosylated at C3 and C5 in the synthesis of erythromycin A.

In PKS polypeptides, the regions that encode enzymatic activities (domains) are separated by linker or "scaffold"-encoding regions. These scaffold regions encode amino acid sequences that space the domains at the appropriate distances and in the correct order. Thus, the linker regions of a PKS protein collectively can be considered to encode a scaffold into which the various domains (and thus modules) are placed in a particular order and spatial arrangement. Generally, this organization permits PKS catalytic domains of different or identical substrate specificities to be substituted (usually at the DNA level) between PKS enzymes by various available methodologies. Thus, there is considerable flexibility in the design of new PKS enzymes with the result that known polyketides can be produced more effectively, and novel polyketides useful as pharmaceuticals or for other purposes can be made.

PCT publication WO 98/49315, the contents of which are incorporated herein by reference, describes an approach for modifying the enzymatic activities included within modules of a PKS by maintaining the scaffolding intact but replacing catalytic domains with different catalytic domains. U.S. Ser. No. 09/346,860 filed 2 Jul. 1999 and now U.S. Pat. No. 6,221,641 and the corresponding PCT publication WO 00/01838, also filed on that date, and incorporated herein by reference describe alternative methods by altering the hypervariable region of the AT domains so as to alter the specificity for an extender unit and alteration of the KS domains to control stereochemistry. The present invention takes advantage of the approach of manipulating modules so that the catalytic activities of an entire module are placed in the appropriate sequence to construct a desired polyketide. The ability to utilize this approach depends on effecting an appropriate means for the module to incorporate a growing polyketide chain, which involves assuring that an appropriate linker region is included. Since the filing of the provisional application from which the present application claims priority, a related paper has been published by Ranganathan, A., et al., Chem. & Biol. (1999) 6:731–741. In this paper, intrapolypeptide linkages are fortuitously supplied to chimeric modules by including the KS region of the native downstream module in a chimera between the corresponding upstream module and the portions downstream of the KS domain in a heterologous module. Alternatively, the downstream module will include the ACP catalytic domain of the native upstream module fused to the remainder of a heterologous module upstream in the chimera.

Background Information

The following articles provide information relating to the invention: Aparicio, J. F., et al., (1996) Gene 169, 9–16; Cortes, J., et al., (1990) Nature 348, 176–178; Donadio, S., et al., (1991) Science 252, 675–679; Gokhale, R. S., et al., (2000) Curr. Opin. Chem. Biol. 4, 22–27.

Abbreviations 6-dEB: 6-deoxyerythronolide B; ACP: acyl carrier protein; AT: acyltransferase; DEBS: 6-deoxyerythronolide B synthase; DH: dehydratase; ER: enoylreductase; KR: ketoreductase; KS: ketosynthase; NAC: N-acetylcysteamine; NRPS: nonribosomal peptide synthetase; PCP: peptidyl carrier protein; PKS: polyketide synthase; ACP: acyl carrier protein; ER: enoylreductase; LDD: loading didomain; TE: thioesterase; M2: module 2 of DEBS; M2(4): module 2 with C-terminal linker from module 4; M3+TE: module 3 fused to thioesterase; (5)M3+TE: module 3 with N-terminal linker from module 5; M2:M3: complex of module 2 and module 3; and NDK: (2S,3R)-2-methyl-3-hydroxypentanoic acid diketide.

DISCLOSURE OF THE INVENTION

The invention is directed to an efficient method for constructing an arbitrarily chosen polyketide synthase, and therefore a desired polyketide, by manipulating entire modules of Type I polyketide synthases. The invention enables this approach by providing the modules with the appropriate "lead-in" or linker sequence to the ketosynthase (KS). Applicants have discovered that the appropriate linker between modules is required upstream of the relevant KS in order to permit the module to accept the nascent polyketide chain, and, in the case of intermolecular transfer, appropriate pairing of N-terminal and C-terminal regions assures the appropriate transfer. The nature of this linker varies depending on whether the module is covalently linked downstream from another module, or whether it forms the N-terminus of the polypeptide.

Thus, in one aspect, the invention is directed to a method to construct a functional polyketide synthase which method comprises providing each module contained in the desired polyketide synthase with an appropriate intrapolypeptide linker (RAL) when said module is downstream in the same polypeptide from a module derived from a different PKS and with an appropriate interpolypeptide linker (ERL) when the module is derived from a PKS where the module is the N-terminal module of a polypeptide. If the module at the N-terminus of a polypeptide is to accept a nascent polyketide chain from an upstream module, the interpolypeptide linker needs to include the appropriate amino acid sequence at the C-terminus of the module donating the nascent chain.

In describing a "module" being provided with linker(s) the term "module" refers to the functional portions extending approximately from the N-terminus of the KS catalytic region to the C-terminus of the ACP—i.e., excludes the linker portions otherwise considered a portion of the module.

As further described below, any order of modules of desired specificity can be assured by providing the appropriate linkers either intermolecularly or intramolecularly. Thus, the polyketide synthase can be assembled from individual modules by providing the appropriate linkers to assure that the polyketide chain will be passed in the correct sequence from one module to the next and by assembling these modules either by directly providing the polypeptides containing them or by co-expressing nucleotide sequences and coding them in a host cell.

In other aspects, the invention is directed to materials and compositions useful in carrying out the method, in particular to isolated DNA fragments which contain the appropriate intrapolypeptide and interpolypeptide linkers. The invention also relates to methods to construct functional polyketide synthases from libraries of modules and to polyketides prepared by supplying appropriate substrates to reconstructed polyketide synthases. The polyketides thus prepared can be "tailored" using either isolated enzymes or feeding the polyketides to an organism containing these enzymes to convert them to anti-infectives or compounds of other activities such as motolides by such post-polyketide modifications as hydroxylation and glycosylation. The ketides or ketolides or their modified forms can also be further derivatized using chemical synthetic methods.

In other apects, the invention is directed towards the C- and N-terminal ends of adjacent PKS polypeptides capped by peptides of 20–40 residues. Mismatched sequences abolish intermodular chain transfer without affecting the activity of individual modules, whereas matched sequences can facilitate the channeling of intermediates between ordinarily non-consecutive modules.

In yet another aspect, the invention is directed towards the role of protein-protein interactions in substrate channeling and more specifically to assays or methods to assess the steady-state kinetic parameters of individual DEBS modules when primed in a channeling modes versus a diffusive mode. The diffusive process precludes the involvement of the covalent, substrate channeling mechanism by which enzyme-bound intermediates are directly transferred from one module to the next in a multi-modular PKS. These methods can be used to quantify the kinetic benefit of linker-mediated substrate channeling in a modular PKS.

In another aspect, the invention is directed towards the ability of a synthetic peptide to inhibit tetraketide production. For example, a peptide corresponding to the N-terminal linker of module 3 was synthesized and shown to inhibit the formation of tetraketide lactone 2 (as shown in FIG. 6) in the presence of M2 and M3+TE in a concentration-dependent manner.

BRIEF DESCRIPTION OF THE DRAWINGS

FIG. 3 shows sequences of intrapolypeptide and interpolypetide linkers derived from various Type I PKS.

FIG. 6 is a schematic diagram of the interpolypeptide transfer with matched and mismatched linker pairs.

FIG. 13 presents a comparison of the $k_{cat}/K_M$ values ($min^{-1}$ $mM^{-1}$) of the two syn-diketides when presented as acyl-ACP substrates (4a and 4b) vs when presented as NAC-thioesters (2a and 2b).

FIG. 14 presents a comparison of the $k_{cat}$ values ($min^{-1}$) of the four diketides when presented as acyl-ACP substrates (4a–d) vs when presented as NAC-thioesters (2a–d).

FIG. 17 is a schematic of matched and mismatched linker pairs at intermodular interfaces.

FIG. 18 is a schematic illustrating the channeling of intermediates to unnatural recipient modules.

FIG. 20 is table summarizing the substrates and enzymes used to study substrate transfer from a donor to a recipient module.

DETAILED DESCRIPTION OF THE DRAWINGS

Figure 1:
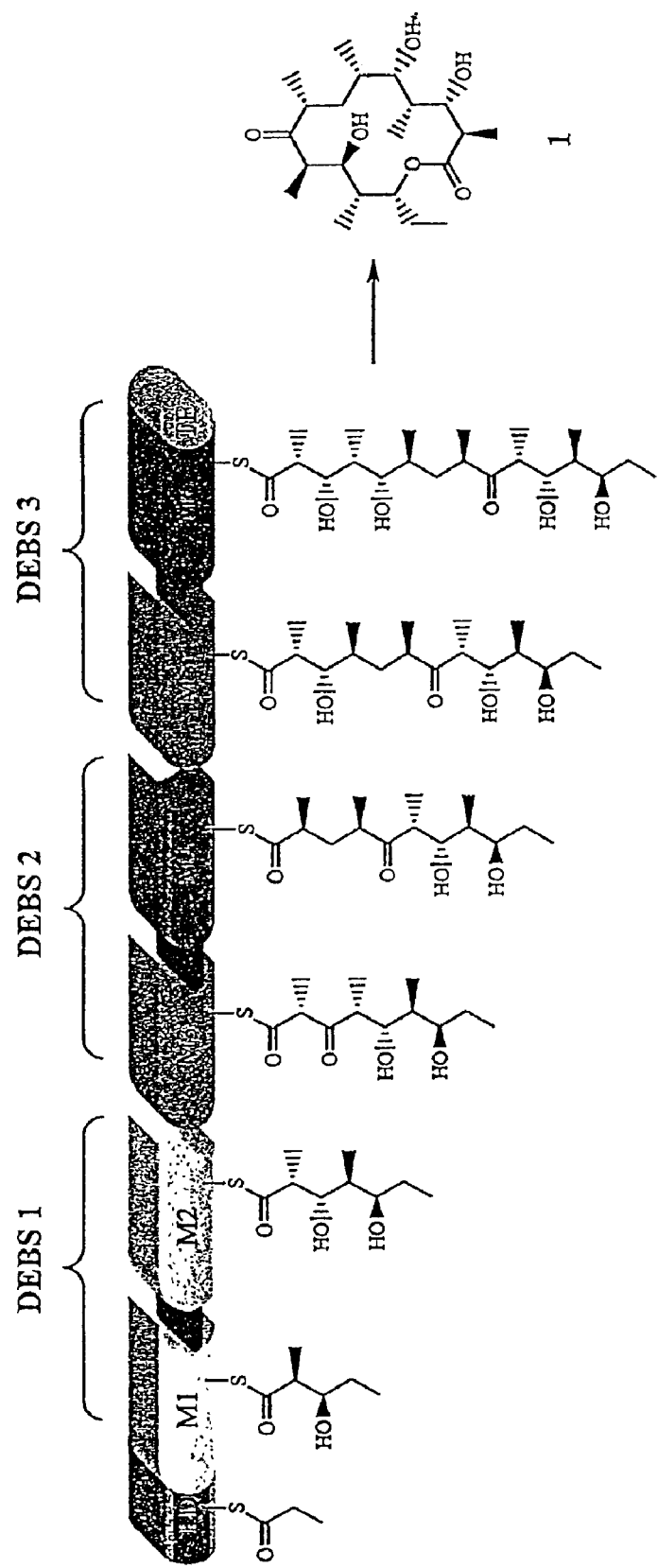
FIG. 1 is a diagram of erythromycin PKS which forms 6-dEB.

FIG. 1 is a diagram of the erythromycin PKS which forms 6-dEB, the core precursor of erythromycin. As shown, the PKS is comprised of three proteins, DEBS-1, DEBS-2 and DEBS-3 which are encoded by three genes, commonly called eryAI, eryAII and eryAIII.

Figure 2:
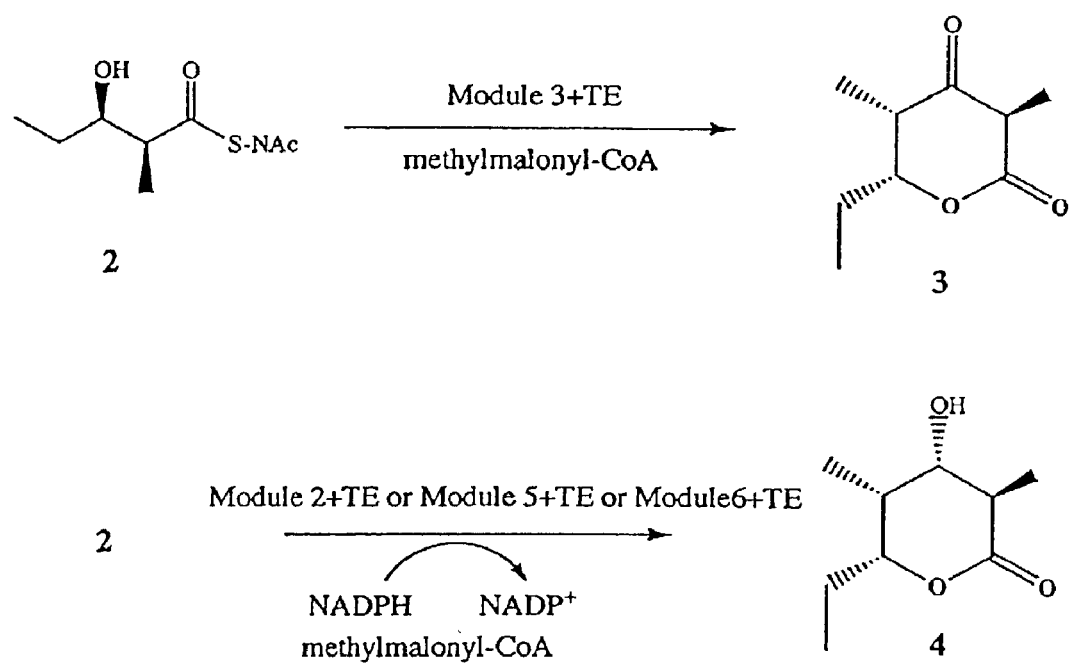
FIG. 2 shows the conversion of a diketide thioester to the triketides corresponding to those produced by DEBS-1 of the erythromycin PKS.

FIG. 2 shows the conversion of a diketide thioester to the triketides corresponding to those produced by DEBS-1 of the erythromycin PKS.

FIG. 3 shows the structures of intrapolypeptide linkers and the N-terminal portions of interpolypeptide linkers (SEQ ID NOS:3–19) derived from various Type I PKS.

Figure 4:
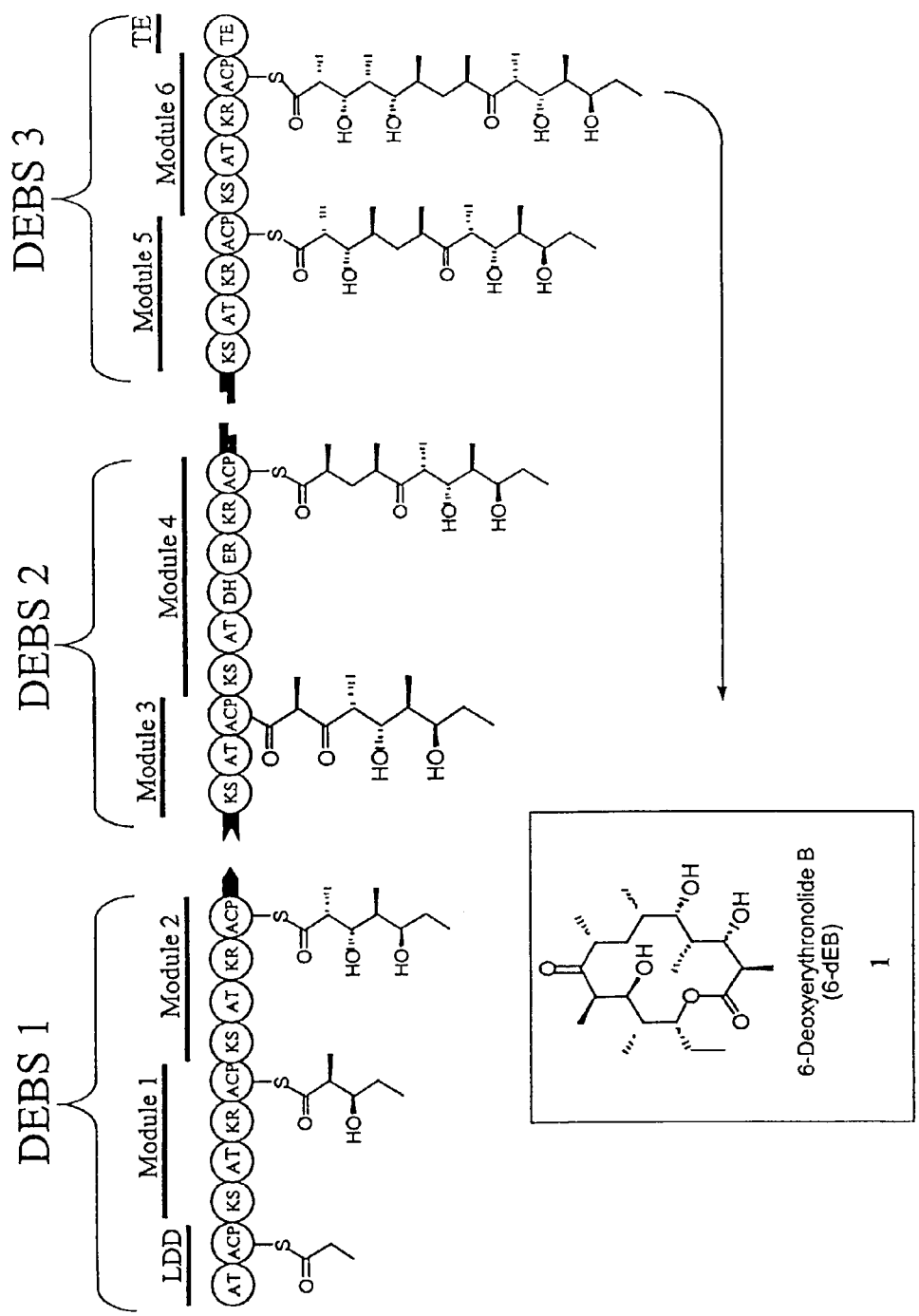
FIG. 4 is a schematic diagram of the biosynthesis of 6-dEB by 6-deoxyerythronolide B synthase.

FIG. 4 is a schematic diagram of the biosynthesis of 6-dEB by 6-deoxyerythronolide B synthase. Each polypeptide, DEBS1, DEBS2, and DEBS3, contains two modules, and each module comprises a set of active site domains responsible for addition and modification of an extender unit. The short "linker" regions are located at the N- and C-termini; their shapes exemplify the complementarity demonstrated by each pair.

Figure 5:
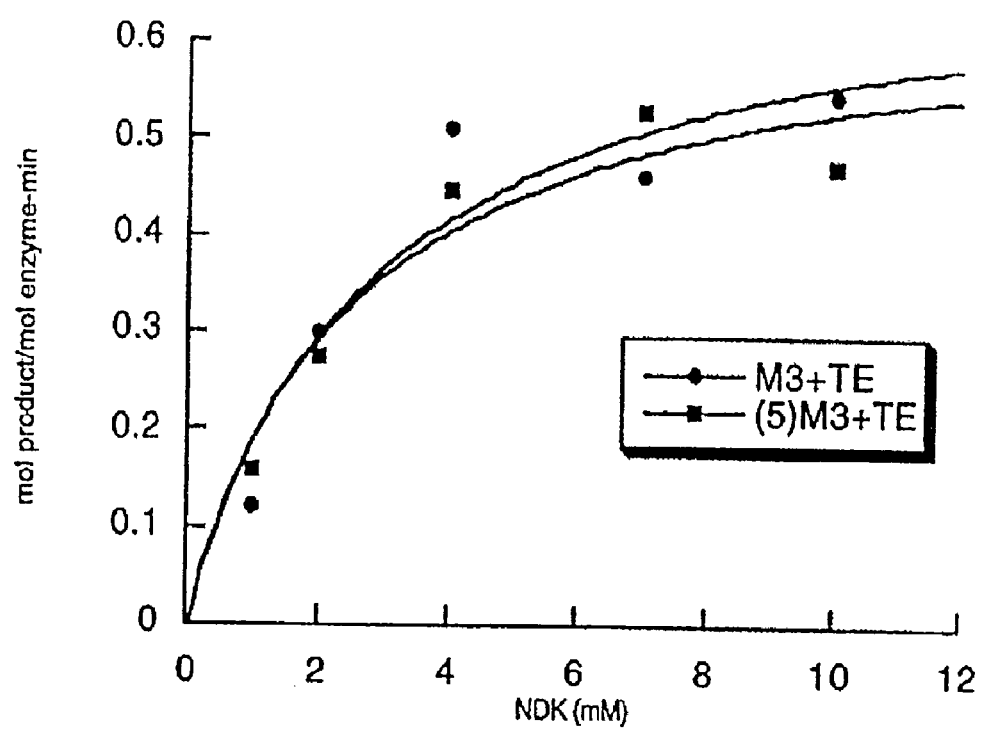
FIG. 5 presents a velocity vs. NDK (mM) plot showing the fit of the Michaelis-Menten equation for M3+TE and (5)M3+TE alone.

FIG. 5 presents a velocity vs. NDK (mM) plot showing the fit of the Michaelis-Menten equation for M3+TE and (5)M3+TE alone. The nearly identical $k_{cat}$ values of 0.71 and 0.68 $min^{-1}$ and $K_M$ values of 2.8 and 2.5 $\mu$M demonstrate the interchangeability of the linkers for individual modules.

FIG. 6 presents a schematic diagram of the interpolypeptide transfer with matched and mismatched linker pairs: (A) wild-type linker pair, M2 C-terminus+M3 N-terminus; (B) mismatched pair, M2 C-terminus+M5 N-terminus; (C) mismatched pair, M4 C-terminus+M3 N-terminus; (D) matched pair, M4 C-terminus+M5 N-terminus.

Figure 7:
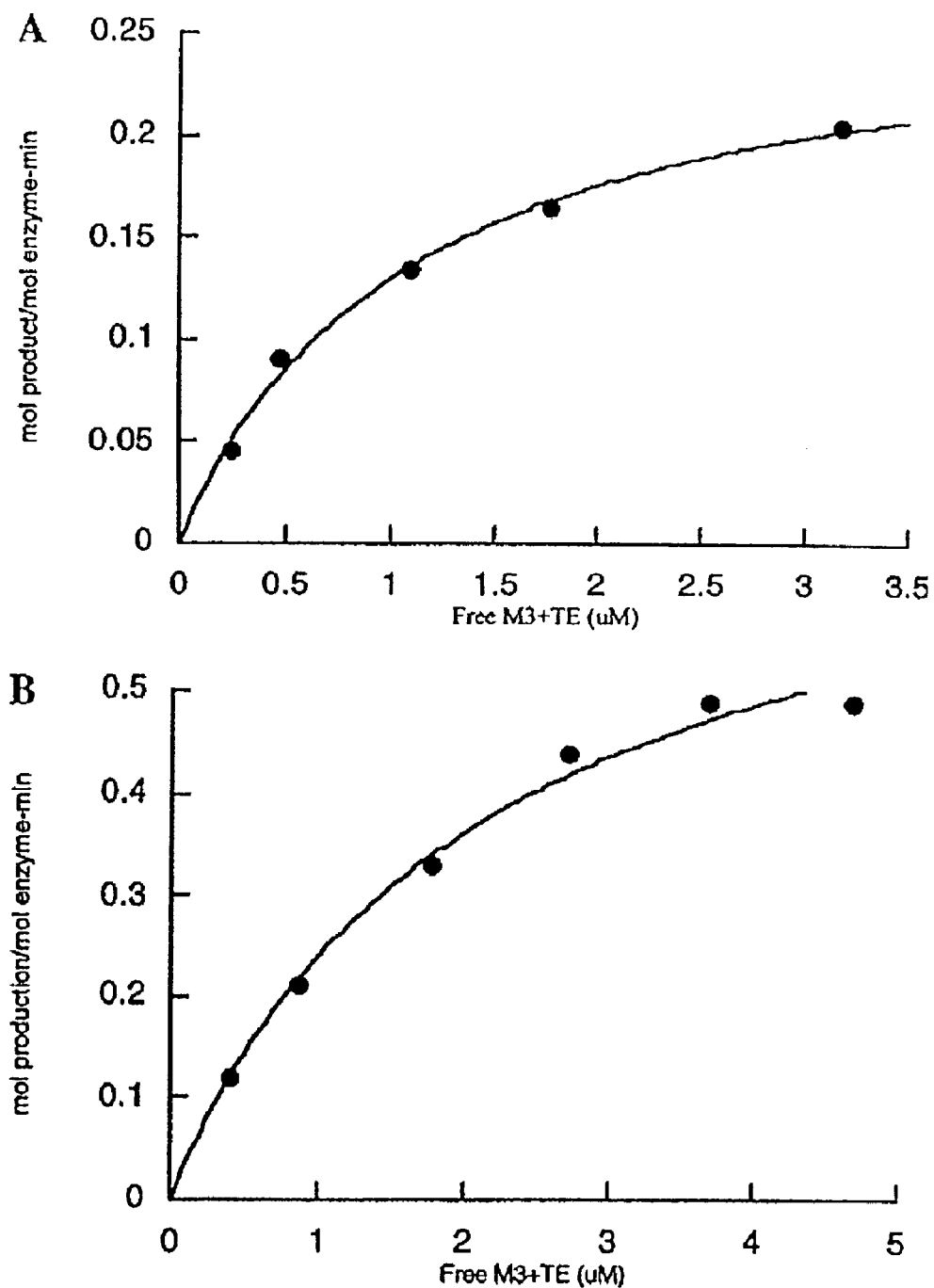
FIG. 7 provides saturation curves of (A) M2 with M3+TE and (B) M2(4) with (5)M3+TE.

FIG. 7 provides saturation curves of (A) M2 with M3+TE and (B) M2(4) with (5)M3+TE showing the effect of increasing M3 concentration on the overall rate of turnover. From these plots, the saturating rates of 0.27 and 0.74 $min^{-1}$ were determined, as were the $K_D$ values of 1.1 and 2.1 $\mu$M.

Figure 8:
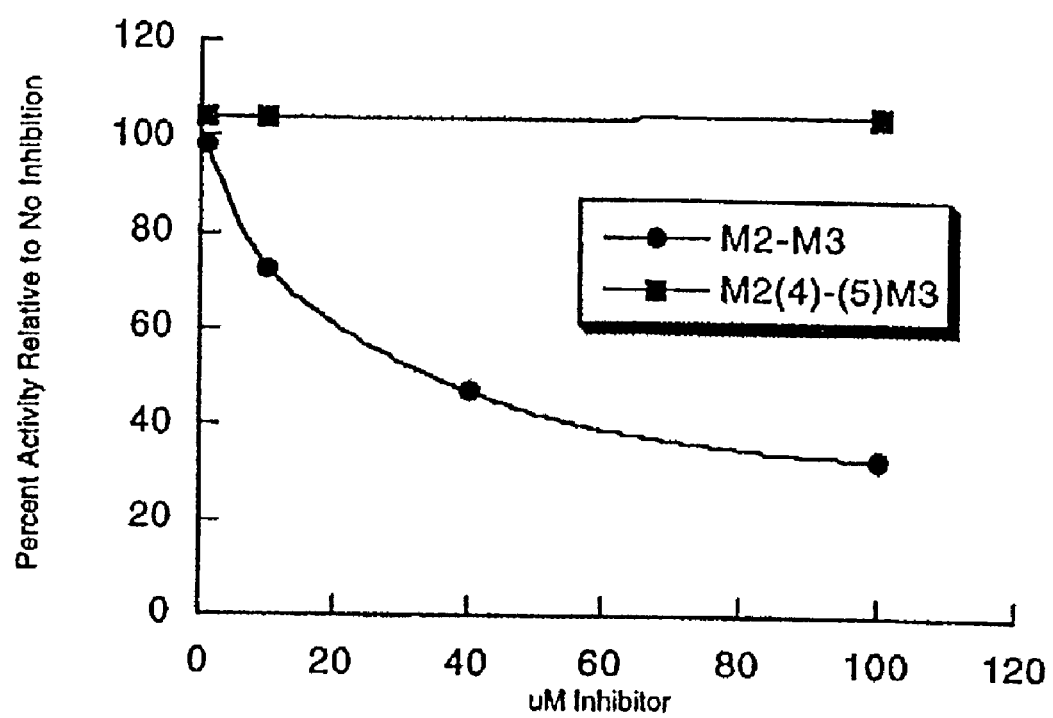
FIG. 8 shows selective inhibition by a synthetic peptide mimic of the N-terminal linker of M3.

FIG. 8 shows selective inhibition by the synthetic peptide mimic of the N-terminal linker of M3. The linker lowered the overall rate of tetraketide production in a dose-dependent fashion for the transfer using the M2-M3 linker pair. However, it demonstrated no such effect when tetraketide production depended upon interpolypeptide transfer using the M4-M5 linker pair.

Figure 9:
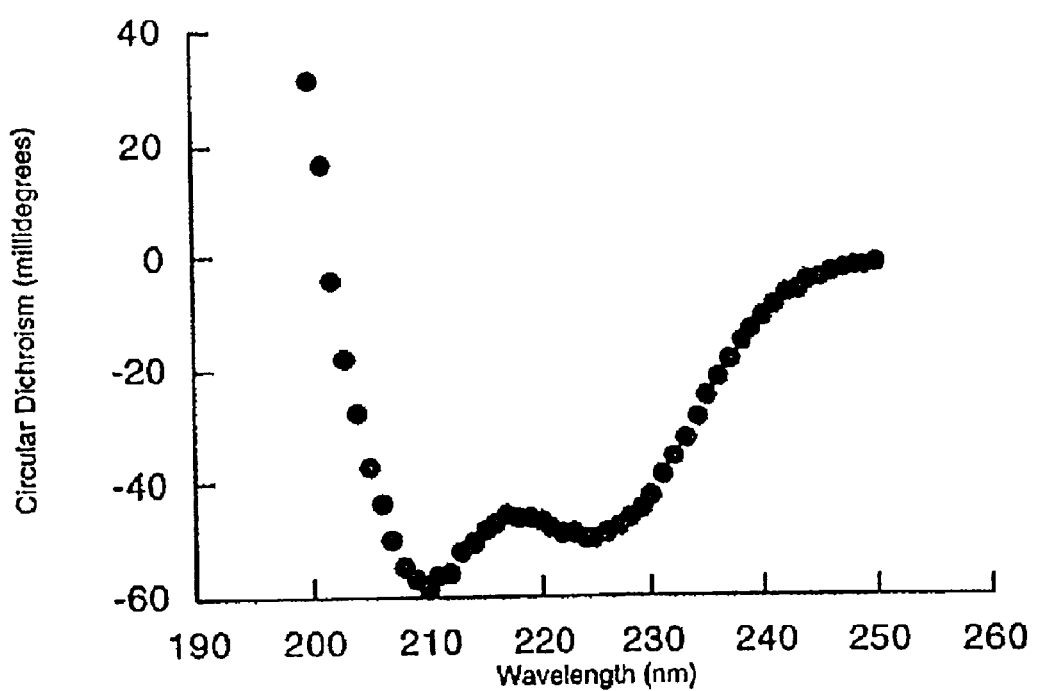
FIG. 9 provides the CD spectrum of a peptide mimic showing the minima at 208 and 222 nm indicative of α-helical character.

FIG. 9 provides the CD spectrum of the peptide mimic showing the minima at 208 and 222 nm indicative of α-helical character. Though only ca. 50% helical, its structural features correlate with the expected coiled-coil motif. Furthermore, its ability to selectively inhibit interpolypeptide transfer verified some recognition ability of the mimic.

Figure 10:
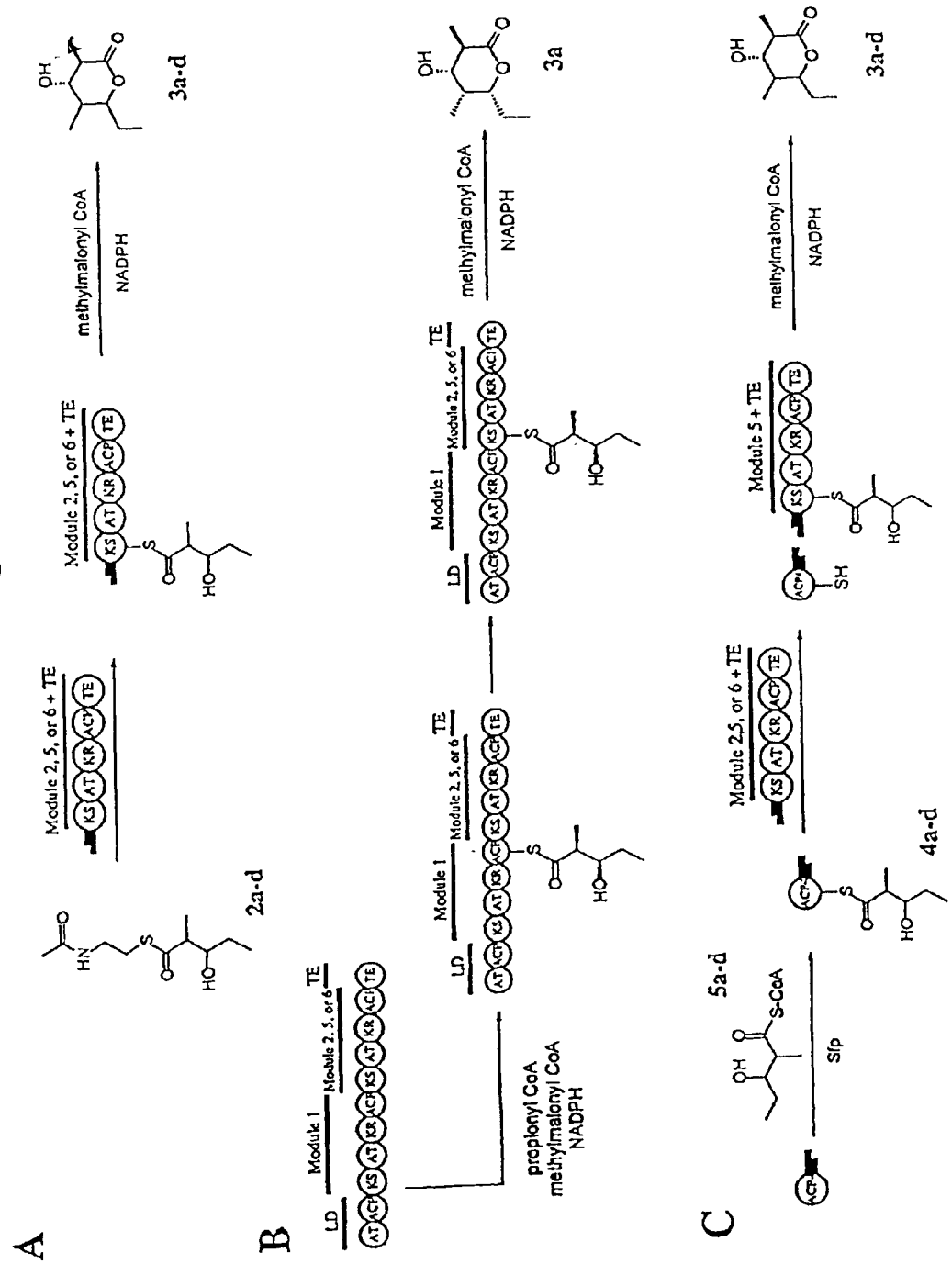
FIG. 10 presents schematic illustrations of three mechanisms of loading a DEBS module with a diketide

FIG. 10 presents schematic illustrations of the three mechanisms of loading a DEBS module with a diketide. (A) In a diffusive mechanism, diketides that have been activated as N-acetylcysteamine thioesters (diastereomers 2a–d) are loaded exogenously onto the KS domain. Claisen-like condensation with a C3-unit derived from methylmalonyl CoA followed by NADPH-dependent reduction gives the corresponding triketide lactone products (3a–d). (B) In an intrapolypeptide channeling mechanism, a diketide that is generated by module 1 from propionyl CoA, methylmalonyl CoA, and NADPH is passed intramolecularly from ACP1 to KS2. Subsequent elongation and reduction afford the triketide lactone 3a. (C) In an interpolypeptide channeling mechanism, diketides that have been chemoenzymatically attached to ACP4 by Sfp (4a–d) are transferred to the KS domain on a separate polypeptide. Elongation and reduction afford the corresponding triketide lactones (3a–d). In all cases suffix "a" refers to the (2S,3R) diastereomer, suffix "b" refers to the (2R,3S) diastereomer, suffix "c" refers to the (2S,3S) diastereomer, and suffix "d" refers to the (2R,3R) diastereomer. See also FIG. 11.

Figure 11:
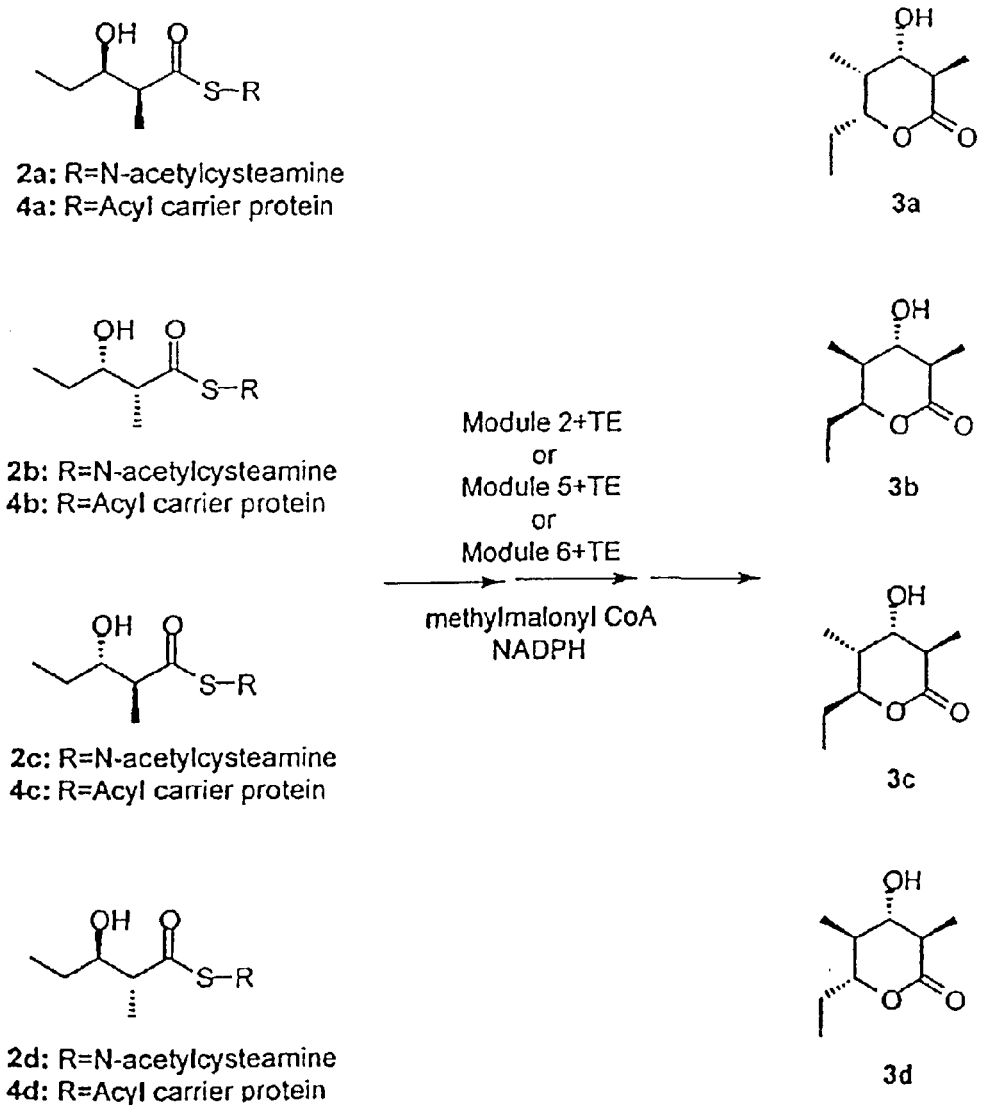
FIG. 11 illustrates four diketides and their corresponding, putative enzymatic products.

FIG. 11 illustrates the four diketides and their corresponding, putative enzymatic products. See also caption to FIG. 10.

Figure 12:
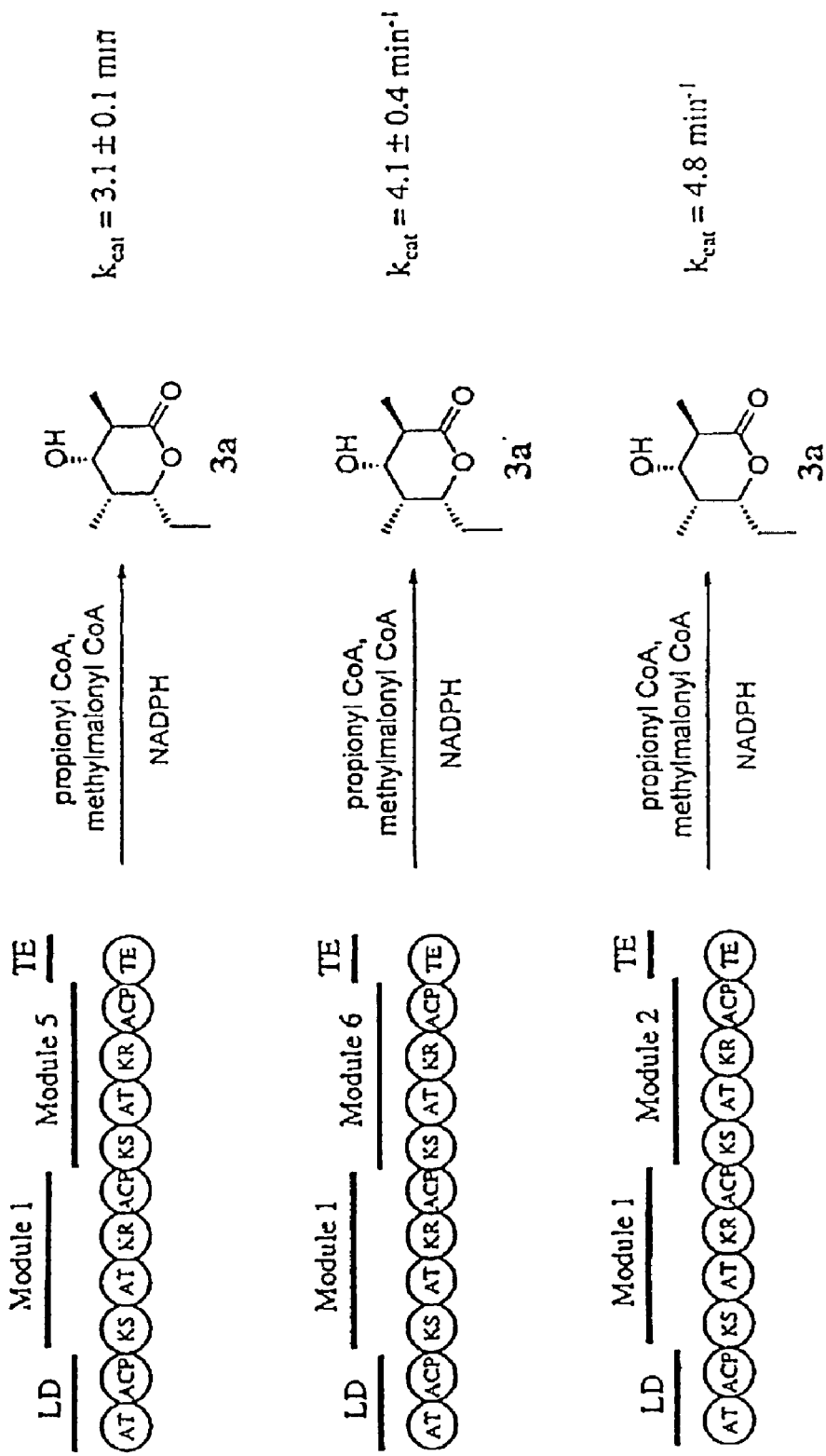
FIG. 12 presents the reaction schemes of the three bimodular DEBS derivatives—M1+M5+TE (module 1+module 5+TE), M1+M6+TE, and M1+M2+TE (DEBS1+TE)—and their corresponding $k_{cat}$ values.

FIG. 12 presents the reaction schemes of the three bimodular DEBS derivatives—M1+M5+TE (module 1+module 5+TE), M1+M6+TE, and M1+M2+TE (DEBS1+TE)—and their corresponding $k_{cat}$ values.

FIG. 13 presents a comparison of the $k_{cat}/K_M$ values ($min^{-1}$ $mM^{-1}$) of the two syn-diketides when presented as acyl-ACP substrates (4a and 4b) vs when presented as NAC-thioesters (2a and 2b). The $k_{cat}/K_M$ values for the NAC-thioesters were reporter earlier by Wu, N., et al., *J. Am. Chem. Soc.*, 2000, 122, 4847–4852.

FIG. 14 presents a comparison of the $k_{cat}$ values ($min^{-1}$) of the four diketides when presented as acyl-ACP substrates (4a–d) vs when presented as NAC-thioesters (2a–d). "N.D." denotes that the product was not detected.

Figure 15:
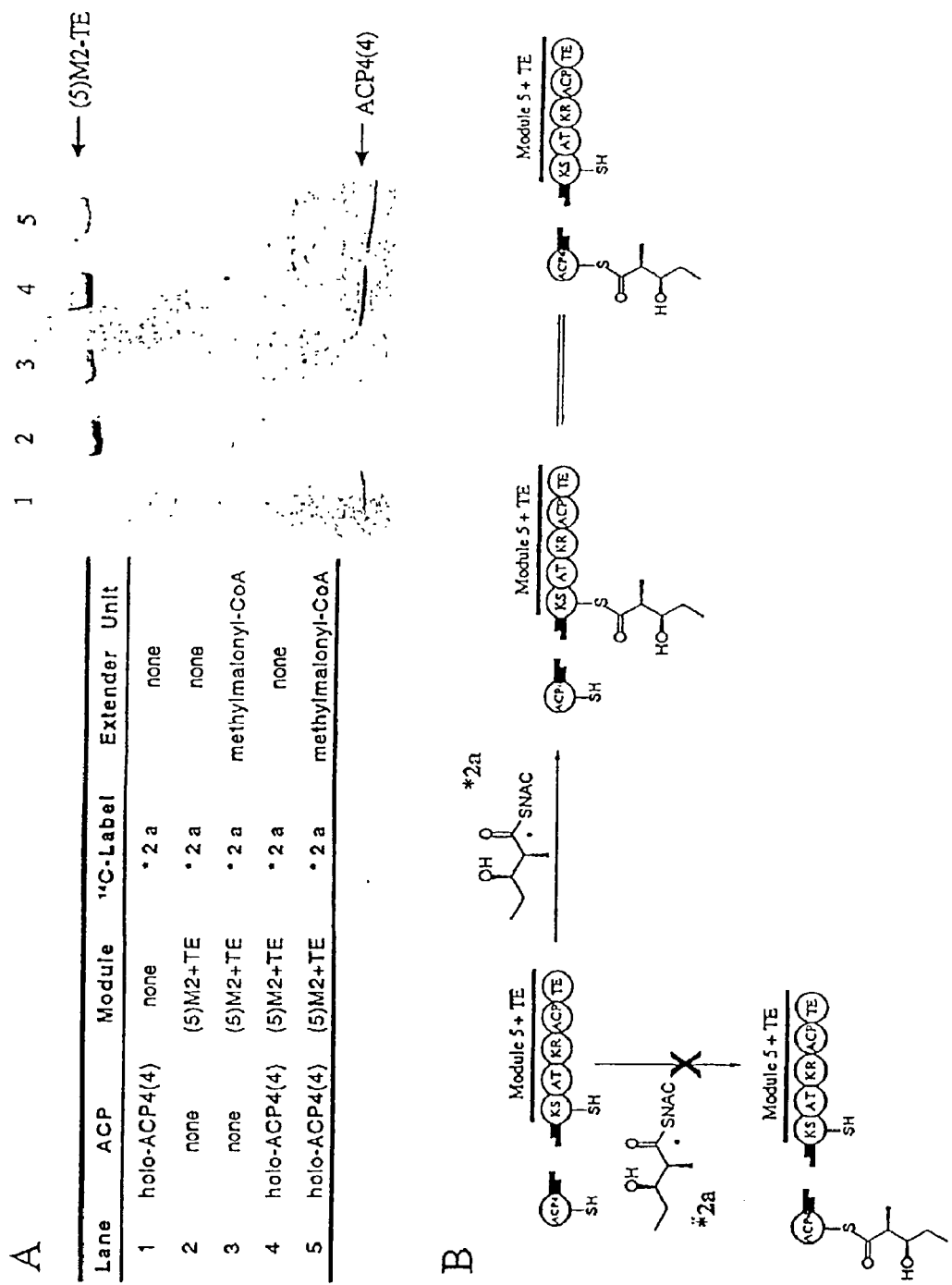
FIG. 15 presents conditions, results, and proposed mechanisms of back-transfer experiments.

FIG. 15 presents the following: (A) X-ray film image of SDS-PAGE gel and associated conditions of back-transfer experiments; and (B) proposed mechanism for back transfer of an exogenously loaded diketide from the KS of a formally downstream module to an upstream ACP.

Figure 16:
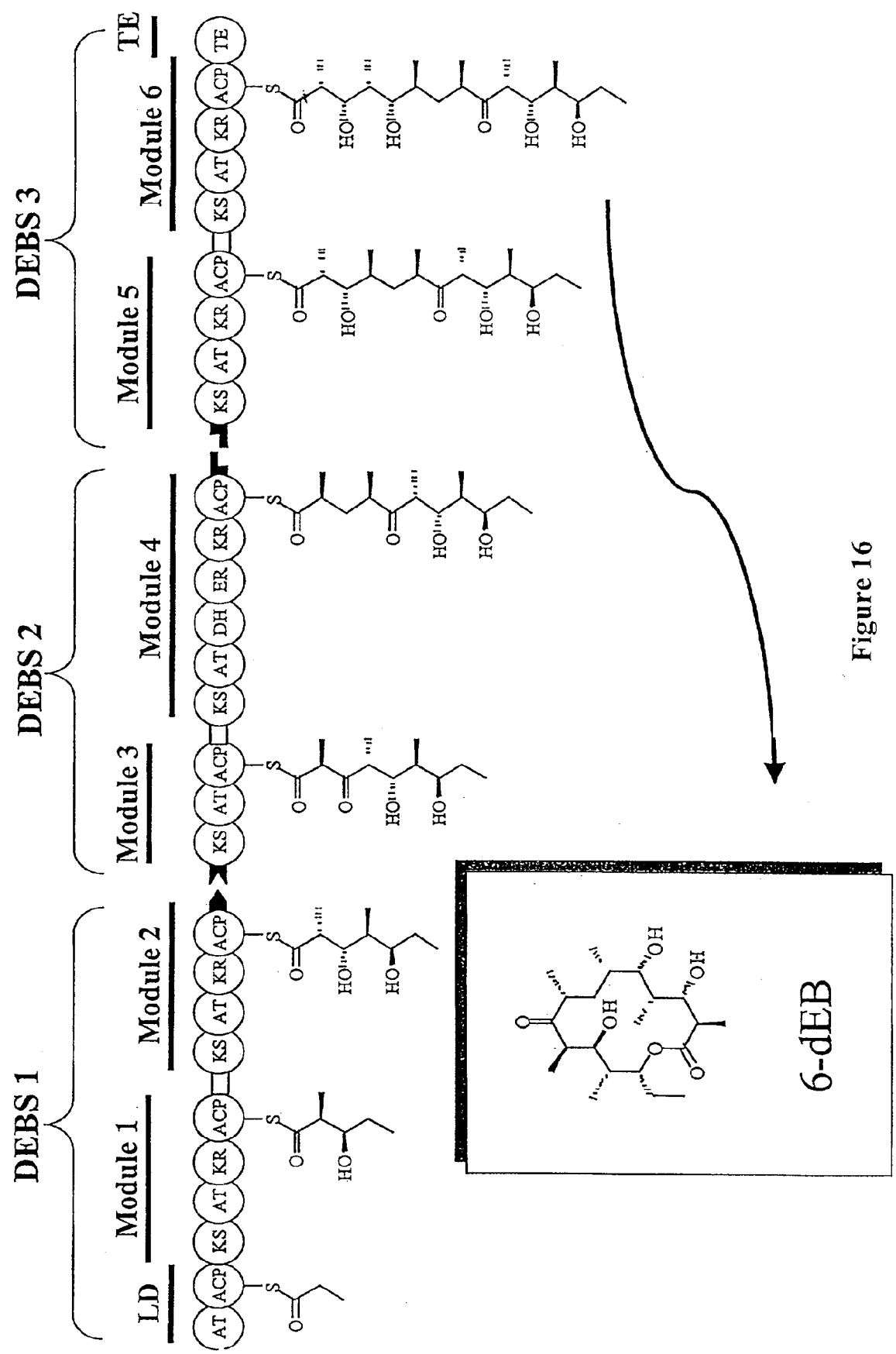
FIG. 16 is a schematic of 6-deoxyerythronolide B synthase.

FIG. 16 is a schematic of 6-deoxyerythronolide B synthase. Intermodular paris are shown in color. LD: loading domain; AT: acyltransferase; ACP: acyl carrier protein; KS: ketosynthase; KR: ketoreductase; DH: dehydratase; ER: enolyreductase; and TE: thioesterase.

FIG. 17 is a schematic of matched and mismatched linker pairs at intermodular interfaces. FIG. 17 shows how linker pairs at intermodular interfaces are selective, yet interchangeable. The left hand panel shows how matched linker pairs (triangular/triangular or square/square) facilitate efficient chain transfer. The right hand panel shows how mismatched linker pairs (triangular/square or square/triangular) abolish chain transfer without affecting the activity of individual modules.

FIG. 18 is a schematic illustrating the channeling of intermediates to unnatural recipient modules. Linker pairs can channel intermediates to unnatural recipient modules. The left hand panel shows that in addition to communicating with its natural partner, module 3 (as shown in FIG. 17), module 2 can also communicate with modules 5 or 6 as long as linker pairs are matched. The right hand panel shows that such communication is totally abolished if unmatched linker pairs are used.

Figure 19:
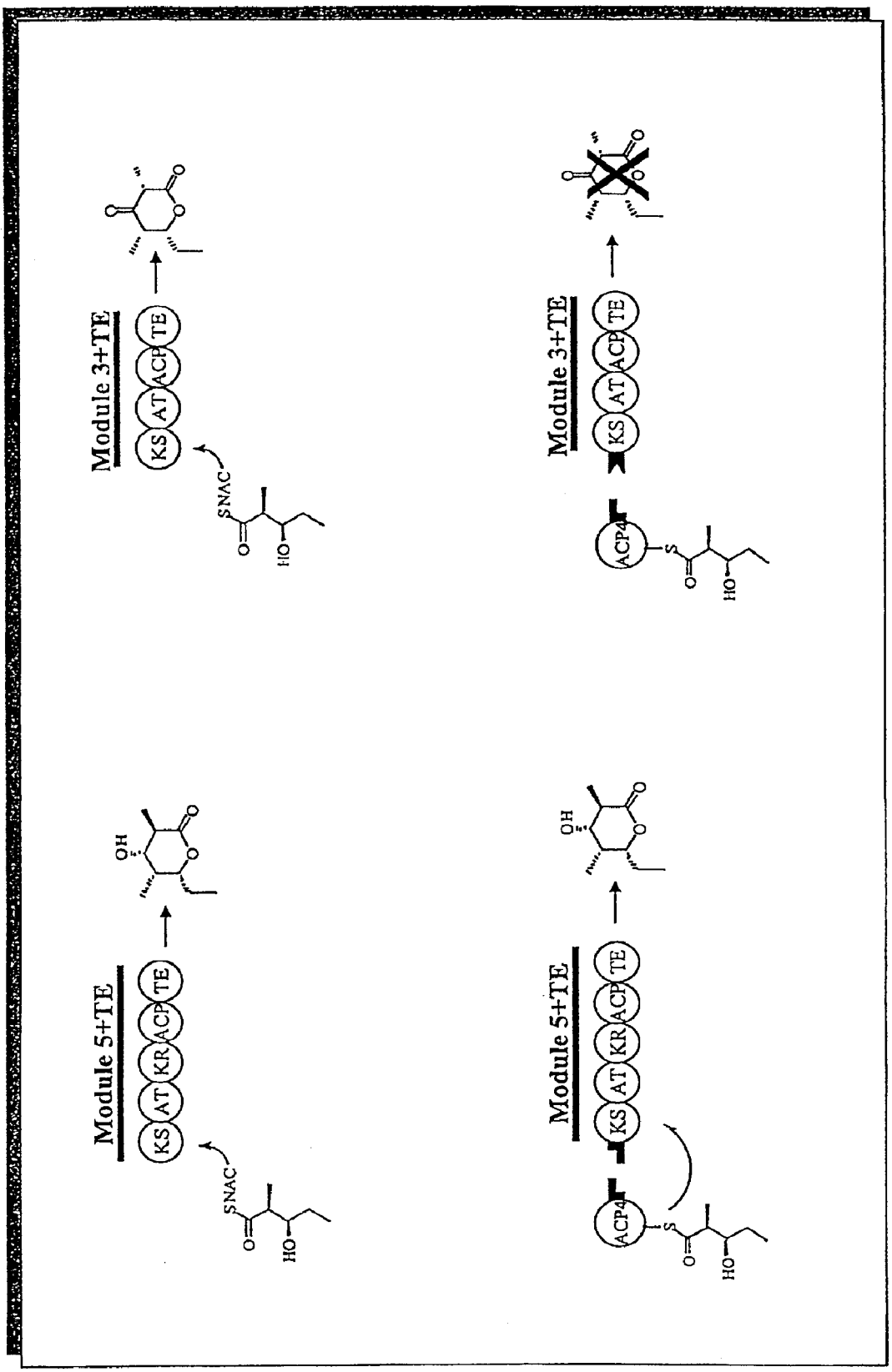
FIG. 19 is a schematic illustrating the replacement of the entire donor module with just the acyl carrier protein.

FIG. 19 is a schematic illustrating the replacement of the entire donor module with just the acyl carrier protein. The properties of linkers as shown in FIGS. 17 and 18 are maintained when the entire donor module is replaced with just the acyl carrier protein.

Figure 20:
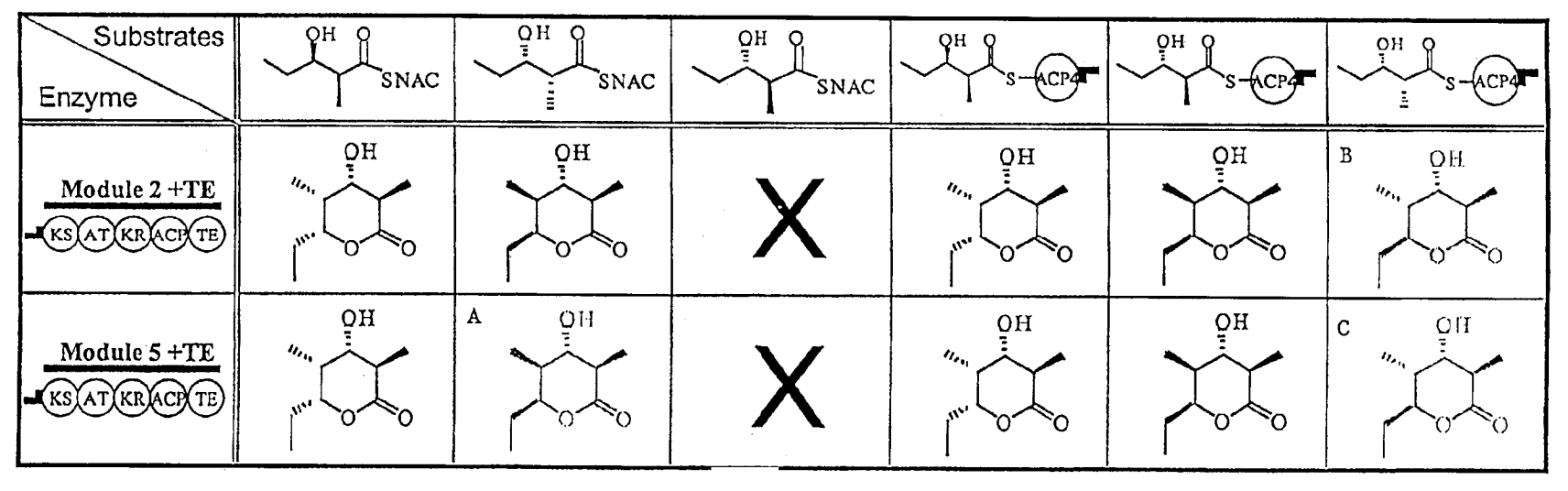

FIG. 20 is table summarizing the substrates and enzymes used to study substrate transfer from a donor to a recipient module. FIG. 20 shows how matched linker pairs are able to efficiently transfer otherwise poor substrates from a donor to a recipient module. Three different diastereomers of the natural substrate of module 2 were presented to either module 2 or module 5. These substrates were presented as N-acetylcysteamine (NAC) thioesters or on an ACP carrying a matched linker. In every case chain transfer via protein-protein interactions proved to be a useful method for substrate delivery. Products A, B, and C were producted at lower rates than the other products.

Figure 21:
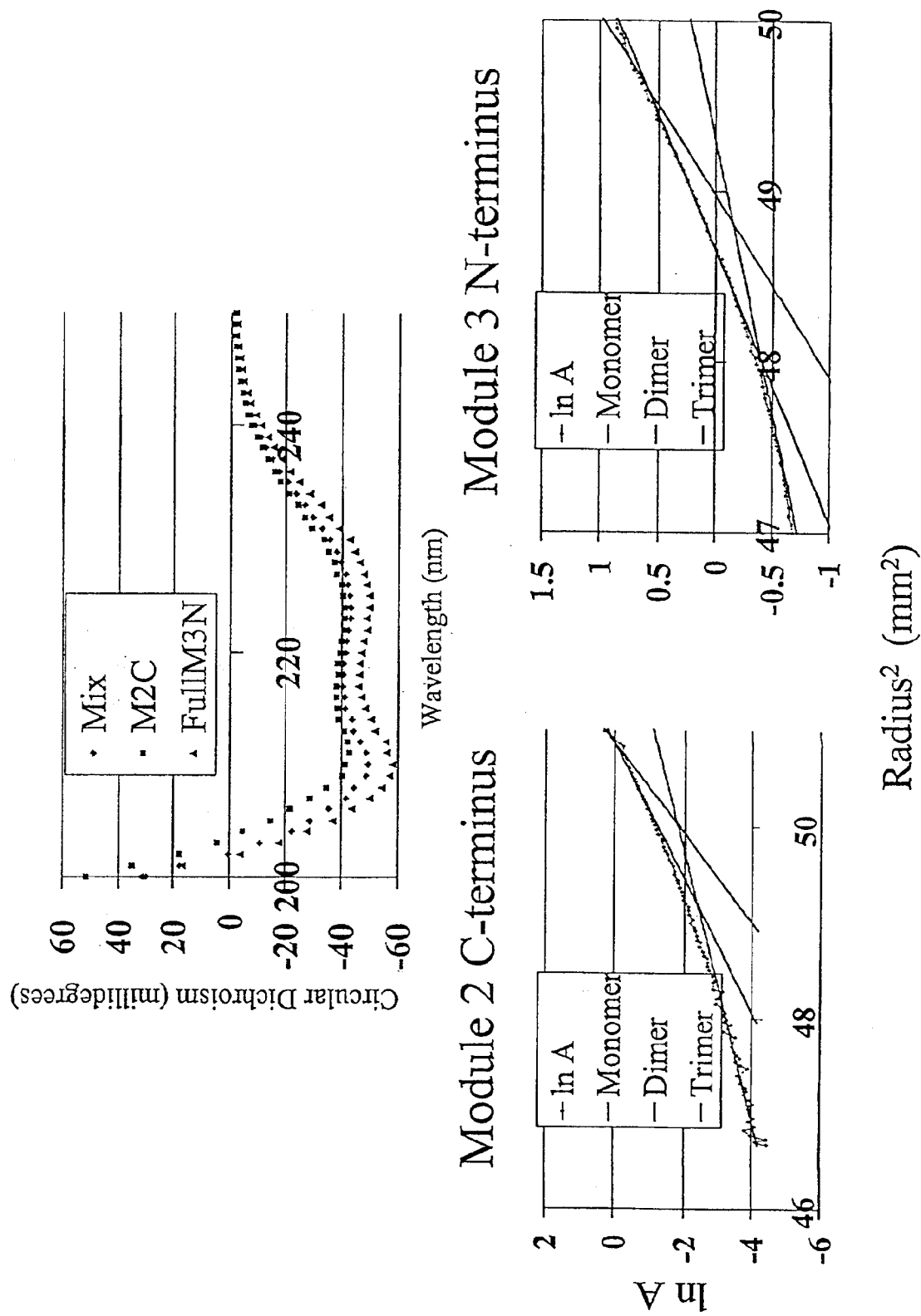
FIG. 21 shows data supporting a coiled-coil conformation for linkers.

FIG. 21 shows data supporting a coiled-coil conformation for linkers. Circular dichroism and ultracentriguation on synthetic peptides indicate a coiled-coil conformation for linkers. The top panel shows circular dichroism (millidegrees) versus wavelength (nm) for Mix, M2C, and FullM3N. The bottom left panel shows 1 nA versus radius$^2$ (mm$^2$) for linkers at module 2 C-terminus. The bottom right panel shows 1 nA versus radius$^2$ (mm$^2$) for linkers at module 3 N-terminus.

Figure 22:
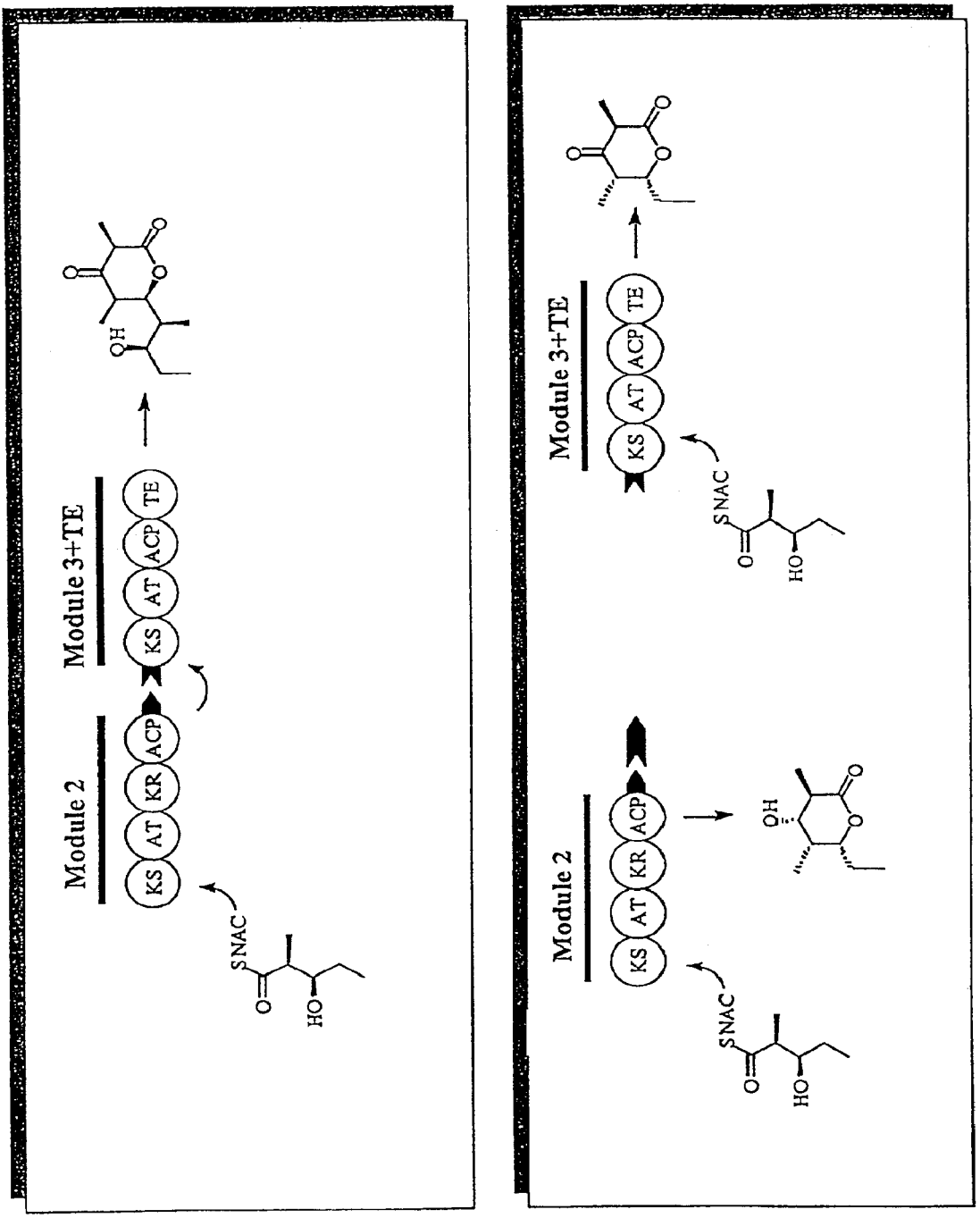
FIG. 22 is a schematic illustrating how exogenous peptide mimetics of linkers can inhibit chain transfer.

FIG. 22 is a schematic illustrating how exogenous peptide mimetics of linkers can inhibit chain transfer. This figure suggests that the linkers can adopt a functional, native conformation. The top panel shows a natural transfer and the bottom panel shows how the addition of an exogenous peptide inhibits the transfer.

Other features and advantages of the invention will be apparent from the following detailed description, and from the claims.

Modes of Carrying Out the Invention

The invention takes advantage of the identification of the amino acid sequences for supplying an appropriate linker between modules of a Type I PKS depending on the position of the module in the synthetic scheme for the polyketide. If the module is at the N-terminus of the polypeptide in which it resides—i.e., there is no additional module covalently bound upstream to it, an "interpolypeptide linker" (ERL) is placed upstream of the KS catalytic domain. Conversely, if the module resides in a polypeptide wherein there is an additional module upstream of it and covalently linked to it as a fusion protein, the two modules should be separated by an "intrapolypeptide linker" (RAL). If the module residing at the N-terminus of a polypeptide is downstream in the synthesis process for a polyketide—i.e., if it must accept a nascent polypeptide chain from a different module not on the same molecule, it may be necessary as well to supply a portion of the interpolypeptide linker at the C-terminus of the module providing the nascent polyketide chain in order to assure orderly transfer.

In the discussion that follows, polyketide synthases are discussed either at the protein level or the DNA level. As is well understood, manipulation of the sequence of amino acids in the polyketide synthase proteins is most conveniently done using recombinant techniques. Thus, for example, the appropriate linker sequences can be introduced to or modified with respect to those of an existing module by modifying the appropriate gene and expressing it in a suitable host. Interchange of linkers is also conveniently done in this manner. Further, modifications of amino acid sequences so as to obtain "variants" are effected by mutating the gene. The referent polyketide synthase should be understood to exist at both the protein level and nucleic acid level, and which form is being discussed should be apparent from the context.

Further, the action of polyketide synthases on their appropriate substrates can be effected either extracellularly by using isolated enzymes or may be effected by producing the enzymes intracellularly. By "appropriate substrate" is meant the extender units in their thioester forms that are recognized by the various modules in the PKS and "starter" units which are either thioesters of carboxylic acids or partially synthesized polyketides such as diketides. For example, as described in PCT application PCT/US96/11317, the ketosynthase domain of module 1 may conveniently be inactivated thus making more efficient the utilization of the diketide by module 2.

The linkers can be supplied by conventional recombinant DNA manipulations through the use of restriction enzymes and ligation procedures commonly practiced. The linkers in the PKS of the invention will be "isolated" from their natural environments. By "isolated," as used herein, is meant simply that the referent is found linked in association with moieties with which it is not normally associated, or in an environment in which it is not naturally found. It may be linked, if a nucleotide sequence to additional sequence with which it is not normally linked, or, if a peptide, to additional amino acid sequence with which it is not ordinarily linked, or it may be simply detached from additional moieties with which it is usually associated.

As seen from FIG. 3, the intrapeptide linkers (RAL) of the invention contain approximately 16–20 amino acid and typically contain a proline residue at approximately the middle of the sequence. On the other hand, the N-terminal upstream interpolypeptide linkers are approximately twice as long and appear to contain conserved acidic amino acid residues and basic amino acid residues at positions in the upstream half of the molecule. Thus, typical N-terminal upstream interpolypeptide linker (ERL) will contain an acidic amino acid within the first 3–10 residues, which is followed after 8–10 residues by a basic amino acid, and then after another 2–5 amino acid residues by an additional acidic amino acid. Additional acidic and basic residues may also occur in these linkers.

The intrapeptide linkers or interpeptide linkers shown in FIG. 3 can be used as described below in the present invention or the corresponding amino acid sequences from native Type I PKS in general can be employed. In addition to the sequences that occur in nature, "variants" may be used. These variants are obtained by altering the amino acid sequence of the linker in minor ways that do not affect the ability of the linker to "feed" the nascent polyketide chain to the module in question. Typically, such "variants" are obtained from the native sequences by amino acid substitution, deletion or insertion; preferably the substitutions are "conservative" substitutions—i.e., an acidic amino acid for a different acidic amino acid, a basic amino acid for a different basic amino acid, and the like. Preferably, the variants contain no more than three amino acid alterations, preferably only two, and more preferably only one.

For construction of polyketide synthases which contain more than one polypeptide, the appropriate sequence of transfers is assured by matching the appropriate C-terminal amino acid sequence of the donating module with the appropriate N-terminal amino acid sequence of the interpolypeptide linker of the accepting module. This can readily be done, for example, by selecting such pairs as they occur in native PKS. For example, two arbitrarily selected modules could be coupled using the C-terminal portion of module 4 of DEBS and the N-terminal of portion of the linking sequence for module 5 of DEBS.

In general, the method of the invention involves supplying to a module used in a PKS for synthesis of a desired polyketide with the appropriate N-terminal upstream portion interpolypeptide linker (N-ERL), C-terminal downstream portion of an interpolypeptide linker (C-ERL) or with an intrapolypeptide linker (RAL) at either terminus. As stated above, if the module is at the N-terminal portion of a polypeptide, an N-terminal upstream interpolypeptide linker should be appended at its N-terminus. If the module resides in a polypeptide where there is an additional module fused upstream from it, the two modules should be separated by an intrapolypeptide linker.

For ease of construction, a library of functional modules can be maintained to provide the appropriate desired module for construction of the PKS. One way to ensure the appropriate sequence of polyketide chain growth is to link the modules covalently, so that all but the first module will contain upstream intrapolypeptide linkers. Alternatively, and preferably, appropriate communication between functional modules non-covalently associated on separate polypeptide molecules can be achieved by providing appropriate matching between the C-terminal downstream portion of the interpolypeptide linker associated with the module contributing the nascent polyketide chain and the N-terminal upstream portion of the interpolypeptide linker placed upstream of the module which accepts and extends this nascent polyketide. Thus, an appropriate linker to ensure that the growing polyketide chain will be passed from module A to module B, which modules are not covalently bound, would be to couple, for example, the C-terminal scaffold portion of module 4 from erythromycin to module A and the N-terminal interpolypeptide linker (scaffold) portion from module 5 of the erythromycin PKS to the N-terminus of the KS of module B.

To design and construct the PKS, one straightforward approach is to utilize the existing linker regions of a native PKS, such as erythromycin PKS, and simply to "plug in" modules, for example from a library.

A library of modules derived from naturally occurring PKS which contains modules incorporating all alternative extender units used in native PKS combined with all variants of beta-carbonyl modification is not large. Extender units that are incorporated naturally include malonyl-CoA, methylmalonyl-CoA, ethylmalonyl-CoA, and hydroxymalonyl-CoA. The appropriate native molecule for incorporation of each of these can readily be found. Methylmalonyl-CoA extender units are incorporated, for example, by the modules of the erythromycin PKS. Certain modules of the picromycin PKS incorporate malonyl-CoA, while modules of the epothilone PKS incorporate ethylmalonyl-CoA or hydroxymalonyl-CoA. Modules occur naturally which contain the full spectrum of beta-carbonyl modifying activities; to the extent it is desirable to couple a particular beta-carbonyl modifying activity with a particular extender specificity, this can be accomplished by altering catalytic domains, per se, as described in the above-referenced PCT publication WO 98/49315. The complete combination of extender unit choices with all beta-carbonyl modification choices is thus only a total of 4×4 or 16 modules. As the KS unit determines the stereoselectivity of the module, accommodation can be made for various stereoisomeric forms of precursor by adjusting the KS domain in the module library. This expands the total number of modules necessary only to 32. An arbitrary number of modules can be included in a particular PKS construct, thus also determining the length of the polyketide chain and the size of the macrolide product. Of course, the macrolide product can be modified, if desired, by the known tailoring enzymes which convert naturally occurring macrolides to hydroxylated and/or glycosylated forms and the like. Such modification can be achieved in a variety of ways—by chemical modification, by in vitro treatment with appropriate enzymes, or by feeding the polyketides to a host organism which contains the appropriate tailoring enzymes, as is well understood in the art.

To construct the desired PKS, modules are selected from the library and provided the appropriate upstream intrapolypeptide or interpolypeptide linkers. Suitable linkers can be selected from the group consisting of those shown in FIG. 3, the corresponding sequences from any Type I PKS, or can include variants of these depicted sequences which are conservative in nature and do not interfere with the ability of the linker to permit effective uptake of the nascent polypeptide chain. The linkers can be added by standard recombinant techniques to the modules in the library, or, the library can be composed of the collection of modules wherein each module has been further manipulated to include either an intrapolypeptide or interpolypeptide linker. It may be desirable, for example, to provide each type of extender module with an intrapolypeptide linker, including the possibility of retaining the linker that is normally associated with it. If the linker is placed at the N-terminus of the module, the module is suitable for covalent linking downstream of an additional module in a single polypeptide. If the intrapolypeptide linker is at the C-terminus, ordinarily that module will be placed and linked covalently upstream of an additional module. In any case, a module may arbitrarily be provided with an intrapolypeptide linker (RAL) at either its N- or C-terminus depending on where it is ultimately to be placed in the PKS to be constructed or may be provided with the N-terminal upstream portion of an interpolypeptide linker (N-ERL) if it is to be placed at the N-terminus of a polypeptide in the PKS, or with a C-terminal portion of an interpolypeptide linker (C-ERL) if it is to be placed at the C-terminus of a polypeptide and is intended to transfer a nascent polyketide chain to a subsequent module.

The various modules, with appropriate linkers are then assembled into the desired polyketide synthase. As stated above, the construction of the PKS can be based on plugging in active portions of modules into an existing linker array The assembly can be performed by simply mixing the peptides containing the modules or may be generated recombinantly from expression constructs in a host cell. The cell may provide the appropriate substrates for the PKS, or the substrates may need to be provided to the reaction mixture containing the polypeptides or to the cells in which they are generated. Depending on the choice of host, provision may need to be made for providing these substrates.

In this way, the modules can be "mixed and matched" as desired to construct a polyketide product from the desired extender units and with the desired beta-carbonyl modification, choosing the linkers in accordance with the position of the module in a polypeptide, and the number of modules cam be altered as desired.

A preferred starter unit for such an assembly of modules is a diketide thioester either formed in situ by including a module which contains a loading domain to incorporate a starter unit along with an extender unit to attain this resultant, or the diketide may be synthesized independently and used as the substrate for the PKS. The synthesized diketide may be supplied as the thioester, such as the N-acylcysteamine thioesters. Preparation methods for these thioesters are described in the above-referenced U.S. Ser. No. 09/346,860 filed 2 Jul. 1999 now U.S. Pat. No. 6,221, 641 and the corresponding PCT application, as well as U.S. Ser. No. 09/492,733 filed 27 Jan. 2000, now U.S. Pat. No. 6,492,562.

Using the techniques of the invention, it is thus possible to manipulate entire modules and effect efficient cross-talk so as to assure production of the desired macrolide. Such techniques can be used, for example, to alter the structure of macrolide anti-infectives by, for example, replacing the module 2 of the erythromycin gene cluster with module 2 of the tylosin gene cluster, or replacing the erythromycin module 6 (along with its thioester sequence) with the corresponding module 6 from narbomycin.

In addition, 14-membered macrolides could be expanded to become 16-membered macrolides by fusing modules 2–3 of the tylosin, spiramycin or niddamycin modules 2–3 between modules 1 and 3 of the erythromycin synthase or by adding any arbitrarily chosen module from other Type I PKS clusters into the synthase for production of erythromycin. Alternatively, modules 1–2 of erythromycin could be deleted and replaced by modules 1–3 of tylosin, spiramycin or niddamycin.

In addition, new substituents can be introduced into, for example, PKS erythromycin or its precursors by replacing the second module of the erythromycin PKS with module 5 from tylosin PKS where the substituted module has the enoyl reductase catalytic activity inactivated. This results in erythromycins substituted with an ethyl group at the 10-position. Alternatively, erythromycin module 5 could be replaced by the spiramycin module 6 to obtain 5-desmethyl-4-OH erythromycins.

Improved forms of FK-506 are obtained by replacing rapamycin modules 2–10 with FK-506 modules 2–6, or by replacing rapamycin modules 2–11 with FK-506 modules 2–7 or by replacing rapamycin modules 2–12 with FK-506 modules 2–8 or by replacing rapamycin modules 11–14 with FK-506 modules 7–10. Any combination or subset of the above could also be employed. Improved forms of FK-520 can be made in a similar manner. An alternative form of rapamycin is synthesized by substituting the FK-506/520 module 1 for rapamycin module 1.

The foregoing are merely exemplary of the types of manipulations that could be employed. The polyketides, obtained by supplying the appropriate substrates either in vitro or in vivo, may then be further modified if desired by hydroxylation, glycosylation and the like to obtain desired products. Further, chemical synthetic manipulations may also be employed.

Some of the resulting compounds described above could be prepared by alternative techniques previously disclosed, for example, in PCT applications PCT/US99/22886 or PCT/US99/24483. However, the procedure described above, which manipulates entire modules, may result in better yield or more convenient synthesis.

In addition to housing six modules, the three polypeptides of DEBS each possess short, nonconserved segments of amino acid residues located at the N- and C-termini of adjacent polypeptides (shown with complementary symbols in FIG. 4 and described in Example 6 below). A previous study has discussed the importance of keeping these inter-polypeptide "linkers" intact during the engineering of chimeric PKSs (Gokhale, R. S., et al. (1999) Science 284, 482–485. To dissect the precise role of these linkers in mediating intermodular interactions, an in vitro system consisting of a donor module and an acceptor module was developed and kinetically characterized and is described in Example 6 below. Each of the components of this functional linker pair could then be replaced with counterparts from other naturally occurring linker pairs. The results of these experiments, shown in Example 6 and accompanying FIGS. 4–9, support the understanding that the linker regions outside a module's conserved catalytic domains impact its interactions with other modules. In addition to their importance in functionally connecting modules, these short sequences also play an active role in the protein-protein recognition of modules, helping to maintain the selective transfer of intermediates.

There are several strategies for rationally manipulating polyketide structure by engineering DEBS. For example, it has been demonstrated that DEBS is amenable to the introduction of unnatural side chains at the $C_{13}$ and $C_{11}$ positions via precursor-directed feeding of diketides (Jacobsen, et al., Science 1997, 277, 367–369; Jacobsen, et al., Bioorg. Med. Chem. 1998, 6, 1171–1177; Hunziker, et al., Tetrahedron Lett. 1999, 40, 635–638), as well as via replacement of loading didomains from alternative synthases. See Marsden, et al., Science 1998, 279, 199–202). In addition, protein engineering of DEBS can generate truncated polyketides, (Kao, et al., Am. Chem. Soc. 1994, 116, 11612; Cortes, et al., Science 1995, 268, 1487–1489; Kao, C. M., et al., J. Am. Chem. Soc. 1995, 117, 9105–9106; Kao, et al., Am. Chem. Soc. 1996, 118, 9184) epimerized polyketides (Bohm, et al., Chem Biol 1998, 5, 407–412; Kao, et al., J. Am. Chem. Soc. 1998, 120, 2478–2479; Holzbaur, et al., Chem. Biol. 1999, 6, 189–195; Bycroft, et al., Biochem. 2000, 267, 520–526), desmethyl polyketides (Oliynyk, et al., Chem. Biol. 1996, 3, 833–839; Ruan, et al., J. Bacteriol. 1997, 179, 6416–6425; Liu, et al., Am. Chem. Soc. 1997, 119, 10553–10554; Lau, et al., Biochemistry 1999, 38, 1643–1651), polyketides containing various degrees of modification of the β-keto groups (Donadio, et al., Science 1991, 252, 675–679; Donadio, et al., Proc. Natl. Acad. Sci. U.S.A 1993, 90, 7119–7123; Bedford, et al., 1996, 3, 827–831; McDaniel, et al., Am. Chem. Soc. 1997, 119, 4309–4310; Kao, C. M., et al., Am. Chem. Soc. 1997, 119, 11339–11340), and combinations thereof. See McDaniel, et al., Proc. Natl. Acad. Sci. U.S.A 1999, 96, 1846–1851. However, one approach for generating diversity in polyketides that has been exploited only to a limited extent (Gokhale, et al., Science 1999, 284, 482–485; Ranganathan, et al., Chem. Biol. 1999, 6, 731–741) is the fusion of intact modules (or groups thereof) from different PKSs to generate chimeric assembly lines. While the application of such a strategy takes advantage of the natural catalytic grouping of the modules to produce enzymes of improved catalytic effectiveness, two major issues must be addressed to rationally implement a modular rearrangement strategy for combinatorial biosynthesis. First, the molecular recognition features of individual modules need to be deciphered, so that their placement in hybrid PKSs can be restricted to catalytically productive contexts. Second, the mechanistic basis for transferring intermediates between adjacent modules must be understood, so that intermodular chain transfer can efficiently occur between heterologous modules. This report provides new insights into the relative importance of both of these issues and their interrelationships in the context of a multimodular PKS.

The tolerance and specificity of individual modules of DEBS have been indirectly investigated using a variety of genetic, biochemical, and chemical approaches.[25] Recently, it has been possible to express and reconstitute individual DEBS modules as intact proteins. See Gokhale, et al., Science 1999, 284, 482–485. This allowed us to directly assess the substrate specificities of four modules of DEBS (modules 2, 3, 5, and 6) using a set of N-acetylcysteamine (NAC)-activated diketides as potential substrates (2a–d, FIG. 10A), Wu, et al., Am. Chem. Soc. 2000, 122, 4847–4852. Surprisingly, not only did the substrate specificity profiles of these four individual modules turn out to be quite similar, but these profiles also did not correlate well to the structures of the natural substrates of individual modules. Separately, recent experiments have suggested that short intermodular linker sequences play an important role in the selective transfer of polyketide intermediates between modules. See Gokhale, et al., Science 1999, 284, 482–485; Tsuji, et al., Biochemistry 2001. Therefore, we considered it appropriate to reexamine the steady-state kinetic parameters of individual DEBS modules, but this time, to pay closer attention to possible protein-protein interactions that could be involved in passing a substrate from an upstream module to its downstream neighbor.

There are two modes by which a substrate can be passed from one module to the next. If the two successive modules are on the same polypeptide (such as modules 1 and 2 of DEBS), there is an intrapolypeptide chain transfer. On the other hand, if the two successive modules are on separate polypeptides (such as modules 2 and 3 of DEBS), there is an interpolypeptide chain transfer. In either case, biosynthetic intermediates undergo direct interthiol transfer between adjacent modules such that the intermediates never go into bulk solution. We refer to this property as the "physical channeling" of intermediates between modules.

Physical channeling (also commonly referred to as substrate channeling) is defined as a mechanism in a sequence of reactions in which reaction intermediate is transferred from one active site to the downstream active site without equilibrating with the bulk solution. See Kirsch, et al., *Biochemistry* 1999, 38, 8032–8037. Physical channeling of intermediates can provide kinetic benefits by increasing the effective concentration of the substrate, protecting labile intermediates from unproductive reactions, and precluding entrance of intermediates into competing enzymatic pathways. Furthermore, substrate channeling between two enzymes can help overcome product inhibition of the upstream enzyme by funneling the intermediate out of the upstream binding pocket and into the downstream binding pocket more efficiently.

While physical channeling is a necessary outcome of fundamental polyketide biosynthetic mechanisms (Donadio, et al., *Science* 1991, 252, 675–679; Cortes, et al., *Nature* 1990, 348, 176–178), the kinetic advantage, if any, of channeling intermediates between modules has not yet been resolved. To elucidate the issue of "kinetic channeling" (which is defined as physical channeling that results in a kinetic advantage—as measured by $k_{cat}$ sover a diffusive loading mechanism in which the intermediate equilibrates in the bulk phase after release from the upstream active site and before loading in the downstream active site) in modular PKSs, two new assay systems-one to probe intrapolypeptide transfers and one to probe interpolypeptide transfers—were devised that would more accurately mimic the transfer of a substrate from the acyl carrier protein (ACP) of one module to the ketosynthase (KS) of the next. These assays are described in further detail in Example 7 below. In the first assay system, the loading didomain and module 1 of DEBS generated in situ the natural diketide intermediate ((2S,3R)-2-methyl-3-hydroxy-pentanoyl-S-ACP$_1$), which could then be transferred to alternative downstream modules in a bimodular PSK context (FIG. 10B). By comparing the kinetic parameters of these hybrid bimodular systems to those for elongation of the same diketide that has been supplied exogenously to the isolated downstream module (FIG. 10A), the kinetic benefit of channeling intermediates between covalently linked modules could be evaluated. A second assay system was developed using a chemoenzymatic method, through which alternative diketides were covalently attached to the phosphopantetheine arms of an individually expressed donor ACP domain (FIG. 10G). Here, the entire diketide-S-ACP adduct (4a–d) is a formal substrate for a recipient module, therefore allowing investigation of interpolypeptide channeling. (The linker sequence at the C-terminal end of the ACP as previously described, see Tsuji, et al., *Biochemistry* (2001) 40:2326–2331, was included in this construct.) By attaching different diketides to the same ACP, the steady-state kinetic parameters for diketide elongation by individual modules (each with a TE domain fused to its C terminus to facilitate turnover) could be measured. Both assay systems were used to compare the properties of modules 2, 5, and 6 of DEBS, three modules that perform the same chemistry with identical stereocontrol, albeit on very different substrates (FIG. 4). The results of these studies are described in Example 7 below.

The present invention is further described by the compounds and methods described in the following examples. The examples are provided solely to illustrate the invention by reference to specific embodiments. These exemplifications, while illustrating certain specific aspects of the invention, do not portray the limitations or circumscribe the scope of the disclosed invention.

Preparation A

Construction of Single Module Based Systems
Single Module Gene Constructs

Single module constructs from the DEBS gene cluster were prepared for modules 2, 3, 5 and 6 as follows. The TE domain is fused to the module to facilitate termination. The (M3+TE) gene was prepared from the tri-modular construct pKAO318 (McDaniel, R., et al., *Chem. Biol.* (1997) 4:667) having an NheI site engineered at the start of the DEBS-2 gene. Fusion of the TE gene at the end of ACP3 was described in connection with the construction of pCK13 in Cortes, J., et al., *Science* (1995) 268:1487; Kao, C. M., et al., *J. Am. Chem. Soc.* (1995) 117:9105 and Kao, C. M., et al., *J. Am. Chem. Soc.* (1996) 118:9184, collectively cited below as the "Cortes-Kao documents." The NheI-EcoRI fragment was cloned into pET 21c (Novagen) to construct pRSG34. The EcoRI site was used to delete the stop codon of the TE domain so that the protein could be overproduced as a carboxy terminal (His)$_6$ tagged fusion protein.

(M5+TE) was constructed by combining the engineered NdeI site from pJRJ10 (Jacobsen, et al., *Biochem* (1998) 37:4928) with the EcoRI site from pCK15 (Cortes-Kao documents). The Nde-EcoRI fragment was cloned in pET21c to obtain the expression plasmid pRSG46. Expression constructs for (M2+TE) and (M6+TE) were prepared similarly using an engineered Nhe site immediately upstream of the corresponding KS (at position 7570, 5'-GCTAGCGAGCCGATC-3' (SEQ ID NO:1) and at position 28710, 5'-GCTAGCGACCCGATC-3' (SEQ ID NO:2)).

These constructs were expressed in *E. coli* BL21 (DE3) along with an expression system for sfp phosphopantetheinyl transferase from *B. subtilis*. The co-expression is described by Lambalot, R. H., et al., *Chem. Biol.* (1996) 3:923. For the construction of the sfp gene, the NdeI-HindIII fragment derived from the pUC8-sfp (Nakano, et al., *Mol. Gen. Genet.* (1992) 232:313) was cloned into pET28 which has a kanamycin resistance gene to give resultant plasmid pRSG56. The resulting proteins were then isolated for use in the reaction mixtures described in the Examples below.

In more detail, the expression was induced with 1 mM isopropyl-b-D-thiogalactopyranoside, and the cells were harvested by centrifugation after 10 hours and resuspended in disruption buffer, 200 mM sodium phosphate pH 7.2, 200 mM sodium chloride, 2.5 mM dithiothreitol, 2.5 mM sodium ethylenediamine tetra-acetate (EDTA), 1.5 mM benzamidine, 2 mg/L pepstatin and leupeptin and 30% v/v glycerol. The cells were lysed by passing through a french press, and the lysate was collected after centrifugation. Nucleic acids were precipitated with polyethylenimine (0.15%) and removed via centrifugation. The supernatant was made 50% (w/v) saturated with ammonium sulfate and precipitated overnight. After centrifugation, the pellet containing protein was redissolved in buffer A (100 mM sodium phosphate pH 7.2, 2.5 mM DTT, 2 mM EDTA and 20% glycerol (v/v)) and stored at −80° C. For chromatography, the buffer was exchanged to buffer A+1 M ammonium sulfate using a gel filtration PD10 (Pharmacia) column. The resulting sample was loaded on a Butyl Sepharose (Pharmacia) column. Fractions containing DEBS proteins were pooled and applied on an anion exchange column (Resource Q; 6 mL, Pharmacia). Purified protein fractions were pooled and concentrated using Amicon centriprep30. Typical purified protein yields were ~3–4 mg/liter of culture. Greater than 90% of proteins were phosphopantetheinylated in vivo as a result of the overexpression of sfp phosphopantetheinyl transferase. Although the proteins were expressed as $(His)_6$-tagged proteins, they did not bind to a Ni-column under experimental conditions. It is unclear whether this inability to bind to a Ni-agarose column is due to steric effects or if the $(His)_6$ peptide was lost during purification.

EXAMPLE 1

Requirements for Cell-Free Synthesis of Triketides by Individual Modules—Identification of Linker Regions A cell-free system, tested for the ability to convert the cysteamine thioester of 2S,3R-2-methyl-3-hydroxypentanoic acid (compound 2 in FIG. 2), consisted of 0.5–10 mM concentration of the thioester, 2.5 mM $^{14}C$-labeled methylmalonyl CoA and 100 pmoles of purified protein prepared in Example 1 in a 100 μl reaction. In some cases, 1 mM of NADPH was added; this was done in assay mixtures containing (M2+TE), (M5+TE) and (M6+TE) proteins. The protein was, in each case, a single module of the DEBS PKS fused to the thioesterase (TE) termination region of module 6.

The reaction mixtures were quenched and extracted by ethyl acetate and separated by thin-layer chromatography (TLC) to discern the formation of the triketide ketolactone 3 and triketide lactone 4 (both shown in FIG. 2) after 30 minutes. Results are shown as the first four entries in Table 1.

TABLE 1

Formation of Triketides by Single Module Constructs

| Construct | Plasmid | Triketide Formed |
|---|---|---|
| 1. M3 + TE | pRSG34 | Yes |
| 2. M5 + TE | pRSG46 | Yes |
| 3. M2 + TE | — | No |
| 4. M6 + TE | — | No |
| 5. ERL – M2 + TE | pRSG64 | Yes |
| 6. ERL – M6 + TE | pRSG54 | Yes |
| 7. M1 – RAL – M6 – TE | pST96 | Yes |
| 8. M1 – RAL – M3 – TE | pST97 | Yes |
| 9. ery M1 – RAL – rif M5 + TE | pST110 | Yes |
| 10. (ery M1 – RAL rif M5 + ERL) + DEBS-2 + DEBS-3 | pST113 | Yes (dEB6) |

As seen in Table 1, although the expected triketides were formed from (M3+TE) and (M5+TE) (modules which reside at the upstream portion of their respective polypeptides), no triketides were formed from (M2+TE) or (M6+TE), (modules which reside at the C-terminal portions of their polypeptides). These latter results were unexpected since the diketide can be incorporated by module 2 when it is supplied as a part of the complete polypeptide DEBS-1. It was verified that the ACP domain was pantetheinylated in modules 2 and 6, and that for (M2+TE), the KS domain could not be acylated with radiolabeled diketide.

EXAMPLE 2

Modification of Single Modules with Linker Sequences

The constructs for (M2+TE) and (M6+TE) were modified by deleting the sequences encoding the amino acids upstream of the KS catalytic domain and substituting the first 39 amino acids from (M5+TE) containing the N-terminal portion of the interpolypeptide linker (N-ERL). The relevant constructs were prepared by replacing the BsaBI-EcoRI fragment in pRSG46 by the corresponding fragment from pCK4 to obtain (N-ERL-M2+TE), in plasmid pRSG64, or from pJRJ10 to obtain (N-ERL-M6+TE) in plasmid pRSG54. These constructs yield modules which contain the upstream 39 amino acids from module 5. The constructs were expressed in $E.$ $coli$ and proteins obtained as described in Preparation A. These proteins were able to produce the triketide product from diketide in the cell free system of Example 1, as shown in entries 5 and 6 in Table 1.

The various constructs which are successful in converting diketide to triketide were then evaluated for the kinetic constants $k_{cat}$ and $K_M$. These results are shown in Table 2. As shown in Table 2, the results are quite similar for all constructs except that the results from module 3 show a several-fold decrease in $k_{cat}$ as compared to the other modules. This is evidently due to the absence of beta-carbonyl modifying enzymes in module 3 as verified by the fact that removal of NADPH, (which is required for the activity of such modules) from the reaction mixture of (N-ERL-M6+TE) also results in a lowering of the $k_{cat}$.

TABLE 2

| Proteins | $k_{cat}$ × 100 (min$^{-1}$) | $K_M$ (mM) |
|---|---|---|
| (N-ERL – M2 + TE) | 8 ± 0.6 | 4.6 ± 0.4 |
| (M3 + TE) | 1.5 ± 0.3 | 4.4 ± 0.4 |
| (M5 + TE) | 7.5 ± 0.7 | 4.7 ± 0.4 |
| (N-ERL – M6 + TE) | 9.5 ± 0.6 | 4.3 ± 0.4 |
| (N-ERL – M6 + TE) (– NADPH) | 4.5 ± 0.7 | 4.1 ± 0.4 |

It is apparent from these results that the presence of the N-terminal upstream sequence associated with modules located at the N-terminal portion of the polypeptide is essential for permitting a module in this position to incorporate the growing polyketide chain.

EXAMPLE 3

Construction of (M1-RAL-M3+TE) and (M1-RAL-M6+TE)

The BsaBI-EcoRI fragments containing modules 3 and 6 respectively were cloned behind the M1 module which contains the intrapolypeptide linker (RAL) that natively resides between M1 and M2. The resulting M1-RAL-M3+TE and M1-RAL-M6+TE genes were then excised as PacI-EcoRI fragments and inserted into pCK12 resulting in plasmids pST97 and pST96 respectively. The corresponding proteins were produced by transformation into $S.$ $coelicolor$ CH999. The resulting strains of $S.$ $coelicolor$ were able to incorporate the diketide thioester into the triketide as shown by entries 7 and 8 in Table 1. (The triketide produced is the ketolactone 3 in FIG. 2.)

EXAMPLE 4

Additional Intrapolypeptide Mediated Transfer

A construct wherein the first module of the DEBS PKS cluster (ery), which contains the intrapolypeptide linker of the corresponding M1-M2 polypeptide from the erythromycin PKS, is fused to the fifth module of the rifamycin PKS (rif) was constructed by replacing the natural sequence at 28024 of rif ACP5 (5'-CGCGAC-3') with the SpeI recognition sequence 5'-ACTAGT-3'. The BsaBI-SpeI fragment containing rif M5 was excised and replaced the corresponding ery M1-RAL-fragment in pCK12 to obtain plasmid pST110. This plasmid, containing ery M1-RAL-rif-M5+TE was transformed into *S. coelicolor* CH999 and the resulting strain was able to incorporate the diketide into the triketide lactone as shown by entry 9 in Table 1. The amount is comparable to that produced in this strain transformed with DEBS-1+TE.

EXAMPLE 5

Construction of Modules for Intermolecular Transfer

The PacI-SpeI fragment of pST110 was inserted into a derivative of pCK7 (Kao, C. M., et al., *Science* (1994) 265:509) which had an SpeI site engineered at the beginning of the scaffolding sequence at the carboxy terminus of the polypeptide downstream of ACP2. The resulting pST113 construct still contains ery M1 linked to rif M5 via the natural intrapolypeptide linker between ery molecules 1 and 2, and also now contains rif M5 covalently linked to the downstream C-terminal portion of the ERL derived from ery M2. Thus, the complete ERL between the polypeptide generated by pST113 and the protein generated by a construct which generates DEBS-2 would correspond to the native ERL in the ery PKS—i.e., rif M5 would be associated with ery M3 via the natural interpolypeptide linker between ery molecules 2 and 3. Co-transformation into *S. coelicolor* of pST113 along with constructs that produce DEBS-2 and DEBS-3 results in the production of 6-dEB, as shown by entry 10 of Table 1.

EXAMPLE 6

Construction of Modules for Interpolypeptide Transfer With Matched and Mismatched Linker Pairs (M2 and M3+TE, M2 and (5)M3+TE, M2(4) and M3+TE, and M2(4) and (5)M3+TE)

Reagents and Chemicals. DL-[2-methyl-$^{14}$C] Methylmalonyl-CoA (56.4 mCi/mmol) was obtained from ARC, Inc.

The N-terminal linker of M3 was synthesized by New England Peptide (Fitchburg, Mass.). The peptide sequence was as follows, M3 N-term: H$_2$N-MTDSEKVAEYLRRATLDLRAARQRIRELESD-amide. (SEQ ID NO: 20)

Construction of Plasmids. Plasmid pBP19 contains module 2 of DEBS (M2) and is a derivative of pRSG64 (Gokhale, R. S., et al., (1999) *Science* 284, 482–485), where the thioesterase domain was replaced with a SpeI-EcoRI fragment containing the natural C-terminal linker for module 2 to make pBP19. Plasmid pST179 encodes a derivative of M2 containing the C-terminal linker of DEBS module 4 (M4). The C-terminal linker of M4 was obtained as a SpeI-EcoRI fragment by PCR using the primers 5'-ACT AGT AGG CTG TTC GCG GCC TCA C-3' (SEQ ID NO: 21) and 5'-G GGA ATT CAG GTC CTC TCC CCC GC-3' (SEQ ID NO: 22) (bold sequences complement DEBS sequence). The PCR amplicon was inserted after M2 using the engineered sites, yielding pST179. This plasmid, pRSG34, encodes module 3 of DEBS (M3) with its own N-terminal linker and with the thioesterase fused to the C-terminus. Its construction has been described previously (id.). Plasmid pST132 encodes a derivative of M3+TE, where the natural N-terminal linker of pRSG34 has been replaced with the N-terminal linker of module 5 of DEBS (M5). This substitution required the replacement of the NdeI-BsaBI fragment of pRSG34 with the corresponding fragment from pJRJ10 (Jacobsen, J. R., et al., (1998) *Biochemistry* 37, 4928–4934). All constructs were cloned into pET-21c (Novagen) vectors for expression in *Escherichia coli*.

Strain and Culture Conditions. Expression of the desired proteins was achieved by transforming the above plasmids into an engineered strain of *E. coli* BL21(DE3) containing the sfp phosphopantetheinyl transferase gene from *Bacillus subtilis* (Lambalot, R. H., et al., (1996) *Chem. Biol.* 3, 923–936). The sfp gene product was required to posttranslationally modify the acyl carrier protein (ACP) domains by phosphopantetheinylating the apo-ACP (Gokhale, R. S., et al., (1999) *Science* 284, 482–485). Cells containing the expression plasmids were selected with carbenicillin and used to inoculate a 10–20 mL LB medium starter culture grown at 37° C. After 6 h, the cells were pelleted and used to inoculate two 2 L flasks containing 1 L of LB medium each. The flasks were shaken at 250 rpm at 37° C. until the culture optical density at 600 nm (OD$_{600}$) was 0.6. The flasks were placed in a water bath to cool the cells to 22 C (ca. 10 min) and then induced with 0.5 mM isopropyl β-D-thiogalactopyranoside at an OD$_{600}$=0.8. Flasks were then stirred at 22–24° C. for 10–14 h.

Purification of Proteins. After induction, the cells were harvested via centrifugation and washed in 50 mM Tris (pH 8) and 1 mM ethylenediaminetetraacetic acid (EDTA) before being resuspended in disruption buffer [200 mM sodium chloride, 200 mM sodium phosphate, 2.5 mM dithiothreitol (DTT), 2.5 MM EDTA, 1.5 mM benzamidine, pepstatin and leupeptin (2 mg/L), and 30% (w/v) glycerol]. The cell suspension was lysed at 1250 psi using a French press and then centrifuged. Polyethylenimine was added to the supernatant to 0.15% to precipitate nucleic acids. Following the centrifugation (20 min at 33300 g) to remove the nucleic acids, ammonium sulfate was added to the supernatant until a 50% (w/v) saturation was achieved and allowed to precipitate for 2–3 h. The pellet following a 45 min centrifugation (33300 g) was resuspended in buffer A [100 mM sodium phosphate (pH 7.2), 2 mM DTT, 1 mM EDTA, and 20% (v/v) glycerol]. The resulting suspension was applied in 2.5 mL aliquots to a 9.1 mL gel filtration column (PD-10, Pharmacia) equilibrated with buffer B (buffer A+1 M ammonium sulfate) and eluted in 3.5 mL of buffer B. This eluant was applied to a 30 mL hydrophobic-interaction column (Butyl-Sepharose 4 FastFlow, Pharmacia) at 1 mL/min. Elution was performed at 1 mL/min with stepwise changes in buffer starting from 100% buffer B, to 40%, 20%, and 0%. Steps were made when the absorbance at 280 nm approached baseline. Fractions were 10 mL, and those containing the protein of interest (typically eluted with 0% buffer B) were pooled and applied to an anion-exchange column (Resource Q, 6 mL, Pharmacia) at 1 mL/min. A gradient of 0–0.15 M NaCl in buffer A was run at 1 mL/min for 3 column volumes, followed by a gentle gradient of 0.15–0.30 M NaCl at 1 mL/min for 10 column volumes. Fractions of 2 mL were collected, and those containing concentrated protein (typically 0.22–0.25 M NaCl) were pooled and further concentrated on Centriprep 50 membranes (50 kDa molecular mass cutoff; Amicon) to a concentration of 0.1–4 mg/mL. Protein concentrations were measured via the modified Lowry assay (Sigma) and densitometric analysis of SDS-PAGE gels stained with Coomassie Blue. On the basis of the densitometry data, all proteins were determined to be >90% pure.

In Vitro Polyketide Production. Assays of individual modules contained 1.0 μM protein, 1–10 mM N-acetylcysteamine thioester of the "natural" (2S,3R)-2-methyl-3-hydroxypentanoic acid diketide (NDK) (1), 4 mM NADPH, 440 mM sodium phosphate, 1 mM EDTA, 2.5 mM dithiothreitol (DTT), and 20% w/v glycerol, pH 7.2, in 80 μL. Reactions with M2 or M2(4) included 0.3 mM $^{14}$C-methylmalonyl-CoA (specific activity adjusted to 10.4 mCi/mmol), and those with M3+TE or (5)M3+TE included 0.5 mM $^{14}$C-methylmalonyl-CoA (specific activity reduced to 1.1 mCi/mmol). [M2(4) refers to a derivative of M2 in which the C-terminal linker has been replaced with its counterpart from module 4, whereas (5)M3 refers to a derivative of M3 in which the N-terminal linker has been replaced with its counterpart from module 5 (see FIG. 4).] Both concentrations of methylmalonyl-CoA were saturating, but different concentrations were needed due to the disparate rates of turnover between the modules with and without the thioesterase. The reaction mixtures were preincubated to 30° C. and started with the addition of the methylmalonyl-CoA. The reactions were incubated at 30° C., and at three to four time points, 20 μL aliquots were removed and quenched with ethyl acetate, which was extracted twice (450 μL total) to isolate the polyketide products. The ethyl acetate layers were pooled, dried in vacuo, and applied to an analytical thin-layer chromatography (TLC) plate (Si250F; Baker). The TLC plate was developed using 50% ethyl acetate in hexanes as the mobile phase (triketide ketolactone 4, $R_f$=0.5; triketide lactone 3, $R_f$=0.4) and then visualized by electronic autoradiography (InstantImager, Packard Instruments). Product formation was quantified by comparison with standards of the labeled methylmalonyl-CoA. The identity of products 2, 3, and 4 has been unambiguously established in earlier in vitro enzymatic studies (Pieper, R., et al., (1995) *J. Am. Chem. Soc.* 117, 11373–11374; Pieper, R., et al., (1997) *Biochemistry* 36, 1846–1851) and was reconfirmed by chromatographic comparison with authentic reference samples.

Assays of M2 and M3+TE contained 1.0 μM M2 and 0.4–4 μM M3+TE, 7 mM NDK, 0.5 mM $^{14}$C-methylmalonyl-CoA (specific activity reduced to 3.4 mCi/mmol), 4 mM NADPH, 440 mM sodium phosphate, 1 mM EDTA, 2.5 mM DTT, and 20% w/v glycerol, pH 7.2, in 70 μL. Assays of M2(4) and (5)M3+TE were identical, except they contained 0.5 μM M2(4), 0.5–5 μM (5)M3+TE, and 0.4 mM $^{14}$C-methylmalonyl-CoA (specific activity reduced to 6.2 mCi/mmol). The concentration of M2(4) was limiting in order to facilitate its saturation with (5)M3+TE. The reactions were prewarmed at 30° C. and initiated by the addition of the methylmalonyl-CoA. As described above, 20 μL aliquots were removed at various time points and processed. Extracts loaded onto TLC plates were separated using either 80% ethyl acetate in hexanes or 5% methanol in dichloromethane, both of which allowed identification of the tetraketide lactone 2 and the triketide lactones 3 and 4.

Inhibition of Tetraketide Production. The ability of the synthetic peptide to inhibit the transfer reaction, and thus the production of tetraketide, was tested under the same reaction conditions described for the two module coincubations. The concentrations of M2 and M3+TE were both 1.0 μM, and the concentrations of M2(4) and (5)M3+TE were 0.5 and 1.0 μM, respectively. The only difference was the addition of the peptide at concentrations ranging from 1 to 100 μM to the assay containing M2 and M3+TE [or alternatively M2(4) and (5)M3+TE]. For greater accuracy, each inhibition assay was performed side by side with a control lacking inhibitor. The effect of the inhibitor was thus determined by dividing the inhibited rate by the control rate.

Kinetic Analysis. For individual modules, the steady-state turnover number was determined from the time course of triketide formation, normalized to the concentration of protein. The dependence of the rate on substrate concentration was measured by varying the concentration of NDK while maintaining saturating levels of NADPH and methylmalonyl-CoA. From these data, the $k_{cat}$ and $K_M$ were calculated by fitting the normalized v versus [S] plots to the Michaelis-Menten equation.

For tetraketide formation, the rate of production of tetraketide was recorded for varying concentrations of M3+TE [or (5)M3+TE] at a fixed concentration of M2 [or M2(4)] and saturating concentrations of substrates. By fitting the rate dependence of tetraketide to a saturation curve, the maximal velocity ($v_{max}$) of tetraketide production was determined, and was assumed to represent the case where every M2 homodimer was productively associated with an M3+TE homodimer. Thus, the affinity of this protein-protein interaction could be calculated from the rate of tetraketide formation, as represented in Equation 1

$$v = k_{cat}[M2\text{-}M3] \tag{1}$$

([M2], [M3], and [M2-M3] refer to the concentrations of M2, unbound M3+TE, and the M2/M3+TE complex, respectively). Since [M2-M3] is related to the $K_D$ of M2 and M3+TE as shown in Equation 2, $$K_D = \frac{[M2][M3]}{[M2\text{-}M3]} \tag{2}$$

which can be rearranged to yield Equation 3, $$[M2\text{-}M3] = \frac{[M2]_0[M3]}{K_D + [M3]} \tag{3}$$

where $[M2]_0$=total concentration of M2, the velocity of tetraketide production can be defined relative to the $K_D$:

$$v = \frac{v_{max}[M3]}{K_D + [M3]} \tag{4}$$

where $v = k_{cat}[M2\text{-}M3]$ and $v_{max} = k_{cat}[M2]_0$. Thus, fitting of the v versus [M3] plot (which is equivalent to the bound M3+TE versus free M3+TE plot used for Scatchard analysis) to Equation 4 allowed determination of the $K_D$ for M2 and M3+TE association.

CD Spectroscopy. The CD spectrum of the M3 N-terminal peptide was recorded in a 1-mm path-length cell at a sample concentration of 100 μM in phosphate-buffered saline (PBS; 0.15 M KCl, 25 mM phosphate, pH 6.9). Measurements were made using an Aviv 62DS spectropolarimeter. Concentration was determined by tyrosine absorbance at 275 nm in 8 M guanidine hydrochloride.

Kinetic Analysis of Individual Modules. To directly measure the effect of linker replacement, individual modules with substituted linkers were kinetically characterized using the natural diketide (NDK) as substrate. The only difference between the M3+TE and (5)M3+TE proteins was that the former contained the N-terminal linker of M3, whereas the latter contained the N-terminal linker of M5. As shown in FIG. 5, the modules displayed very similar kinetics. The calculated $k_{cat}$ values were 0.71±0.1 and 0.68±0.1 min$^{-1}$ and the $K_M$ values were 2.8±1.5 and 2.5±1.0 μM for M3+TE and (5)M3+TE, respectively. Similar experiments were performed to compare M2 and M2(4), where the C-terminal linker of M2 had been swapped. Since the rate of turnover of NDK to triketide lactone 3 by module 2 lacking the fused thioesterase domain was low, however, only an approximate $k_{cat}$ could be estimated [0.02 and 0.03 $min^{-1}$ for M2 and M2(4), respectively]. Thus, replacement of either the N-terminal or the C-terminal linker of a module does not appear to affect its intrinsic catalytic properties.

Kinetic Analysis of M2-M3 Coincubations. Upon coincubation of M2 and M3+TE in the presence of NDK, methylmalonyl-CoA, and NADPH, tetraketide lactone 2 was formed (FIG. 6) with a maximum rate constant of 0.27±0.01 $min^{-1}$. The $k_{cat}$ of M2 with M3+TE was determined from the saturation curve determined using a fixed concentration of M2 and a variable concentration of M3+TE and correlated well with an earlier measurement of 0.23 $min^-$ for formation of the same tetraketide by DEBS1 and M3+TE (Pieper, R., et al., (1997) *Biochemistry* 36, 1846–1851). Thus, the M2 protein described here appears to be a viable alternative to DEBS1 as a donor of the triketide intermediate to M3+TE. From the saturation curve, a $K_D$ of 1.1±0.1 μM for the M2-M3+TE interaction could be estimated (FIG. 7A; see also Materials and Methods section). Again, this value compares well with the previously reported value of 2.6 μM for DEBS1 and M3+TE (Gokhale, R. S., et al., (1999) *Chem. Biol.* 6, 117–125).

Analogous to the above study, coincubation of M2(4) with (5)M3+TE allowed examination of the effects of the transplanted DEBS2-DEBS3 linker pair (FIG. 4) on chain transfer between modules 2 and 3. The efficiency of chain transfer in the presence of this alternative linker pair (FIG. 6D) was established by measuring the same parameters associated with synthesis of the tetraketide lactone 2 [$k_{cat}$ of 0.74±0.06 $min^{-1}$ and a $K_D$ of 2.1±0.4 μM (FIG. 7B)].

Effects of Mismatched Linker Pairs. In contrast to the above studies with M2 and M3+TE (FIG. 6A) or M2(4) and (5)M3+TE (FIG. 6D), both of the noncomplementary coincubations [M2 with (5)M3+TE (FIG. 3B) and M2(4) with M3+TE (FIG. 6C)] produced the tetraketide lactone 2 at severely compromised rates. The highest rate constants that could be measured with either mismatched system were in the range of 0.02–0.03 $min^{-1}$. Given these low rate constants, the dependence of rate on protein concentration could not be measured. As might be expected, the rate of production of ketolactone 4 increased markedly in both cases relative to the matched incubations above (data not shown), since module 3 remained active in these mismatched coincubations.

Inhibition of Tetraketide Production by a Synthetic Peptide. Sequence analysis using the CoilScan program (Lupas, A., et al., (1991) *Science* 252, 1162–1164; Lupas, A., (1996) *Methods Enzymol.* 266, 513–52) revealed that the N- and C-terminal interpolypeptide linkers of DEBS contained 15–20 residue segments with strong propensity to assume a coiled-coil structure. Since the N-terminal linker of module 3 is relatively short (31 residues), a peptide corresponding to this sequence was synthesized (see Materials and Methods). As shown in FIG. 8, this linker could inhibit the formation of 2 in the presence of M2 and M3+TE in a concentration-dependent manner. To test the specificity of this peptide inhibitor, a similar assay was also conducted in the presence of M2(4) and (5)M3+TE. No inhibitory effect was observed at peptide concentrations up to 100 μM (FIG. 8). Furthermore, the peptide also showed no inhibitory effect upon individually assayed modules, including M3+TE. Thus, isolated peptide linkers appear to be selectively capable of competing for their cognate module-bound partners without affecting their individual catalytic activities.

The N-terminal linker peptide of M3 was analyzed via circular dichroism (CD) to assess its α-helical character. As shown in FIG. 9, the spectrum shows the 208 and 222 nm absorbances characteristic of α-helices. The magnitude of these peaks allowed us to estimate that the peptide was approximately 50% helical (Chen, Y. H., et al., (1974) *Biochemistry* 13, 3350–3359). The CD of the peptide appeared invariant with peptide concentration, salt concentration, and phosphate concentration.

Earlier studies suggested the role of structurally intact intermodular linkers in facilitating chain transfer between noncovalently associated modules of PKSs (Gokhale, R. S., et al., (1999) *Science* 284, 482–485). Here we have extended and elaborated these findings in several significant ways. First, our results have vividly demonstrated the selectivity associated with linker-mediated chain transfer (FIG. 6). Although intermodular chain transfer can occur between modules possessing mismatched linker pairs, a serious kinetic penalty is paid. In contrast, heterologous matched linker pairs can facilitate chain transfer between modules as efficiently as natural pairs. Second, the selectivity associated with linker pair interactions suggests that they might play a key role in the transient assembly of functionally paired complexes of the three DEBS proteins (Aparicio, J. F., et al., (1994) *J. Biol. Chem.* 269, 8524–8528; Pieper, R., et al., (1995) *Nature* 378, 263–266). In support of this hypothesis, we have demonstrated that a peptide mimic of the N-terminal linker of DEBS2 can inhibit chain transfer mediated by the linker pair at the DEBS1-DEBS2 interface but not by the linker pair at the DEBS2-DEBS3 interface (FIG. 8). Third, we show that the N-terminal linker peptide of DEBS2 has significant (ca. 50%) helical content (FIG. 9). This observation is consistent with secondary structure analyses of individual linker sequences, which previously indicated a propensity of these sequences to assume coiled-coil conformations.[2] It should be emphasized that, in order for a coiled-coil motif to facilitate noncovalent docking of two modules, the heterodimer (or heterooligomer) formed by associations between the C-terminal linker and N-terminal linker must be thermodynamically more favorable than either homodimer. Although the data shown in FIG. 9 show helical content of a linker, it does not provide evidence for formation of a coiled-coil structure. Thus, direct evidence for the existence of coiled coils at intermodular interfaces, as well as their implications for selective chain transfer, remains to be obtained.

Earlier studies have demonstrated the importance of two additional molecular recognition events in controlling the overall programming and specificity of PKSs. First, individual modules can discriminate among alternative incoming substrates (Wu, N., et al., (2000) *J. Am. Chem. Soc.* 122, 4847–4852); this selectivity appears to reside within the individual ketosynthase domains (Jacobsen, J. R., et al., (1997) *Science* 277, 367–369; Chuck, J., et al., (1997) *Chem. Biol.* 4, 757–766). Second, ketosynthase and ACP domains appear to have some degree of mutual recognition (Dreier, J., et al, (1999) *J. Biol. Chem.* 274, 25108–25112; Ranganathan, A., et al., (1999) *Chem. Biol.* 6, 731–741). Both of these recognition properties are localized within highly conserved and catalytically critical parts of the large PKS modules. Here we define and dissect a third element of selectivity. In contrast to the previously recognized factors influencing molecular recognition by PKS components, linker-mediated intermodular interactions have been localized to short, nonconserved regions that lie outside the core modules and have no influence on the intrinsic chemistry of the individual modules.

EXAMPLE 7

Methods Directed Towards Assessing the Effects of Protein-Protein Interactions and Enzyme-Substrate Interactions in the Channeling of Intermediates Between Polyketide Synthase Modules Construction of Plasmids. The gene encoding ACP4(4) was amplified as an NdeI-EcoRI PCR fragment (523 bp) using the primers 5'-CCATATGGTGGTCGACCGGCTCG-3' and 5'-GAATTCCTACAGGTCCTCTCCCCC-3' (sequences complementary to DEBS shown in bold). The PCR product was cloned into pET28a (Novagen) to yield plasmid pNW8. Plasmid pST157 encodes a bimodular fusion between module 1 of DEBS1 and module 5 of DEBS3, with the thioesterase domain fused downstream of module 5 ("M1+M5+TE"). This fusion, which was engineered by taking advantage of the natural, conserved BsaBI sites located at the start of the KS domains of modules 2 and 5, also includes the loading didomain of DEBS1. The "linker" sequence that covalently bridges the fused modules is the natural sequence between modules 1 and 2, as in DEBS1. The fusion junction between module 5 and the thioesterase domain is identical to that in plasmid pRSG46.[23] Similarly, plasmid pST92 encodes an "M1+M6+TE" bimodular fusion. Its construction, which is completely analogous to that of pST157, involves introduction of this bimodular PKS gene from pST96, Gokhale, et al., *Science* 1999, 284, 482–485, as an NdeI-EcoRI into pET-21c (Novagen). The construction of genes encoding (5)M2+TE, (3)M3+TE, (5)M5+TE, and (5)M6+TE (pRSG64, pRSG64, pRSG46, and pRSG54, respectively) have been described previously, id., as well as the construction of a gene encoding (5)M3+TE (pST132). See Tsuji, et al., *Biochemistry* (2001) 40:2326–2331.

Expression and Purification of Proteins. All individual modules were expressed and purified as previously described. Wu, et al., *Am. Chem. Soc.* 2000, 122, 4847–4852. The bimodular proteins were expressed as C-terminal $His_6$-tagged fusion proteins, and their expression and purification schemes were identical to those previously described for the individual modules (id.), yielding 0.2 mg/L culture of purified M1+M5+TE and 1 mg/mL culture of purified M1+M6+TE. ACP4(4) was expressed by transforming pNW8 into *E. coli* BL21(DE3) cells (Novagen), which were then grown in LB at 37° C. to $OD_{600}$) 0.7–0.8. BL21(DE3)/pNW8 was induced overnight with 1 mM IPTG at 30° C. The cells were harvested by centrifugation, washed with TE buffer, and then resuspended in disruption buffer (100 mM $NaH_2PO_4$ (pH 7.2), 100 mM NaCl, 1.2 mM DTT, 1.2 mM EDTA, 0.7 mM benzamidine, 1 mg/L pepstatin, 1 mg/mL leupeptin, and 15% glycerol) before lysis by French press. Following removal of the cell debris by centrifugation, the supernatant was treated with 0.1% (w/v) PEI to remove nucleic acids followed by a 55% $(NH_4)_2SO_4$ precipita-tion. The resulting $(NH_4)_2SO_4$ pellet was resuspended in 100 mM $NaH_2PO_4$ (pH 7.2), 2.5 mM DTT, 1 mM EDTA, 20% glycerol (buffer A). This suspension was desalted on a PD-10 gel filtration column (Amersham Pharmacia Biotech AB) equilibrated with 10 mM imidazole in 50 mM Tris (pH 8.0), 1 M NaCl, 20% glycerol (buffer B), and the eluant was loaded at 1 mL/min onto a Flex-column (Kontes) packed with 5 mL of Ni NTA-Superflow resin (Qiagen) using a peristaltic pump. After being washed with 35 mM imidazole in buffer B for ACP4-(4), the $His_6$-tagged protein was eluted from the resin with 90 mM imidazole in buffer B. The appropriate fractions were concentrated, and the buffers were exchanged to buffer A+1.5 M $(NH_4)_2SO_4$ in Centriprep 10 spin columns (Amicon). Using an Akta FLPC system (Amersham Pharmacia Biotech AB), the concentrated protein was loaded at 1 mL/min onto a XK 16/20 column packed with 30 mL of Phenyl Sepharose High Performance resin and equilibrated with the same buffer. A gradient from 750 mM $(NH_4)_2SO_4$ to 0 mM $(NH_4)_2SO_4$ in buffer A was applied which eluted the protein at 0 mM $(NH_4)_2SO_4$. The appropriate fractions were concentrated in Centriprep 10 spin columns to yield approximately 10–15 mg/L of purified protein which was flash frozen and stored at –80° C. The mass of apo-ACP4(4) was confirmed by MALDI-MS (calculated mass: 20492, observed mass: 20507). (MW—methionine) was also observed.

Synthesis of CoA Thioester Diketides. The carboxylic acids of the diketides were synthesized as previously described. Harris, et al., *J. Chem. Res. (S)* 1998, 6, 283. They include the (2S,3R), (2R,3S), (2R,3R), and (2S,3S) diastereomers of 2-methyl-3-hydroxy-pentanoic acid. These carboxylic acids were converted to CoA thioesters 5a–d under the following conditions. See Belshaw, et al., *Science* 1999, 284, 486–489; Robertson, et al., *J. Am. Chem. Soc* 1991, 113, 2722–2729. Carboxylic acid (3.4 mg, 26 μmol), CoASH (sodium salt, 1.1 equiv, Sigma), and PyBOP (1.5 equiv, Novabiochem) were dissolved in 0.39 mL of THF and 0.39 mL of 4% $K_2CO_3$ and stirred under argon for 40 min. The reaction mixture was diluted to up 5 mL with H2O and injected onto a Beckman Ultrasphere $C_{18}$ HPLC column (250×10 mm) equilibrated with 50 mM $NaH_2PO_4$ (pH 4.2) in 10% $MeOH/H_2O$. Using a 10 mL/min linear gradient over 30 min to 50 mM NaH2PO4 (pH 4.2) in 80% $MeOH/H_2O$, the CoA thioesters eluted at 55% MeOH. After removal of the MeOH on a rotavap, the product was desalted by reinjection on the same column equilibrated with 10% $MeOH/H_2O$ followed by elution with 90% MeOH. The product was lyophilized and verified by MALDI-MS (theoretical mass: 881.742; observed mass: 882.191) and $^1H$ NMR (500 MHz) in $H_2O$. 5a: 0.71 (s, 3H), 0.85 (s, 3H), 0.86 (t, 3H), 1.08 (d, 3H), 1.48 (m, 2H), 2.38 (t, 2H), 2.76 (m, 1H), 2.96 (t, 2H), 3.28 (t, 2H), 3.41 (t, 2H), 3.52 (dd, 1H), 3.73 (td, 1H), 3.79 (dd, 1H), 3.98 (s, 1H), 4.20 (t, 2H), 4.55 (t, 1H), 4.79 (m, 2H), 6.13 (d, 1H), 8.21 (s, 1H), 8.51 (s, 1H). 5b: 0.72 (s, 3H), 0.86 (s, 3H), 0.89 (t, 3H), 1.11 (d, 3H), 1.44 (m, 2H), 2.40 (t, 2H), 2.79 (m, 1H), 2.97 (t, 2H), 3.30 (t, 2H), 3.43 (t, 2H), 3.52 (dd, 1H), 3.75 (td, 1H), 3.80 (dd, 1H), 3.99 (s, 1H), 4.21 (m, 2H), 4.56 (m, 1H), 4.75 (m, 1H), 4.80 (m, 1H), 6.15 (d, 1H), 8.24 (s, 1H), 8.54 (s, 1H). 5c: 0.66 (s, 3H), 0.78 (s, 3H), 0.78 (t, 3H), 0.97 (d, 3H), 1.26 (m, 1H), 1.48 (m, 1H), 2.31 (t, 2H), 2.71 (m, 1H), 2.89 (m, 2H), 3.22 (m, 2H), 3.34 (m, 2H), 3.45 (dd, 1H), 3.59 (dt, 1H), 3.72 (dd, 1H), 3.90 (s, 1H), 4.14 (m, 2H), 4.49 (m, 1H), 4.73 (m, 1H), 4.84 (m, 1H), 6.09 (d, 1H), 8.25 (s, 1H), 8.50 (s, 1H). 5d: 0.66 (s, 3H), 0.78 (s, 3H), 0.78 (t, 3H), 0.97 (d, 3H), 1.27 (m, 1H), 1.48 (m, 1H), 2.31 (t, 2H), 2.71 (m, 1H), 2.89 (m, 2H), 3.22 (m, 2H), 3.34 (t, 2H), 3.46 (dd, 1H), 3.59 (m, 1H), 3.73 (dd, 1H), 3.90 (s, 1H), 4.14 (m, 2H), 4.49 (m, 1H), 4.75 (m, 1H), 4.82 (m, 1H), 6.09 (d, 1H), 8.25 (s, 1H), 8.50 (s, 1H). Concentrations of solutions of CoA thioesters were determined by $A_{260}$ measurement and calibration against known CoA concentration standards. Yield: 9.6 μmol (37%).

Formation of Holo-ACP and Acyl-ACP from Apo-ACP. The phosphopantetheinylation reactions were catalyzed by the Sfp phos-phopantetheine transferase, see Quadri, et al., *Biochemistry* 1998, 37, 1585–1595; Weinreb, et al., *Biochemistry* 1998, 37, 1575–1584, under the following conditions: 150 μM apo ACP, 4 equiv CoASH (lithium salt, Sigma) or acyl-CoA 5a–d, 0.2 equiv Sfp in 100 mM $NaH_2PO_4$ (pH 6.6), 10 mM $MgCl_2$, 2.5 mM DTT, 20% glycerol at 37° C. for 20 min. Excess small molecules and Sfp were removed from the phosphopantetheinlyated ACPs by applying the reaction mixture with an Akta FPLC system to a 6 mL Resource Q column (Amersham Pharmacia Biotech AB) and eluting with a linear gradient from 0 mM NaCl to 500 mM NaCl in buffer A. The desired proteins eluted at 220 mM NaCl and were concentrated using Centriprep 10 spin columns. Protein concentrations were determined using a modified Lowry assay (Sigma), and the masses were confirmed by MALDI-MS or +ESI-MS (4a: observed mass=20945, calculated mass=20944; 4b: observed mass=20964; 4c: observed mass=21056; 4d: observed mass=20992).

Qualitative Substrate Incorporation Assays. The reaction buffer for the diketide incorporation assays contained 400 mM $NaH_2PO_4$ (pH 7.2), 2.5 mM DTT, 1 mM ETDA, 20% glyercol (reaction buffer C). 1 $\mu$M module, 20 $\mu$M acyl-ACP, 500 $\mu$MDL-[2-$^{14}$C]-methylmalonyl CoA (ARC), and 4 mM NADPH (Sigma) were incubated in 20 $\mu$L of the reaction buffer at 30° C. for 1.5 h. The reactions were either spotted directly onto a TLC plate (Whatman 250 $\mu$M silica gel, $UV_{254}$), or first extracted with EtOAc followed by spotting of the organic extracts on a TLC plate. The TLC plates were resolved using 60% EtOAc in hexanes, and the radioactive products were visualized on a Packard InstantImager.

Verification of Reaction Products. Triketide lactone products 3a and 3b derived from 2a (or 4a) and 2b (or 4b), respectively, have been previously verified.26 To verify the triketide lactone products 3c and 3d, reaction extracts were purified by preparative TLC. The ethyl acetate extracts of the spots corresponding to the triketide lactones were concentrated and then derivatized to TMS ethers by incubation with 50 $\mu$L of N,O-bis-(trimethylsilyl) trifluoroacetamide (Aldrich) for 30 min at room temperature. See McPherson, et al., *J. Am. Chem. Soc.* 1998, 120, 3267–3268. Injection of the sample onto a GC-MS yielded fragmentation peaks at molecular weights 73 and 171, corresponding to cleavage between the oxygen and silicon atoms, as expected. Mass spectral confirmation data of the β-ketolactone equivalents of 3c and 3d were obtained sans derivatization and by ESI-MS. The elution pattern of the triketide lactones from a chiral HPLC column is described below.

Determination of $k_{cat}$ Values. The assays for kinetic measurements were performed in reaction buffer C and with the same concentrations of NADPH and $^{14}$C-methylmalonyl CoA as for the qualitative assays. Saturating concentrations of propionyl-CoA were added to and the ACP substrates were excluded from the bimodular reactions. To quench the reactions, 20 $\mu$L reaction aliquots were mixed with 80 $\mu$L of 12.5% SDS. $k_{cat}$ values for the acyl-ACP substrates were determined by measuring steady-state saturating rates at multiple substrate concentrations (varying from 40 to 90 $\mu$M 4). For reactions that did not saturate by 90 íM of substrate, the kcat values are reported as lower limits. Workup and visualization of the reaction products were identical to those for the qualitative assays.

Determination of $kcat/K_M$ values. The assays for determination of $(k_{cat}/K_M)_{rel}$ were performed with two competing substrates in the same reaction under the same conditions as described above for the qualitative assays, except the reaction volumes were doubled to 40 $\mu$L. The data were fit into the equation where $S_A$ and $S_B$ are the two competing substrates and $P_A$ and $P_B$ are the corresponding products derived from $S_A$ and $S_B$, respectively. The unknown, absolute $k_{cat}/K_M$ values could then be obtained from known, absolute $k_{cat}/K_M$ data that had been derived directly from the initial slopes of v versus [S] plots. See McPherson, et al., *J. Am. Chem. Soc.* 1998, 120, 3267–3268. Each reaction was done in duplicate at two different ratios of substrate concentrations. The reactions were quenched with 120 $\mu$L of 12.5% SDS, and the products were extracted with 2×300 $\mu$L of EtOAc. The organic extracts were purged of highly polar compounds as well as particulates by flash chromatography through 50 $\mu$L of silica gel in a 1-mL polypropylene pipet attached to a 3-mm, 0.22-$\mu$m nylon syringe filter (Osmonics, Inc.), eluting with 1.5 mL of EtOAc. Following removal of the organic solvents, the residual extracts were resuspended in 20 $\mu$L of hexane and loaded onto a 250×4.6 mm Chiralpak AS column with the corresponding guard column (Daicel Chemical Industries) that had been equilibrated with 5% EtOH (Reagent Alcohol, Fischer) in hexane. With a flow rate of 0.8 mL/min, the products were separated using a 20 min gradient (starting at 2 min) from 5 to 15% EtOH in hexane. The reduced triketide lactone products 3a–d eluted at 20.0, 17.0, 21.5, and 18.5 min, respectively. The unreduced triketide lactone products, derived from 4c and 4d, eluted at 21.0 and 19.0 min, respectively. The appropriate fractions were collected, and the radio-active products were detected and quantified using Formula-989 liquid scintillation cocktail fluid (Packard) on a Beckman LS3801 liquid scintillation counter.

Labeling of Holo-ACP4(4) with $^{14}$C-2a Mediated by (5)M2+TE. Holo-ACP4(4) (20 $\mu$M) was incubated with 1 mM [1-$^{14}$C]-labeled 2a (custom synthesized by Amersham Pharmacia, specific activity 55 mCi/mmol) and 1 $\mu$M (5)M2+TE in reaction buffer C for 10 min at 30° C. The protein was precipitated with 75% acetone/$H_2O$ for 5 min at −80° C. After washing the pellet with 6.25% (w/v) TCA to remove excess salts followed by 500 $\mu$L of 75% acetone/$H_2O$ to remove residual, unbound 14 C-2a, the precipitated protein was resuspended in 8 $\mu$L of buffer A and 4 $\mu$L of SDS sample buffer, and resolved on a 4–20% SDS-PAGE gradient gel (Bio-Rad). The proteins were visualized with Coomassie blue stain and dried, and the radioactivity was detected either on a Packard InstantImager or by exposing the gel to X-ray film.

Nomenclature. The nomenclature used in this report for proteins containing linker regions is similar to that adopted in a previous publication. (id.) Specifically, the module of origin of the linker is placed in parentheses either before or after the name of the domain or module to which it is attached, depending on whether it is an N- or a C-terminal linker, respectively. For example, a fusion protein comprising the ACP domain from module 2 of DEBS and the C-terminal linker of module 4 is referred to as ACP2(4); likewise, a protein comprising the N-terminal linker of module 5 fused to module 6 is referred to as (5)M6.

Construction and Expression of Bimodular Enzymes. Analogous to DEBS1+TE described earlier, Cortes, et al., *Science* 1995, 268, 1487–1489; Kao, et al., *J. Am. Chem. Soc.* 1995, 117, 9105–9106, M1+M5+TE (module 1+module 5+TE) and M1+M6+TE are heterologous fusions of DEBS module 1 with DEBS modules 5 and 6, respectively. The natural linker between modules 1 and 2 in the wild-type DEBS1 protein was preserved in each case. In addition, the DEBS thioesterase (TE) domain was fused to the C termini of each downstream module to facilitate turnover by catalyzing the release of the triketide product. These two proteins were expressed as C-terminally $His_6$-tagged proteins and purified on a hydrophobic butyl sepharose column followed by a Resource Q ion-exchange chromatography to yield approximately 0.2 mg/L culture of purified M1+M5+TE and 1 mg/L culture of purified M1+M6+TE.

Kinetic Analysis of Bimodular Constructs. In earlier studies on the kinetic properties of individual modules (Wu, et al., *Am. Chem. Soc.* 2000, 122, 4847–4852), substrates were diffusively presented to the KS domain of each module as free N-acetylcysteamine (NAC) thioesters. This can be contrasted with the natural mode of chain transfer in a multimodular system, where acyl chains arrive at the KS domain via direct transfer from an upstream ACP domain (FIG. 4). To explore whether the latter mode of substrate incorporation can have kinetic benefits over the former, the rates of triketide lactone 3a synthesis by M1+M5+TE and M1+M6+TE were measured in the presence of saturating concentrations of propionyl-CoA, methylmalonyl-CoA, and NADPH. The $k_{cat}$ values for these two hybrid PKSs were determined to be 3.1±0.1 and 4.1±0.4 $min^{-1}$, respectively (FIG. 12). These parameters compare well with the maximal rate of 4.8 $min^{-1}$ for DEBS1+TE (Pieper, et al., *Biochemistry* 1997, 36, 1846–1851). In contrast, we have shown earlier that whereas module 2+TE and module 6+TE turn 2a over with comparable rate constants ($k_{cat}$=4.6 and 17 $min^{-1}$, respectively), module 5+TE is a significantly weaker catalyst for the same reaction ($k_{cat}$=0.25 $min^{-1}$). Addition of exogenous 2a to the reaction catalyzed by the bimodular proteins had no effect on their overall catalytic rates. The implications of these results to intramodular substrate channeling will be evaluated in the discussion section.

Construction and Expression of Individual ACPs. ACP4-(4) includes the entire DEBS ACP4 catalytic domain with its natural C-terminal linker. (The ACP linker is defined as the residues between the ACP consensus sequence and the C terminus of the polypeptide. See Tsuji, et al., *Biochemistry* (2001) 40:2326–2331). This gene was expressed as a 20.5 kDa N-terminally $His_6$-tagged protein to preserve the natural sequence of the C-terminal linker. ACP4(4) was purified by affinity chromatography on a nickel column followed by a hydrophobic phenyl sepharose column to yield approximately 10–15 mg/L culture of purified apoprotein.

Chemoenzymatic Synthesis of Acyl-ACPs. Preparations of the CoA thioesters of the natural diketide substrate of module 2, its enantiomer, its C-3 epimer, and its C-2 epimer (FIG. 11) were carried out as described in the Materials and Methods section. Phosphopantetheinylation of apo-ACP4(4) was cata-lyzed by Sfp (Quadri, et al., *Biochemistry* 1998, 37, 1585–1595; Weinreb, et al., *Biochemistry* 1998, 37, 1575–1584), (FIG. 10C, first reaction) to generate acyl-ACP4(4) adducts 4a–d. Purification of these acyl-ACPs, as described in the Materials and Methods section, led to >95% pure materials as judged from SDS-PAGE. Complete phospho-pantetheinlyation was verified by MALDI-MS or ESI-MS.

Qualitative Assays of Diketide Incorporation by Acyl-ACPs. The acyl-ACP4(4) adducts 4a–d were incubated individually with (5)M2+TE, (5)M5+TE, and (5)M6+TE in the presence of saturating concentrations of $^{14}$C-methylmalonyl CoA extender unit and NADPH. For a given acyl-ACP, the products from modules 2+TE, 5+TE, and 6+TE were expected to be identical (FIG. 11), since the modules catalyze the same set of reactions with identical stereocontrol (albeit normally on very different natural substrates). Both 4a and 4b were accepted and extended by all three modules. Likewise, the corresponding NAC-thioesters 2a and 2b have been shown to be substrates for the three modules.[26] Remarkably, however, 4c and 4d were also substrates for the three modules, even though no turnover of the corresponding NAC thioesters 2c and 2d was detected in the case of any module, Wu, et al., *Am. Chem. Soc.* 2000, 122, 4847–4852 (It should be noted that elongation of 4c and 4d by modules 5+TE and 6+TE yielded minor quantities of unreduced triketide lactones, indicating less efficient β-ketoreductase activity on these two anti-diketide substrates than on the two syn-diketide substrates.). Consistent with previous linker studies,[23,27] while all four acyl-ACP adducts were observed to be substrates for (5)M3+TE, no product formation was observed from the incubation of any of the acyl-ACP adducts with (3)M3+TE, even though 2a and 2b have previously been shown to be readily incorporated and elongated when presented to either module 3+TE derivative, Wu, et al., *Am. Chem. Soc.* 2000, 122, 4847–4852; Tsuji, et al., *Biochemistry* (2001) 40:2326–2331. Thus, matched linker pairs appear to be capable of enhancing the efficiency with which otherwise poor substrates can be channeled between modules. Conversely, mismatched linkers can present a major barrier to the channeling of otherwise acceptable substrates between modules. Control studies performed with 2a and 5a showed that the two compounds are approximately equivalent substrates for the same modules (data not shown). From the amount of product detected in these ACP-mediated reactions, the efficiency of the PKS-catalyzed reaction could be estimated. Under typical assay conditions (20 $\mu$M 4 and 1 $\mu$M (5)M5+TE), 70% of the acyl-ACP was converted into triketide lactone in 1 h. Two conclusions can be drawn from this result. First, acyl-ACPs are significantly superior substrates to acyl-NAC thioesters. (Typically, millimolar concentrations of the NAC thioester must be used to detect comparable amounts of product under otherwise similar assay conditions.) Second, the assay system described in FIG. 11 allows for monitoring multiple turnovers of the enzyme. Indeed, as described below, in all cases the maximum rates of consumption of the acyl-ACP substrates were comparable to or higher than the maximum rates of consumption of their NAC thioester counterparts (see below). Therefore, the association of the donor ACP and the acceptor module must be transient, and the dissociation rate constant of the ACP from the module must be significantly faster than the slowest step in the module-catalyzed elongation sequence.

Kinetic Analysis of Incorporation of Diketides from Acyl-ACPs. The $k_{cat}/K_M$ values for the reactions of 4a and 4b with (5)M2+TE, (5)M5+TE, and (5)M6+TE are shown in FIG. 13. Since full saturation curves could not be obtained for the ACP-bound substrates for technical reasons, the $k_{cat}/K_M$ value for 4b was derived by competitive assay against 2a (whose absolute $k_{cat}/K_M$ value was derived from the initial slope of the v versus [S] saturation curve). Likewise, the $k_{cat}/K_M$ value for 4a was derived by competitive assay against 4b. Several observations are noteworthy regarding the data summarized in FIG. 13. First, 2a and 4a are significantly better substrates than 2b and 4b for each module. In addition, the improvement in specificity for an acyl-ACP adduct over its NAC thioester counterpart is particularly pronounced in cases where the NAC thioesters are exceptionally poor (e.g., module 2+TE-catalyzed elongation of 4b versus 2b, module 5+TE-catalyzed elongation of 4a versus 2a, and especially module 5+TE-catalyzed elongation of 4b versus 2b). The implications of these observations are elaborated in the Discussion section.

To quantify the kinetic advantage of channeling in the above assay system, the $k_{cat}$ values for the reactions of 4a–d with modules 2+TE, 5+TE, and 6+TE were measured (FIG. 14). Kinetic measurements were performed at substrate concentrations between 40 and 90 $\mu$M of each acyl-ACP substrate. For reactions that yielded measurable quantities of unreduced triketide lactone products (i.e., elongation of 4c and 4d by modules 5+TE and 6+TE), both reduced and unreduced products were combined and included for calculations of the kinetics parameters. Except for the reaction of 4a with module 2+TE, none of the substrates saturate the enzymes in this concentration range, and thus, the $k_{cat}$ values are reported as lower bounds. Comparison of the $k_{cat}$ values of the acyl-ACP forms of the four diastereomeric diketides with those from the corresponding reactions involving NAC thioesters substrates (which are also shown in FIG. 14) (Wu, et al., *Am. Chem. Soc.* 2000, 122, 4847–4852) affords two interesting observations. First, in those cases where the NAC thioester is a reasonably good substrate (e.g., module 2+TE- or module 6+TE-catalyzed elongation of 2a and 4a), the maximal reaction rates are comparable regardless of whether the acyl chain is bound to NAC or an ACP with a matched linker. In contrast, where the NAC thioester is an inferior substrate (e.g., module 2+TE-catalyzed elongation of 2b and 4b, M5+TE-catalyzed elongation of 2a and 4a, module 5+TE-catalyzed elongation of 2b and 4b, and elongation of 4c and 4d by any of the modules), tethering the same acyl chain to an ACP with a matched linker can result in significant improvements in $k_{cat}$. Second, the maximal rate of turnover of 2a and 4a is significantly greater than that of 2b and 4b for all tested modules. Again, the implications of these findings are discussed below.

Investigation of the Reversibility of the Donor ACP to Acceptor KS Transfer Reaction. Ordinarily, the flow of intermediates in a metabolically active PKS is vectorial. A possible mechanism for such directionality could be that, once an acceptor KS is acylated with the incoming chain, conformational changes in the module prevent the pantetheine arm of the donor ACP from accessing the active site again. To test whether this may be the case, holo-ACP4(4) was incubated with $^{14}$C-2a in the presence and absence of (5)M2+TE (FIG. 15). The ACP was radiolabeled only in the reaction containing (5)-M2+TE. (As expected, (5)M2+TE was also labeled.) When methylmalonyl CoA extender units and NADPH were added to induce catalytic activity of the module, (5)M2+TE dependent labeling of ACP4(4) was also observed, but the degree of labeling was considerably reduced. Thus, there does not appear to be an absolute barrier to the back-transfer of an acyl chain from a KS to the ACP of the preceding module.

We have previously investigated the substrate specificity of individual modules of DEBS using diketide substrates activated as N-acetylcysteamine (NAC) thioesters (FIG. 10A) (id.). The diketides included in the previous study were the four diastereomeric forms of the natural substrate for module 2 (FIG. 11). These substrates were assayed against DEBS modules 2, 3, 5, and 6—each with a TE domain fused to the C terminus to facilitate turnover—and steady-state kinetic parameters were determined for each substrate-enzyme combination. The substrate specificity profiles (as reflected in the $k_{cat}/K_M$ values) for the four enzymes were found to be remarkably similar in that all of the modules preferred 2a over 2b, and, within detection limits, neither of the two anti-diketides 2c or 2d was observed to be a substrate for any of the modules.

The preference of 2a over its enantiomer 2b for all modules was especially intriguing in light of the fact that the natural substrates for modules 3 and 6 share more structural similarities to 2b than to 2a. One explanation for this discrepancy was that the NAC thioester-based assay system (FIG. 10A) may not entirely represent the mechanism of acylation of a multimodular system. While NAC thioesters substrates must be loaded diffusively onto the KS of a module (FIG. 10A), polyketide intermediates are channeled from the ACP of one module to the KS of the downstream module via covalent transfer. Substrate channeling in a multimodular system can occur either between two modules on the same polypeptide (e.g., between modules 1 and 2; FIG. 10B), or between two modules on separate polypeptides (e.g., between modules 2 and 3; FIG. 10C). Further evidence that protein-protein interactions may influence the substrate specificities of individual modules emerged from previous experiments suggesting, that inter-polypeptide linkers—defined as the highly variable regions outside the consensus sequences of the modules—are involved in mediating selective intermodular chain transfer, Gokhale, et al., *Science* 1999, 284, 482–485; Tsuji, et al., *Biochemistry* (2001) 40:2326–2331. To investigate the balance of protein-protein interactions and enzyme-substrate interactions in controlling polyketide chain elongation, two assay systems that take intermodular interactions into account were used in this study.

Kinetic Channeling in Intrapolypeptide Chain Transfer. In the first system (FIG. 10B), the effect of substrate channeling between two modules within the same polypeptide was investigated. More specifically, in the context of the bimodular constructs M1+M2+TE (DEBS1+TE), M1+M5+TE, and M1+M6+TE, DEBS modules 2, 5, and 6 were examined for their abilities to accept and elongate the natural diketide intermediate that was passed from a covalently attached module 1. The turnover number of M1+M5+TE was comparable to that of M1+M6+TE or the "wild-type" M1+M2+TE. In contrast, when primed diffusively by 2a, the maximum catalytic rate of module 5+TE is significantly reduced compared to that of module 2+TE or module 6+TE. This disparity indicates that covalent connection of modules can have a beneficial kinetic effect and hinted that, in addition to physical channeling of intermediates, multimodular PKSs are also capable of kinetic channeling of intermediates. However, since the only incoming substrate that could be tested using this assay system was the natural diketide, a better assay system was needed to explore the role of kinetic channeling more generally.

Kinetic Channeling in Interpolypeptide Chain Transfer. The minimal donor protein requirement for substrate channeling to an acceptor module was postulated to be an ACP domain with an appropriate C-terminal linker. Therefore, we constructed, expressed, and purified the ACP4 domain and its natural C-terminal linker as an individual polypeptide. A variety of acyl groups were then covalently attached to the phosphopantetheine arm of holo-ACP4(4) via a chemoenzymatic procedure (FIG. 10C, first reaction). The resulting acyl-ACP4(4) adducts 4a–d were tested for their ability to transfer the attached diketides from ACP4(4) to the KS of an acceptor module (FIG. 10C, second reaction), where they could then undergo standard chain elongation to yield a triketide lactone (FIG. 10C, third reaction). The small size of the ACP4(4) protein, together with high expression levels of soluble protein in *Escherichia coli*, allowed production of reagent quantities of this protein for use as a substrate in multiple turnover assays. The requirement of both an ACP and the linker was highlighted by the fact that corresponding CoA thioesters exhibited comparable kinetic parameters and that mismatched linkers led to a dramatic reduction in turnover efficiency in the case of module 3+TE. The latter feature is consistent with the linker hypothesis developed earlier. Id. Although the precise $K_M$ values for individual acyl-ACP substrates could not be measured in many cases, in all cases they were estimated to be approximately 2–3 orders of magnitude lower than the reported $K_M$ values for the corresponding NAC thioester reactions (micromolar for acyl-ACPs versus millimolar for acyl-S-NACs), thus making acyl-ACPs excellent substrates for individual PKS modules.

Implications of the Interpolypeptide Transfer Kinetics Data. The establishment of the acyl-ACP-based assay system allowed us to address two important questions regarding the relative balance of protein-protein interactions and enzyme-substrate interactions in multimodular systems. First, is the universal preference among the three tested modules for 2a over 2b preserved when the same substrates are delivered as acyl-ACP adducts? And second, under saturation conditions, can kinetic channeling of these diketide substrates be observed for any module?

As seen in FIG. 13, the preference for the (2S,3R)-diastereomer over its enantiomeric (2R,3S)-diastereomer by all modules is preserved regardless of whether the substrate is loaded by a channeling mechanism or by a diffusive mechanism. This conserved preference suggests that the catalytic steps in a given module that discriminate between different substrates remain unchanged whether modules are primed diffusively or by a channeling mechanism and that for module 2, at least, the most likely source of discrimination is the KS acylation step. Furthermore, the turnover numbers of the individual enzyme-catalyzed reactions reported in FIG. 14 make a strong case for kinetic channeling in multimodular PKSs. When saturating concentrations of 2b are co-incubated with M5+TE in the presence of methylmalonyl-CoA and NADPH, the elongation rate constant is only 0.02 min$^{-1}$. In contrast, when the same reaction is monitored using 4b as a substrate, the elongation rate constant ($k_{cat}$) increases at least 25-fold. Similarly, a maximal rate increase of greater than 40-fold is observed in the elongation of 4a versus 2a by M5+TE. The effect may be even more pronounced for the two anti-diketides, whose elongation rates are below detectable limits (<0.01 min$^{-1}$) when presented as NAC thioesters 2c and 2d, but are quite respectable (~1 min$^{-1}$) when presented as acyl-ACP adducts 4c and 4d. Of course, if the KM values for the two anti-diketides when presented as NAC-thioesters are significantly higher than the solubility-limited concentrations that were used in the assay, then the apparent kinetic advantage of channeling the anti-diketides could be artificially high. Even so, these overall results indicate that channeling dramatically increases the efficacy of poor substrates. In addition, the results reported here provide insight into how multimodular PKSs can be so remarkably tolerant toward protein engineering, even though individual modules are fairly specific catalysts.

The Reversibility of ACPn to KSn+1 Transfers. Finally, the ACP-mediated strategy for diketide loading onto acceptor modules also enabled us to address the question of reversibility of the transacylation reaction between the donor ACP and the recipient KS. While co-incubation of $^{14}$C-labeled 2a with holo-ACP4(4) afforded essentially no labeling of the ACP, co-incubation of $^{14}$C-labeled 2a with holo-ACP4(4) in the presence of (5)M2+TE gave both labeled (5)M2+TE and ACP4(4) (FIG. 15A). The proposed mechanism for the observed labeling is shown in FIG. 15B and requires back-transfer of the acyl group from the KS to the ACP of the upstream module. Back-transfer was also observed under turnover conditions, albeit at a substantially reduced level. Thus, the observed directionality of chain transfer in the context of a multimodular PKS that is rapidly turning over appears to arise due to kinetic channeling of these intermediates rather than a ratchet mechanism that explicitly precludes back-transfer. However, given the 20-fold excess of ACP to module, the occupancy level of the diketide on the ACP is quite low. Consequently, in a PKS where two modules on separate polypeptides exist in approximately equimolar ratios, reverse transfer from a downstream module to an upstream module occurs rarely and only at steps where a significant barrier for forward chain transfer is encountered. In contrast, for intermodular chain transfer between modules within the same polypeptide, the effective molarity of the donor ACP group is significantly higher, and reversible transfer may be more significant (but without chemical consequence). The likelihood of intrapolypeptide reverse transfer may explain why the loading didomain shows relatively low selectivity for a propionyl starter unit versus an acetyl starter unit (2:1), see Lau, et al., *Biochemistry* 2000, 39, 10514–10520, whereas DEBS1+TE discriminates strongly (32:1) between the two starter units. See Pieper, et al., *Biochemistry* 1996, 35, 2054–2060.

These studies represent the first direct observation of kinetic channeling of intermediates in a modular PKS. Several dramatic examples are presented for both intrapolypeptide transfers and interpolypeptide transfers where the maximal rate constant ($k_{cat}$) for elongating a particular ketide substrate by a DEBS module increases 10- to >100-fold when the substrate is channeled relative to when it is diffusively presented. Linkers are shown to play an important role in kinetic channeling, although the contribution of other elements, such as the pantetheine arm or protein-protein interactions between the donor and recipient modules, cannot be excluded. In addition, our studies have also reinforced the fact that, while individual modules are tolerant of stereochemical diversity in diketides, they are at the same time fairly specific catalysts. In addition, their specificities and recognition features do not necessarily correlate with the structures of their natural substrates. Finally, we have shown that the transfer step from a donor ACP to an acceptor KS is a fundamentally reversible reaction. Structural and more detailed mechanistic studies on these remarkable multifunctional catalysts should be particularly interesting from the viewpoint of understanding the atomic basis for the phenomena described here.

As used herein, the terms "a", "an", and "any" are each intended to include both the singular and plural forms.

Numerous modifications may be made to the foregoing systems without departing from the basic teachings thereof. Although the present invention has been described in substantial detail with reference to one or more specific embodiments, those of skill in the art will recognize that changes may be made to the embodiments specifically disclosed in this application, yet these modifications and improvements are within the scope and spirit of the invention, as set forth in the specification, drawings, and claims. All publications or patent documents cited in this specification are incorporated herein by reference as if each such publication or document was specifically and individually indicated to be incorporated herein by reference.

Citation of the above publications or documents is not intended as an admission that any of the foregoing is pertinent prior art, not does it constitute any admission as to the contents or date of these publications or documents.

What is claimed is:

1. A method to prepare a desired polyketide which method comprises incubating required substrates with a hybrid modular polyketide synthase (PKS) comprising at least a first extender module and a second extender module of a different PKS from said first module,
   wherein said extender modules are defined as consisting of the amino acid sequence from the N-terminus of the ketosynthase (KS) domain through the C-terminus of the acyl transferase protein (ACP) domain;
   wherein the C-terminus of said first module is covalently linked to the N-terminus of a intra-molecular linker (RAL) and the N-terminus of the second module is covalently linked to the C-terminus of said RAL, and
   wherein said RAL is defined as the amino acid sequence between the C-terminus of an upstream ACP domain and the N-terminus of an adjacent downstream KS domain; said ACP and KS domains occupying adjacent modules in the same reading frame;
   wherein either said first module or second module is not covalently linked to said RAL in a naturally occurring polyketide synthase;
   whereby the RAL effects the transfer of a nascent polyketide chain from said first module to said second module.

2. The method of claim 1 wherein the substrates comprise a diketide thioester and thioesters of the required extender units.

3. The method of claim 2 wherein the extender units are malonyl, methylmalonyl, ethylmalonyl or hydroxymalonyl thioesters.

4. The method of claim 1 wherein said first and second extender modules have structures that are present in naturally occurring PKS.

5. The method of claim 1 wherein said RAL is selected from the group consisting of M2 ery, M4 ery, M6 ery, M2 rif, M3 rif, M5 rif, M3 rap, M4 rap, and M7 rap intra-module linkers (SEQ. ID. NO's: 3–11, respectively).

6. The method of claim 1 wherein said hybrid modular PKS comprises a modular structure selected from the group consisting of:

a) ery modules 1 and 3 through 6 inclusive and tylosin module 2, and wherein said polyketide chain is transferred from ery module 1 to tyl module 2 and then to ery modules 3 through 6 inclusive, b) ery modules 1 through 5 inclusive and narbomycin module 6, wherein said polyketide chain is transferred from ery modules 1 through 5 inclusive to nar module 6, c) modules 1 and 3 through 6 inclusive of ery and modules 2–3 of tylosin, spiramycin or niddamycin, wherein said polyketide chain is transferred from ery module 1 to modules 2–3 of tylosin, spiramycin or niddamycin and then to ery modules 3 through 6 inclusive, d) modules 1 through 3 inclusive of tylosin, spiramycin or niddamycin and modules 3 through 6 inclusive of ery, and wherein said polyketide chain is transferred from modules 1 through 3 inclusive of said tylosin, spiramycin or niddamycin to ery modules 3 through 6 inclusive, e) a module of tylosin, spiramycin or niddamycin and modules 1–2 and 3 through 6 inclusive of ery, wherein said polyketide chain is transferred from ery modules 1–2 to the tylosin, spiramycin or niddamycin module and then to ery modules 3 through 6 inclusive, f) modules 1 and 3 through 6 inclusive of ery and module 5 of tylosin, spiramycin or niddamycin having the enoyl reductase catalytic activity inactivated, wherein said polyketide chain is transferred from ery module 1 to module 5 of tylosin, spiramycin or niddamycin and then to ery modules 3 through 6 inclusive, g) ery modules 1 through 4 inclusive and 6 and module 6 of spiramycin or niddamycin, wherein said polyketide chain is transferred from ery modules 1 through 4 inclusive to module 6 of spiramycin or niddamycin and then to ery module 6, h) module 1 of FK-506 or 520 and modules 2 through 14 inclusive of rapamycin, wherein said polyketide chain is transferred from module 1 of FK-506 or 520 and then to modules 2 through 14 inclusive of rapamycin, i) module 1 and 11 through 14 inclusive of rapamycin and modules 2 through 6 inclusive of FK-506 or 520 wherein said polyketide chain is transferred from module 1 of rapamycin to modules 2 through 6 inclusive of FK-506 or 520 and then to modules 11 through 14 inclusive of rapamycin, j) module 1 of rapamycin, modules 2 through 7 inclusive of FK-506 or 520 and modules 12 through 14 inclusive of rapamycin, wherein said polyketide chain is transferred from module 1 of rapamycin to modules 2 through 7 inclusive of FK-506 or 520 and then to modules 12 through 14 inclusive of rapamycin, k) module 1 of rapamycin, modules 2 through 8 inclusive of FK-506 or 520 and modules 13–14 of rapamycin, wherein said polyketide chain is transferred from module 1 of rapamycin to modules 2 through 8 inclusive of FK-506 or 520 and then to modules 13–14 of rapamycin, and l) modules 1 through 10 inclusive of rapamycin and modules 7 through 10 inclusive of FK-506 or 520, wherein said polyketide chain is transferred from modules 1 through 10 inclusive of rapamycin to modules 7 through 10 inclusive of FK-506 or 520.

7. A method to prepare a desired polyketide which method comprises incubating required substrates with a hybrid modular polyketide synthase (PKS) comprising at least a first extender module and a second extender module of a different PKS from said first module, wherein said extender modules are defined as consisting of the amino acid sequence from the N-terminus of the ketosynthase (KS) domain through the C-terminus of the acyl transferase protein (ACP) domain;

wherein the C-terminus of said first module is covalently linked to the N-terminus of a inter-molecular linker (ERL) and the N-terminus of the second module is covalently linked to the C-terminus of said ERL, and wherein said ERL is defined as a contiguous polypeptide comprising, in order, (1) the amino acid sequence beginning at the C-terminus of the ACP domain of the most downstream module of a first open reading frame and (2) the amino acid sequence upstream of the N-terminus of the most upstream KS domain of a second open reading frame, which second open reading frame is immediately adjacent to and downstream of said first open reading frame; and wherein either said first module or second module is not covalently linked to said ERL in a naturally occurring polyketide synthase;

whereby the ERL effects the transfer of a nascent polyketide chain from said first module to said second module.

8. The method of claim 7 wherein the substrates comprise a diketide thioester and thioesters of the required extender units.

9. The method of claim 8 wherein the extender units are malonyl, methylmalonyl, ethylmalonyl or hydroxymalonyl thioesters.

10. The method of claim 7 wherein said first and second extender modules have structures that are present in naturally occurring PKS.

11. The method of claim 7 wherein the portion of the ERL at the N-terminus of the second module is selected from the group consisting of SEQ. ID. NO's: 12–19, respectively.

12. The method of claim 7 wherein said hybrid modular PKS comprises a modular structure selected from the group consisting of:

a) ery modules 1 and 3 through 6 inclusive and tylosin module 2, and wherein said polyketide chain is transferred from ery module 1 to tyl module 2 and then to ery modules 3 through 6 inclusive, b) ery modules 1 through 5 inclusive and narbomycin module 6, wherein said polyketide chain is transferred from ery modules 1 through 5 inclusive to nar module 6, c) modules 1 and 3 through 6 inclusive of ery and modules 2–3 of tylosin, spiramycin or niddamycin, wherein said polyketide chain is transferred from ery module 1 to modules 2–3 of tylosin, spiramycin or niddamycin and then to ery modules 3 through 6 inclusive, d) modules 1 through 3 inclusive of tylosin, spiramycin or niddamycin and modules 3 through 6 inclusive of ery, and wherein said polyketide chain is transferred from modules 1 through 3 inclusive of said tylosin, spiramycin or niddamycin to ery modules 3 through 6 inclusive, e) a module of tylosin, spiramycin or niddamycin and modules 1–2 and 3 through 6 inclusive of ery, wherein said polyketide chain is transferred from ery modules 1–2 to the tylosin, spiramycin or niddamycin module and then to ery modules 3 through 6 inclusive, f) modules 1 and 3 through 6 inclusive of ery and module 5 of tylosin, spiramycin or niddamycin having the enoyl reductase catalytic activity inactivated, wherein said polyketide chain is transferred from ery module 1 to module 5 of tylosin, spiramycin or niddamycin and then to ery modules 3 through 6 inclusive, g) ery modules 1 through 4 inclusive and 6 and module 6 of spiramycin or niddamycin, wherein said polyketide chain is transferred from ery modules 1 through 4 inclusive to module 6 of spiramycin or niddamycin and then to ery module 6, h) module 1 of FK-506 or 520 and modules 2 through 14 inclusive of rapamycin, wherein said polyketide chain is transferred from module 1 of FK-506 or 520 and then to modules 2 through 14 inclusive of rapamycin, i) module 1 and 11 through 14 inclusive of rapamycin and modules 2 through 6 inclusive of FK-506 or 520 wherein said polyketide chain is transferred from module 1 of rapamycin to modules 2 through 6 inclusive of FK-506 or 520 and then to modules 11 through 14 inclusive of rapamycin, j) module 1 of rapamycin, modules 2 through 7 inclusive of FK-506 or 520 and modules 12 through 14 inclusive of rapamycin, wherein said polyketide chain is transferred from module 1 of rapamycin to modules 2 through 7 inclusive of FK-506 or 520 and then to modules 12 through 14 inclusive of rapamycin, k) module 1 of rapamycin, modules 2 through 8 inclusive of FK-506 or 520 and modules 13–14 of rapamycin, wherein said polyketide chain is transferred from module 1 of rapamycin to modules 2 through 8 inclusive of FK-506 or 520 and then to modules 13–14 of rapamycin, and l) modules 1 through 10 inclusive of rapamycin and modules 7 through 10 inclusive of FK-506 or 520, wherein said polyketide chain is transferred from modules 1 through 10 inclusive of rapamycin to modules 7 through 10 inclusive of FK-506 or 520.

* * * * *